(12) United States Patent
Dai et al.

(10) Patent No.: US 9,476,883 B2
(45) Date of Patent: Oct. 25, 2016

(54) CELLULAR RECOGNITION CONJUGATES AND METHODS OF USE FOR THE HISTOLOGICAL ANALYSIS OF CANCER TISSUE USING MALDI-MS IMAGING

(75) Inventors: Chaofeng Dai, Atlanta, GA (US); Binghe Wang, Marietta, GA (US); Lifang Wang, Atlanta, GA (US); Yong Chu, Shanghai (CN)

(73) Assignee: GEORGIA STATE UNIVERSITY RESEARCH FOUNDATION, Atlanta, GA (US)

( * ) Notice: Subject to any disclaimer, the term of this patent is extended or adjusted under 35 U.S.C. 154(b) by 215 days.

(21) Appl. No.: 14/233,400

(22) PCT Filed: Jul. 20, 2012

(86) PCT No.: PCT/US2012/047557
§ 371 (c)(1),
(2), (4) Date: Jul. 7, 2014

(87) PCT Pub. No.: WO2013/013130
PCT Pub. Date: Jan. 24, 2013

(65) Prior Publication Data
US 2014/0315220 A1 Oct. 23, 2014

Related U.S. Application Data

(60) Provisional application No. 61/509,675, filed on Jul. 20, 2011.

(51) Int. Cl.
*A61K 31/519* (2006.01)
*C09B 11/06* (2006.01)
*G01N 33/574* (2006.01)
(Continued)

(52) U.S. Cl.
CPC ......... *G01N 33/57492* (2013.01); *C09B 1/005* (2013.01); *C09B 11/06* (2013.01); *C09B 57/00* (2013.01)

(58) Field of Classification Search
CPC ............... A61K 31/519; G01N 33/57492; C09B 1/005; C09B 11/06; C09B 57/00
USPC ................. 514/202, 249; 544/256
See application file for complete search history.

(56) References Cited

U.S. PATENT DOCUMENTS

2003/0220245 A1 11/2003 Hubbell et al.
2004/0225119 A1 11/2004 Benson et al.

FOREIGN PATENT DOCUMENTS

WO WO 03/094926 A1 11/2003
WO WO2008/139206 A2 * 11/2008 ............. A61K 49/00

OTHER PUBLICATIONS

Dai et al, Chemical Communications (2011), vol. 47, pp. 10338-10340.*

(Continued)

*Primary Examiner* — Kamal Saeed
*Assistant Examiner* — Janet L Coppins
(74) *Attorney, Agent, or Firm* — Richard S. Echler; FisherBroyles, LLP

(57) ABSTRACT

Disclosed are conjugates that can bind to one or more site on cancer cell surface, for example, surface proteins, compound specific receptors and carbohydrates that comprise the surface of specific cell types. The disclosed conjugates can thereby serve as indicators identifying the presence of cancerous tissue.

19 Claims, 3 Drawing Sheets

(51) Int. Cl.
   *C09B 1/00*     (2006.01)
   *C09B 57/00*    (2006.01)

(56) References Cited

OTHER PUBLICATIONS

Chaofeng Dai, et al., "Using boronolectin in MALDI-MS imaging for the histological analysis of cancer tissue expressing the sialyl Lewis X antigen," Chem. Commun., 2011,47, 10338-10340.
Wolfgang Ebel, et al., "Preclinical evaluation of MORAb-003, a humanized monoclonal antibody antagoizing folate receptor-alpha," Cancer Immunity, vol. 7, p. 6.
Udo Jeschke, et al., "Expression of Sialyl Lewis X, Silalyl Lewis a, E-Cadherin and Cathepsin-D in Human Breast Cancer: Immunohistochemical Analysis in Mammary Carcinoma in Situ, Invasive Carcinomas and their Lymph Node Metastasis," Anticancer Research 25: 1615-1622 (2005).
Reiji Kannagi Carbohydrate Antigen Sialyl Lewis a—Its Pathophsiological Significance and Induction Mechanism in Cancer Progression, Chang Gung Med. J. vol. 30, No. 3 (2007).
Linda E. Kelemen "The role of folate receptor alpha in cancer development, progression and treatment: Cause, consequence of innocent bystander?" Int. J. Cancer: 119, 243-250 (2006).
Alexey V. Ustinov, et al., "Reactive trityl derivatives: stabilised carbocation mass-tags for life sciences applications," Organic & Biomolecular Chemistry, (2008), 6, 4593-4608.
Wenqian Yang, et al., "Diboronic Acids as Fluorescent Probes for Cells Expressing Sialyl Lewis X," Bioorganic & Medicinal Chemistry Letters, 12 (2002), 2175-2177.
Wenqian Yang, et al., "The First Fluorescent Diboronic Acid Sensor Specific for Hepatocellular Carcinoma Cells Expressing Sialyl Lewis X," Chemistry & Biology, vol. 11, 439-448 (2004).
Sabine Zitzmann, et al., "Arginine-Glycine-Aspartic Acid (RGD)-Peptide Binds to Both Tumor and Tumor-Endothelial Cells in Vivo," Cancer Research 62, 5139-5143 (2002).
Chinese Pat. App. No. 201228004711X, National Stage Entry of PCT/US2012/047557, filed Jul. 20, 2012; Office Action dated Oct. 27, 2014.
Chinese Pat. App. No. 201228004711X, National Stage Entry of PCT/US2012/047557, filed Jul. 20, 2012; Response to Office Action and Amended Claims dated Jan. 27, 2015.
Chinese Pat. App. No. 201228004711X, National Stage Entry of PCT/US2012/047557, filed Jul. 20, 2012; Office Action dated Jun. 16, 2015.
Shanta Dhar et al., "Targeted Wingle-Wall Carbon nanotube-Mediated Pt(IV) Prodrug Delivery Using Folate as a Homing Device," JACS, 2008, 130 11467-11476.
European Pat. App. No. 12 815 146.1, filed Jul. 20, 2012; European Search Report and Examination Report dated Jun. 29, 2015.
European Pat. App. No. 12 815 146.1, filed Jul. 20, 2012; Response to European Search Report and Examination Report dated Dec. 15, 2015.
Chinese Pat. App. No. 201280045711X, filed Jul. 20, 2012; Office Action dated Jun. 16, 2015.
Chinese Pat. App. No. 201280045711X, filed Jul. 20, 2012; Response to Office Action dated Oct. 26, 2015.

\* cited by examiner

CELLULAR RECOGNITION CONJUGATES AND METHODS OF USE FOR THE HISTOLOGICAL ANALYSIS OF CANCER TISSUE USING MALDI-MS IMAGING

PRIORITY

This application is a National Stage Entry of PCT/US2012/047557, filed Jul. 20, 2012, which claims priority to U.S. Provisional Application 61/509,675, filed Jul. 20, 2011, the entirety of both applications are incorporated herein by reference.

FIELD

Disclosed are conjugates that can bind to one or more site on cancer cell surface, for example, surface proteins, compound specific receptors and carbohydrates that comprise the surface of specific cell types. The disclosed conjugates can thereby serve as indicators identifying the presence of cancerous tissue.

BACKGROUND

Biomarker-based histological work is known to save lives, help the formulation of therapeutic intervention strategies, and allow for improved prognosis (See, Nathwani B. N. et al., *Adv. Anat. Pathol.*, 2007, 14, 375-400 and J. Teruya-Feldstein, *Arch. Pathol. Lab. Med.*, 2010, 134, 1659-1665). Among all the known biomarkers, cancer cell surface carbohydrate antigens play a very important role, and most clinically measured cancer biomarkers are glycoproteins (See, Ludwig J. A. et al., *Nat. Rev. Cancer*, 2005, 5, 845-856). Cell surface carbohydrate structures as part of glycosylated proteins, peptides, and lipids are characteristic signatures of different cell types and are associated with many forms of cancer. For example, the sialyl Lewis X ($sLe^x$) antigen is being assessed in many cancers; serum $sLe^x$ and cytokeratin 19 fragment are said to be predictive factors for recurrence in patients with stage I non-small cell lung cancer; and $sLe^x$ plus CA 15.3 levels in breast cancer serum were reported to be more effective than CA 15.3 plus CEA (See, Mizuquchi S. et al., *E. J. Cancer Suppl.*, 2007, 6554 and Kurebayashi J. et al., *Jpn. J. Clin. Oncol.*, 2006, 36, 150-153). Furthermore, the combination of $sLe^x$ and $sLe^a$ expression has been shown to mediate adhesion of urothelial cancer cells to activated endothelium. Detection of the changes in expression of these cell surface carbohydrates is clearly very important in cancer histological work.

The folate receptor, a tumor associated glycosylphosphatidylinositol anchored protein, is upregulated in more than 90% of non-mucinous ovarian carcinomas. It is also found at high to moderate levels in kidney, brain, lung, and breast carcinomas while it occurs at very low levels in most normal tissues (Kamen B. A., et al., "A Review of Folate Receptor Alpha Cycling and 5-Methyltetrahydrofolate Accumulation with an Emphasis on Cell Models in vitro," *Adv. Drug Delivery Rev.* 2004, 56 1085-1097). The folate receptor density also appears to increase as the stage of the cancer increases (Elnakat, H., et al., "Distribution, Functionality and Gene Regulation of Folate Receptor Isoforms: Implication in Targeted Therapy," *Adv. Drug Delivery Rev.* 2004, 56 1067-1084).

Tumor cells are characterized by uncontrolled growth, invasion to surrounding tissues, and metastatic spread to distant sites. Mortality from cancer is often due to metastasis since surgical removal of tumors can enhance and prolong survival. The integrins constitute a family of transmembrane receptor proteins composed of heterodimeric complexes of noncovalently linked alpha and beta chains. Integrins function in cell-to-cell and cell-to-extracellular matrix (ECM) adhesive interactions and transduce signals from the ECM to the cell interior and vice versa. Hence, the integrins mediate the ECM influence on cell growth and differentiation. Since these properties implicate integrin involvement in cell migration, invasion, intra- and extra-vasation, and platelet interaction, a role for integrins in tumor growth and metastasis has been established. These findings are underpinned by observations that the integrins are linked to the actin cytoskeleton involving talin, vinculin, and alpha-actinin as intermediaries. Such cytoskeletal changes can be manifested by rounded cell morphology, which is often coincident with tumor transformation via decreased or increased integrin expression patterns. For the various types of cancers, different changes in integrin expression are further associated with tumor growth and metastasis. Tumor progression leading to metastasis appears to involve equipping cancer cells with the appropriate adhesive (integrin) phenotype for interaction with the ECM. Therapies directed at influencing integrin cell expression and function are presently being explored for inhibition of tumor growth, metastasis, and angiogenesis. Such therapeutic strategies include anti-integrin monoclonal antibodies, peptidic inhibitors (cyclic and linear), calcium-binding protein antagonists, proline analogs, apoptosis promotors, and antisense oligonucleotides. Moreover, platelet aggregation induced by tumor cells, which facilitates metastatic spread, can be inhibited by the disintegrins, a family of viper venom-like peptides. Therefore, adhesion molecules from the integrin family and components of angiogenesis might be useful as tumor progression markers for prognostic and for diagnostic purposes. Development of integrin cell expression profiles for individual tumors may have further potential in identifying a cell surface signature for a specific tumor type and/or stage. Thus, recent advances in elucidating the structure, function, ECM binding, and signaling pathways of the integrins have led to new and exciting modalities for cancer therapeutics and diagnoses.

In histological work, fluorescent and/or color staining agents are most commonly used. This approach, however, suffers from difficulties in multiplexing due to spectral resolution/overlap issues and in quantitation. A novel but maturing technology, MALDI imaging mass spectrometry (MALDI-IMS) allows for direct examination of tissue biopsies without the need for micro-dissection and solubilization of tissue biomarkers prior to analysis, and ion desorption can be targeted to specific "points" in a grid pattern and the data rasterized. The resulting spectra can then be used to generate two-dimensional molecular maps of hundreds of biomolecules directly from the surface of a tissue section. These molecular maps display the relative abundance and spatial distribution of these molecules. MALDI tissue profiling has the power to link the molecular detail of mass spectrometry with molecular histology, generating mass spectra correlated to known locations within a thin tissue section. We and others have recently demonstrated the potential of MALDI-IMS to clinical histopathology applications.

There is therefore a long felt need for techniques using cell surface specific agents that can be used for identifying cancerous tissue and therefore the need for cell surface specific biomarkers.

DETAILED DESCRIPTION

Figure 1:
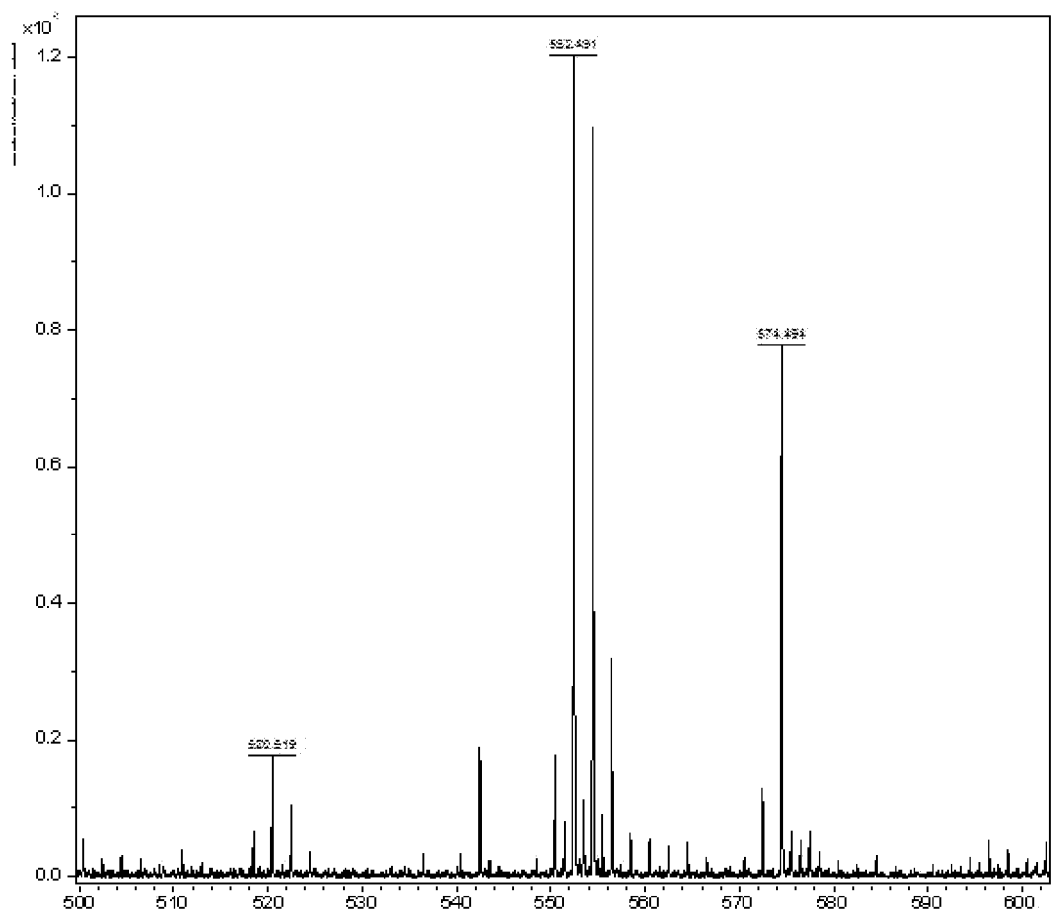
FIG. 1 depicts the MALDI-IMS peak of the stable carbocation generated from the boronolectin-MS tag conjugate disclosed in Example 3 taken from frozen kidney tissue cut and stored at −80° C.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., vascular leakage). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed.

The terms "affinity," "affinity attachment" or "affinity binding" as they relate to the means by which the disclosed X units attach to the target polysaccharides can be by any suitable method. Non-limiting examples include formation of one or more covalent bonds between the polysaccharide and the X unit, formation of one or more hydrogen bonds between the polysaccharide and the X unit, formation of one or more electrostatic bonds between the polysaccharide and the X unit, and combinations thereof.

The term "specific affinity" as it relates to the ability of a disclosed X unit to bind or have affinity for a polysaccharide means that a disclosed imaging agent binds only to a single polysaccharide, for example, an imaging agent having affinity for only sialyl Lewis X (SLe$^x$) or affinity only for Sialyl Lewis a (SLe$^a$). Likewise, the disclosed imaging agents have specific integrin specificity, for example, to the arginine-glycine-aspartic acid (RGD) cell adhesion sequence found on fibronectin. In addition, "special affinity" relates to the binding on cellular folate receptors.

The term "selective affinity" as it relates to the ability of a disclosed X unit to bind or have affinity for a polysaccharide, RGD cell adhesion sequence, or folate binding receptor means that a disclosed imaging agent can bind to a plurality of different binding sites for which the imaging agents are targeted. One non-limiting example relating to sell surface polysaccharides is that a particular X unit can have affinity for more than one polysaccharide, or the formulator can include into the structure of a particular X unit, moieties that can bind to different polysaccharides. Included in the present disclosure are X units comprising a moiety that can bind to a first polysaccharide and a moiety that can bind to a second polysaccharide. A non-limiting example is an X unit having a moiety capable of specific affinity for sialyl Lewis X (SLe$^x$) and a moiety capable of specific affinity for Sialyl Lewis a (SLe$^a$).

Terms such as "saccharide," "polysaccharide," "carbohydrate" and glycan are used interchangeably in the present disclosure and stand for compounds comprising one or more pentoses, hexoses, and the like.

The term arginine-glycine-aspartic acid (RGD) integrin refers to the three amino acid sequence and all other amino acids that are necessary for binding of the imaging agents to the surface of a cell.

Matrix-Assisted Laser Desorption/Ionization (MALDI)

The disclosed imaging agents can be used in conjunction with MALDI and other tissue compatible mass spectral procedures. In general, and without limitation, MALDI is a soft ionization technique used in mass spectrometry, allowing the analysis of biomolecules (biopolymers such as proteins, peptides and sugars) and large organic molecules (such as polymers, dendrimers and other macromolecules), which tend to be fragile and fragment when ionized by more conventional ionization methods. It is most similar in character to electrospray ionization both in relative softness and the ions produced (although it causes many fewer multiply charged ions). The ionization is triggered by a source of electromagnetic radiation, i.e., a laser beam (normally a nitrogen laser). A matrix is used to protect the biomolecule from being destroyed by direct laser beam and to facilitate vaporization and ionization, however, the imaging agents disclosed herein can be used with techniques that do not utilize a matrix.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (carbocyclic and aryl rings) or can comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and unsubstituted acyclic hydrocarbyl:
   For the purposes of the present disclosure the term "substituted and unsubstituted acyclic hydrocarbyl" encompasses 3 categories of units:
   1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
   2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
   3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.
B. Substituted and unsubstituted cyclic hydrocarbyl:
   For the purposes of the present disclosure the term "substituted and unsubstituted cyclic hydrocarbyl" encompasses 5 categories of units:
   1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
      i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
      ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decalinyl ($C_{10}$), decahydroazulenyl ($C_{10}$).
      iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.
   2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
      i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
      ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).
   3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:
      i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).
      ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).
   4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
      i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$).

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

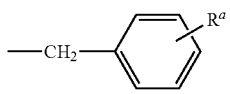

wherein $R^a$ is optionally one or more independently chosen substitutions for hydrogen. Further examples include other aryl units, inter alia, (2-hydroxyphenyl) hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

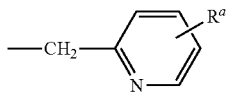

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan can have alternative characterizations. For example, 1,2,3,4-tetrahydroquinoline having the formula:

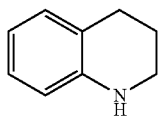

is, for the purposes of the present disclosure, considered a heterocyclic unit. 6,7-Dihydro-5H-cyclopentapyrimidine having the formula:

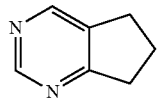

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

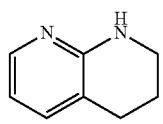

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms can be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) substituted or unsubstituted $C_1$-$C_{12}$ linear, $C_3$-$C_{12}$ branched, or $C_3$-$C_{12}$ cyclic alkyl; for example, methyl ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3- dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethyl-hept-3-ynyl ($C_9$), and the like;

iv) substituted or unsubstituted $C_6$ or $C_{10}$ aryl; for example, phenyl, 2-chlorophenyl, 3-hydroxyphenyl, 4-nitrophenyl, 2-fluoro-4-methylphenyl, 3,5-dinitrophenyl, 8-hydroxynaphth-1-yl, 6-sulfonylnapth-2-yl, and the like;

v) substituted or unsubstituted $C_1$-$C_9$ heterocyclic; for example, as defined further herein;

vi) substituted or unsubstituted $C_1$-$C_{11}$ heteroaryl; for example, as defined further herein;

vii) halogen; for example, fluoro, chloro, bromo, and iodo;

viii) —$[C(R^{23a})(R^{23b})]_xOR^{10}$;

$R^{10}$ is chosen from:
  a) —H;
  b) substituted or unsubstituted $C_1$-$C_{12}$ linear, $C_3$-$C_{12}$ branched, or $C_3$-$C_{12}$ cyclic alkyl;
  c) $C_6$ or $C_{10}$ substituted or unsubstituted aryl or alkylenearyl;
  d) $C_1$-$C_9$ substituted or unsubstituted heterocyclic;
  e) $C_1$-$C_{11}$ substituted or unsubstituted heteroaryl;

ix) —$[C(R^{23a})(R^{23b})]_xN(R^{11a})(R^{11b})$;

$R^{11a}$ and $R^{11b}$ are each independently chosen from:
  a) —H;
  b) —$OR^{12}$;
    $R^{12}$ is hydrogen or $C_1$-$C_4$ linear alkyl;
  c) substituted or unsubstituted $C_1$-$C_{12}$ linear, $C_3$-$C_{12}$ branched, or $C_3$-$C_{12}$ cyclic alkyl;
  d) $C_6$ or $C_{10}$ substituted or unsubstituted aryl;
  e) $C_1$-$C_9$ substituted or unsubstituted heterocyclic;
  f) $C_1$-$C_{11}$ substituted or unsubstituted heteroaryl; or
  g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;

x) —$[C(R^{23a})(R^{23b})]_xC(O)R^{13}$;

$R^{13}$ is:
  a) substituted or unsubstituted $C_1$-$C_{12}$ linear, $C_3$-$C_{12}$ branched, or $C_3$-$C_{12}$ cyclic alkyl;
  b) —$OR^{14}$;
    $R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
  c) —$N(R^{15a})(R^{15b})$;
    $R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xi) —$[C(R^{23a})(R^{23b})]_xOC(O)R^{16}$;

$R^{16}$ is:
  a) substituted or unsubstituted $C_1$-$C_{12}$ linear, $C_3$-$C_{12}$ branched, or $C_3$-$C_{12}$ cyclic alkyl;
  b) —$N(R^{17a})(R^{17b})$;
    $R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —$[C(R^{23a})(R^{23b})]_xNR^{18}C(O)R^{19}$;

$R^{18}$ is:
  a) —H; or
  b) substituted or unsubstituted $C_1$-$C_4$ linear, $C_3$-$C_4$ branched, or $C_3$-$C_4$ cyclic alkyl;

$R^{19}$ is:
  a) substituted or unsubstituted $C_1$-$C_{12}$ linear, $C_3$-$C_{12}$ branched, or $C_3$-$C_{12}$ cyclic alkyl;
  b) —$N(R^{20a})(R^{20b})$;
    $R^{20a}$ and $R^{20b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

xiii) —$[C(R^{23a})(R^{23b})]_xCN$;

xiv) —$[C(R^{23a})(R^{23b})]_xNO_2$;

xv) —$[C(R^{23a})(R^{23b})]_xR^{21}$;

$R^{21}$ is $C_1$-$C_{10}$ linear, $C_3$-$C_{10}$ branched, or $C_3$-$C_{10}$ cyclic alkyl substituted by from 1 to 21 halogen atoms chosen from —F, —Cl, —Br, or —I;

xvi) —$[C(R^{23a})(R^{23b})]_xSO_2R^{22}$;

$R^{22}$ is hydrogen, hydroxyl, substituted or unsubstituted $C_1$-$C_4$ linear or $C_3$-$C_4$ branched alkyl; substituted or unsubstituted $C_6$, $C_{10}$, or $C_{1-4}$ aryl; $C_7$-$C_{15}$ alkylenearyl; $C_1$-$C_9$ substituted or unsubstituted heterocyclic; or $C_1$-$C_{11}$ substituted or unsubstituted heteroaryl;

$R^{23a}$ and $R^{23b}$ are each independently hydrogen or $C_1$-$C_4$ alkyl; and the index x is an integer from 0 to 5.

Disclosed herein are compounds having the general formula:

$$\boxed{X} - L - Z$$

wherein X is a unit that is capable of binding to one or more locations on a cancer cell surface;

L is a linking unit; and

Z is a unit capable of forming a stable carbocation.

In a further aspect, the disclosed X units are capable of attaching to a small molecule receptor. In one embodiment, the X unit comprises a folate moiety which causes the imaging agent to bind to the folate receptor on a tumor cell.

In addition to X units, the disclosed compounds further comprise a means for indicating that the molecules have attached to a particular glycosylated molecule. The disclosed imaging agents comprise Z units that are capable of forming a stable cation when the disclosed imaging agents are fragmented under the conditions of mass spectrum analysis. Z units are also referred to herein as "reporter" units because it is the stable carbocation of Z units that are detected in the disclosed process.

A recently developed variant of MALDI-IMS, termed Targeted Imaging Mass Spectrometry (TIMS) or TAMSIM for Targeted multiplex Mass Spectrometry Imaging, first described by Theiry (See Theiry et al., *Rapid Commun Mass Spectrom*, 2007, 21, 823-829) allows for the targeted analysis and spatial visualization of a disclosed imaging agent directly from tissue sections by the use of laser-reactive photo-cleavable Z units attached to the disclosed X units which serve as affinity tags. A bond that conjugates the Z unit to the X unit is photocleavable so that exposure to the UV laser in a MALDI mass spectrometer releases the stable cation forming Z unit, which is readily detected without the use of matrix. Changing the mass of the Z unit also allows for multiplexed detection of different molecules simultaneously within the same tissue, and sections prepared by standard methods (fixed or frozen) can be used for TIMS so that existing pathology workflows are the same.

X Units

Saccharide Binding Imaging Agents

In one aspect, the disclosed X units are capable of attaching to a polysaccharide, especially polysaccharides which are a part of cell surface carbohydrates that are a component of glycosylated proteins, peptides, and lipids that are the characteristic signatures of different cell types. The attachment to the polysaccharide can be through covalent bonding, hydrogen bonding, ionic attraction, and the like. In some examples X units will attach by a combination of mechanisms.

Without wishing to be limited by theory, many of these glycosylated molecules to which the disclosed X units are capable of attachment are associated with different forms of cancer. There for the disclosed X units can serve as a component of a biomarker indicating the cancer's presence. For example, Sialyl Lewis X (SLe$^x$) and Sialyl Lewis a (SLe$^a$) are carbohydrate molecules that mediate the adhesion between tumor cells and the endothelium. These antigens are not expressed on normal breast tissue or the tissues of other healthy cells. Overexpression of SLe$^x$ and SLe$^a$ has been found to be indicated with poor prognosis and malignant relapse. Therefore, tissue which is normally thought to be absent these malignancy indicating polysaccharides can be tested for the presence of tumor cells by measuring whether molecules comprising the disclosed X units adhere to the tissue.

One category of the imaging agents relates to imaging agents capable of binding to a cell surface polysaccharide. As such, this category of the disclosed imaging agents X units that comprise one or more boronic acid units having the formula —B(OH)$_2$ wherein the X unit can be represented by the formula:

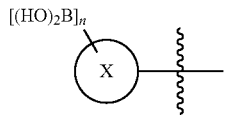

and n is an integer having a value of at least 1.

In one aspect, X units comprise 1 boronic acid unit, i.e., n is equal to 1. In another aspect, X units comprise 2 boronic acid units, i.e., n is equal to 2. In a further aspect, X units comprise 3 boronic acid units, i.e., n is equal to 3. In a still further aspect, X units comprise 4 boronic acid units, i.e., n is equal to 4. In a yet another aspect, X units comprise 5 boronic acid units, i.e., n is equal to 5. The index n, however, can have any value, for example, 1, 2, 3, 4, 5, 6, 7, 8, 9, 10, 11, 12, 13, 14, 15, 16, 17, 18, 19 or 20.

One aspect of X relates to units having the formula:

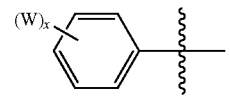

wherein W is a an affinity unit comprising one or more boronic acid units and the index x is from 1 to 5.

One aspect of W relates to affinity units having the formula:

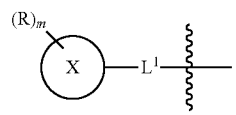

wherein Y is an aryl core chosen from phenyl (C$_6$), naphthyl (C$_{10}$), anthracenyl (C$_{14}$), phenanthrenyl (C$_{14}$), and tetracenyl (C$_{18}$); L$^1$ is a linking group that links W to X; and R is a unit containing at least one boronic acid unit; the index m is an integer from 1 to 5.

L$^1$ is a unit having the formula —R$^4$QR$^5$— wherein R$^4$ and R$^5$ are alkylene units that can be present or absent and wherein each R$^4$ and R$^5$ unit when present contains from 1 to 10 carbon atoms. Q is a unit having the formula (D)$_a$C(E)(G)$_b$ wherein D and G are each independently chosen from —O—, —NH—, and —S—; E is chosen from =O, =NH, and =S; the indices a and b are each independently from 0 to 10. Non-limiting examples of L$^1$ include units chosen from:

i) —(CH$_2$)$_y$C(O)O(CH$_2$)$_z$—;
ii) —(CH$_2$)$_y$OC(O)(CH$_2$)$_z$—;
iii) —(CH$_2$)$_y$C(O)NR$^6$(CH$_2$)$_z$—;
iv) —(CH$_2$)$_y$NR$^6$C(O)(CH$_2$)$_z$—;
v) —(CH$_2$)$_y$NR$^6$C(O)NH(CH$_2$)$_z$—; and
vi) —(CH$_2$)$_y$NR$^6$C(NR$^6$)NR$^6$(CH$_2$)$_z$—;

wherein R$^6$ is hydrogen or C$_1$-C$_3$ linear alkyl; the index y is an integer from 0 to 4 and the index z is an integer form 0 to 4.

R units are units that can be substituted with from 1 to 5 boronic acid units, said R units having the formula:

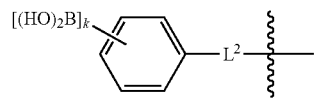

wherein the index k is an integer from 1 to 5; and L$^2$ has the formula:

i) (CH$_2$)$_p$NR$^7$(CH$_2$)$_q$; or
ii) (CH$_2$)$_p$O(CH$_2$)$_q$;

wherein $R^7$ is hydrogen or $C_1$-$C_3$ linear alkyl; the index p is an integer from 0 to 5; and the index q is an integer from 0 to 5.

One embodiment of X relates to units having the formula:

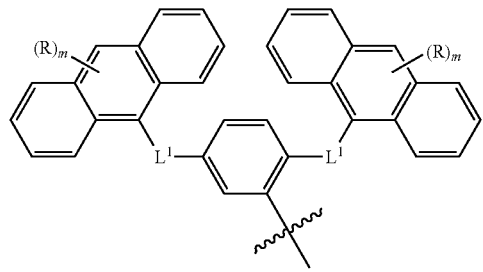

wherein Y is anthracenyl substituted by from 1 to 5 R units.

One iteration of this embodiment relates to X units having the formula:

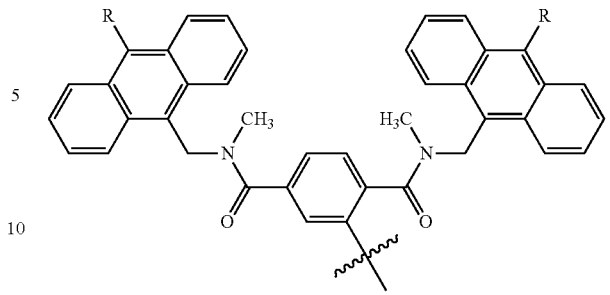

wherein $L^1$ is —$(CH_2)_y C(O)NR^6(CH_2)_z$—; $R^6$ is methyl; the index y is 0; and the index z is 1.

Non-limiting examples of this embodiment include X units wherein $L^2$ is —$CH_2NCH_3CH_2$—, for example:

i)

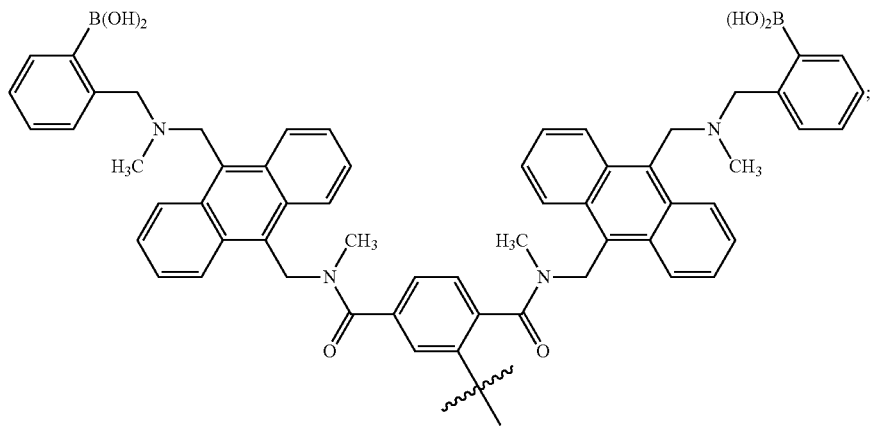

ii)

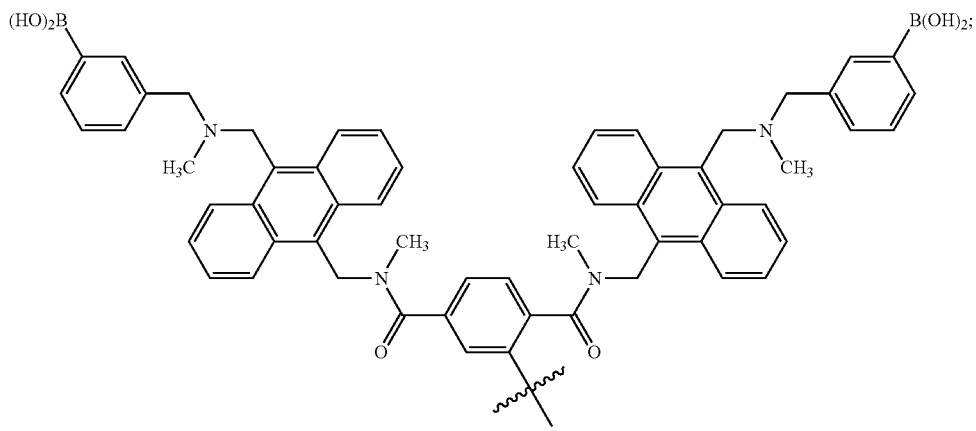

iii)
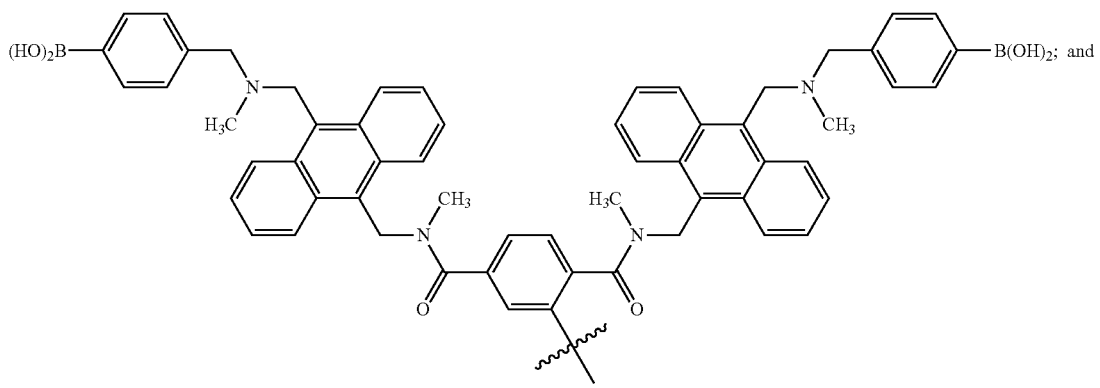
iv)
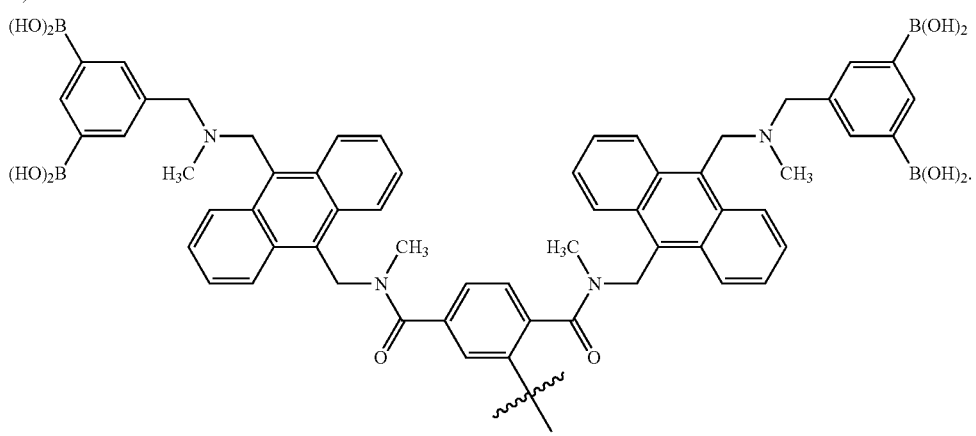
Other non-limiting examples of this embodiment include X units wherein $L^2$ is —CH$_2$OCH$_2$—, for example:
i)
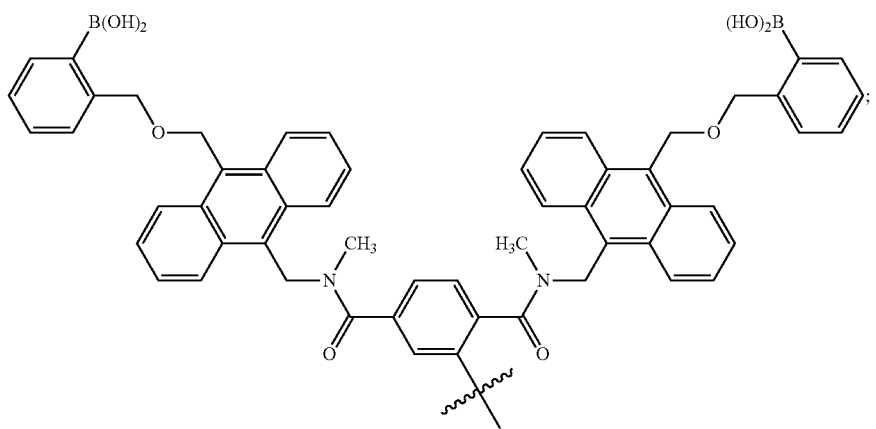

ii)
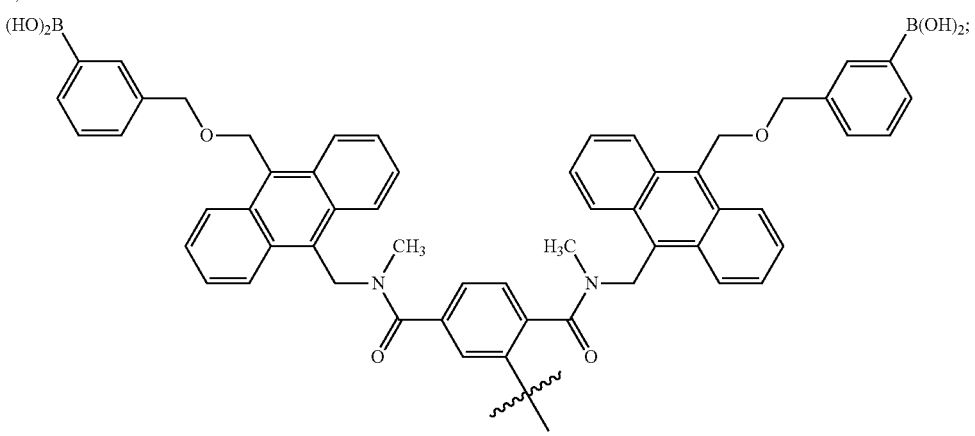
iii)
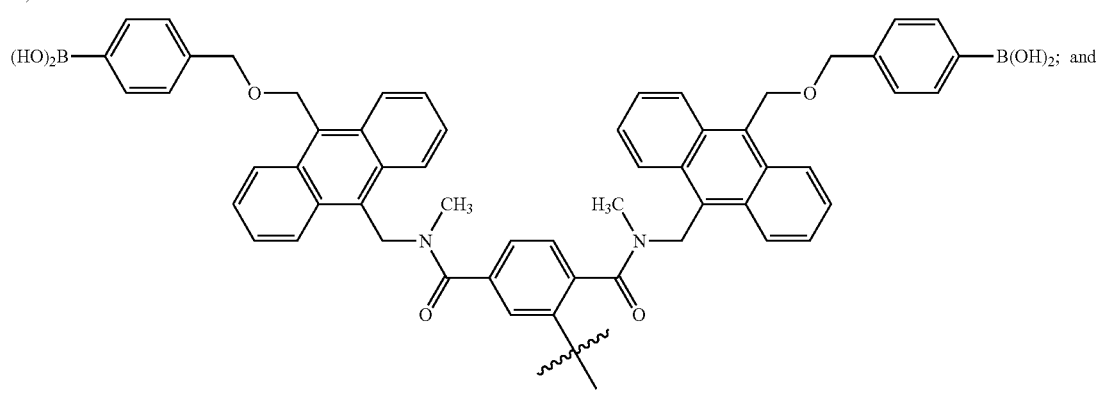
iv)
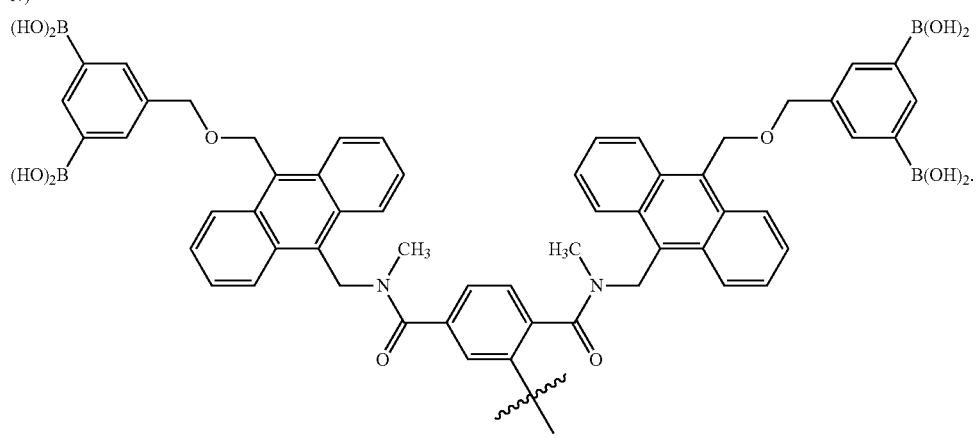
Another iteration of this embodiment relates to X units having the formula:
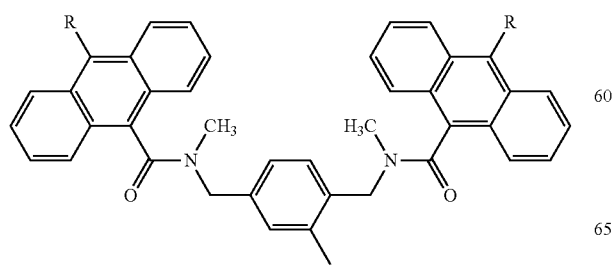

wherein $L^1$ is —$(CH_2)_yC(O)NR^3(CH_2)_z$—; $R^6$ is methyl; the index y is 1; and the index z is 0. When $L^2$ is —$CH_2NCH_3CH_2$—, the disclosed imagining agents comprise an X unit having the formula:

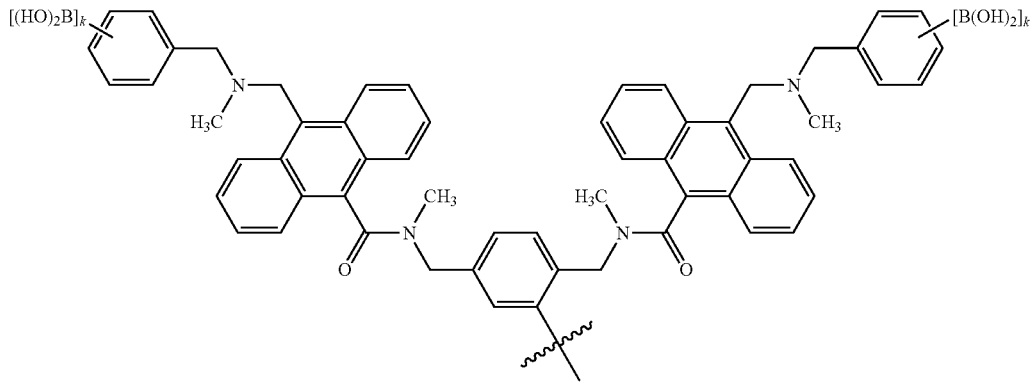

When $L^2$ is —$CH_2OCH_2$—, the disclosed imagining agents comprise an X unit having the formula:

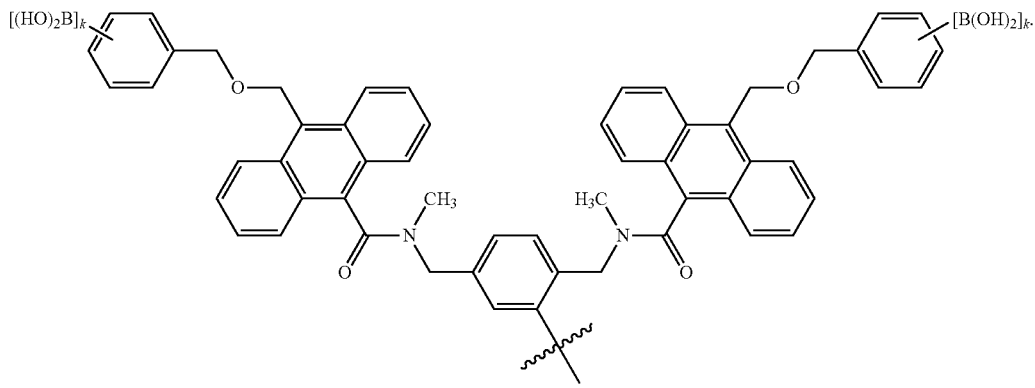

When $L^1$ is —$(CH_2)_yOC(O)(CH_2)_z$—; the index y is equal to 1; the index z is equal to 0; and $L^2$ is —$CH_2NCH_3CH_2$—, the disclosed imagining agents comprise an X unit having the formula:

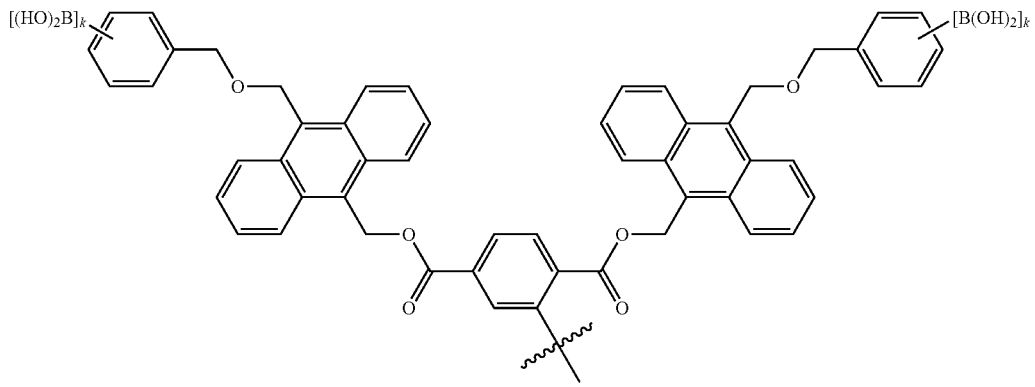

Another embodiment of X relates to units having the formula:
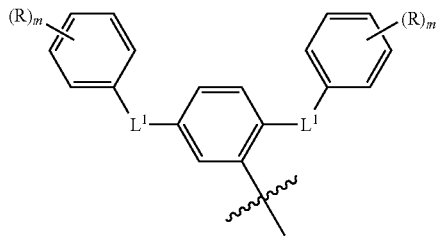
wherein Y is phenyl substituted by from 1 to 5 R units.
One iteration of this embodiment relates to X units having the formula:
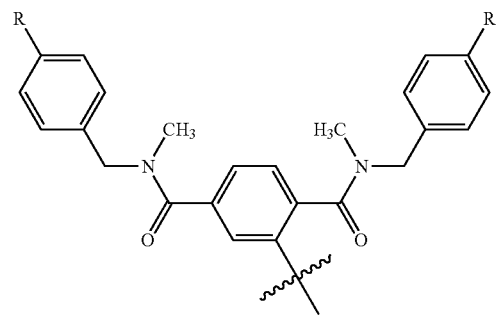
wherein $L^1$ is —$(CH_2)_y C(O)NR^6(CH_2)_z$—; $R^6$ is methyl; the index y is 0; and the index z is 1.
Non-limiting examples of this embodiment include X units wherein $L^2$ is —$CH_2NCH_3CH_2$—, for example:
i)
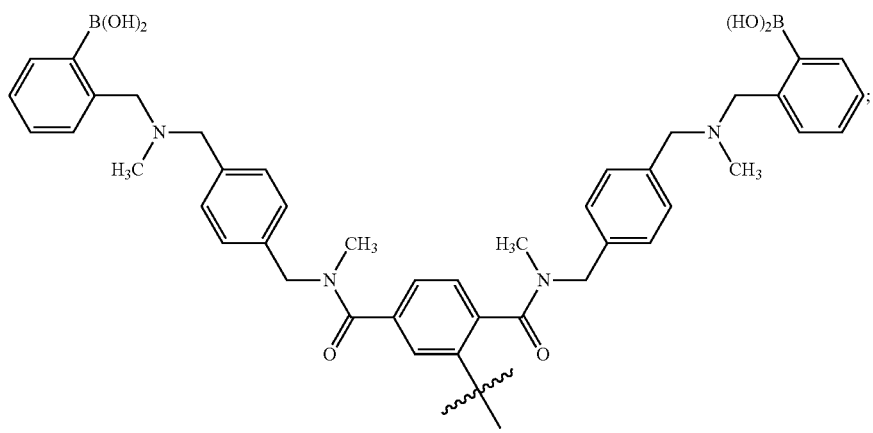
ii)
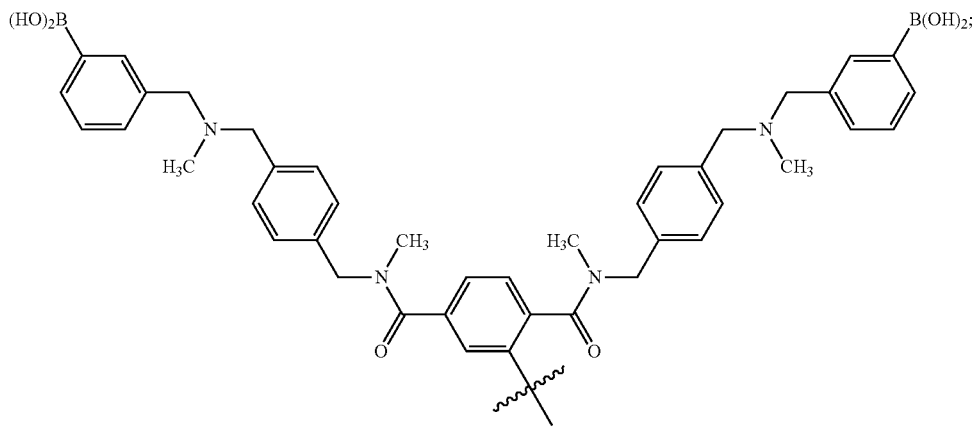

iii)
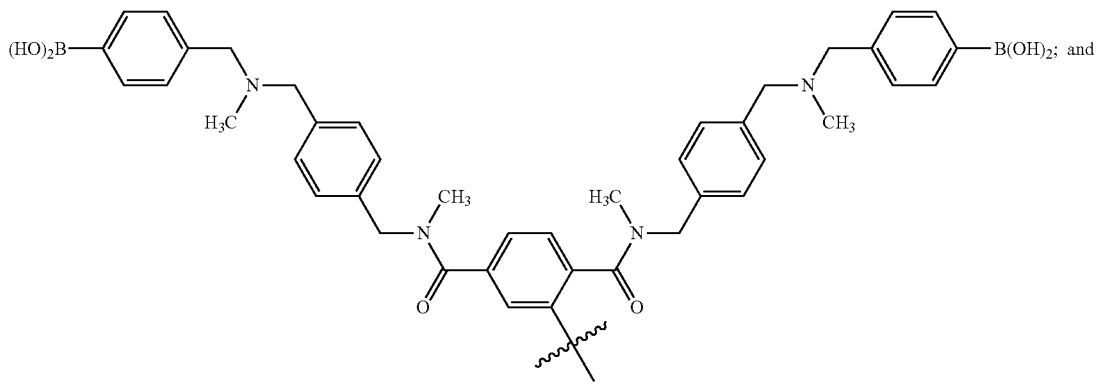
iv)
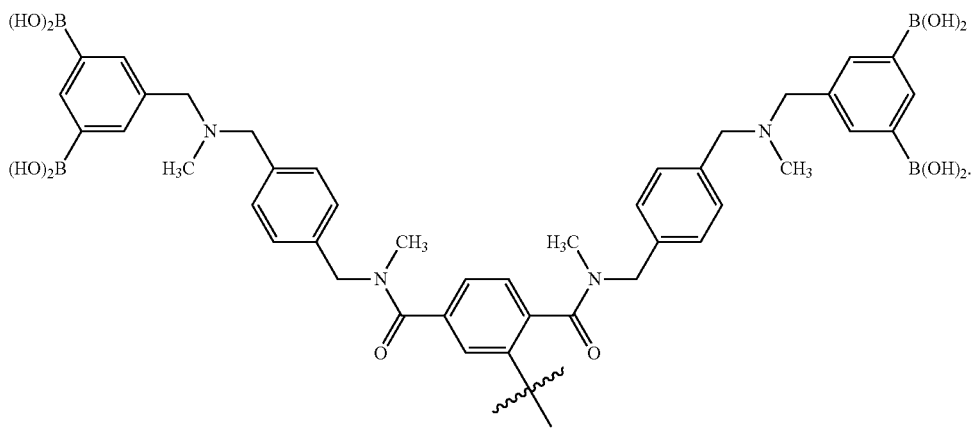
A further embodiment of X relates to units having the formula:
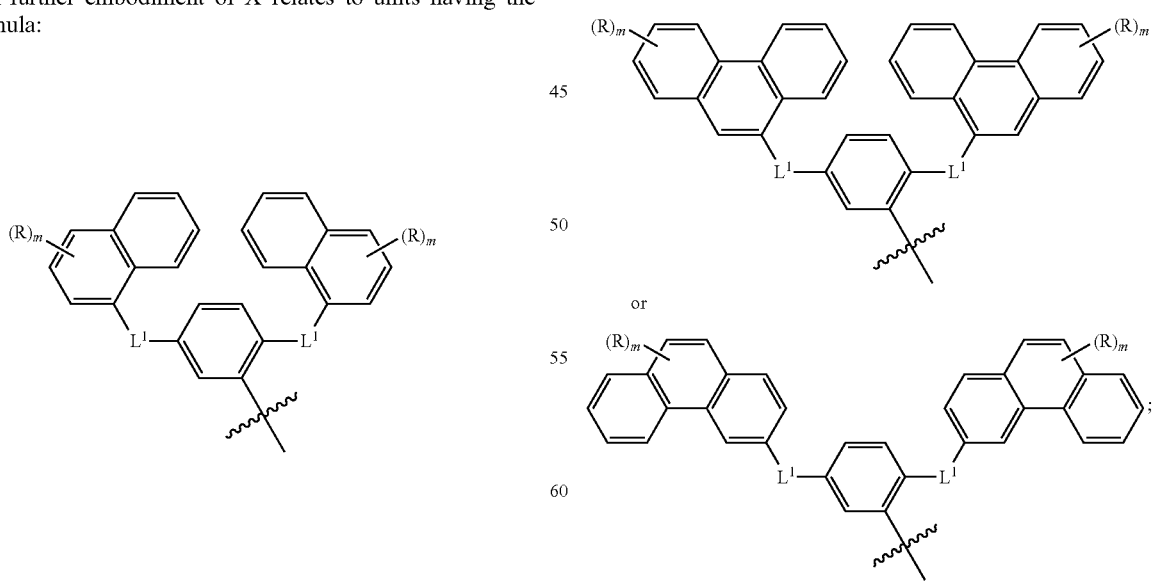
wherein Y is naphthyl substituted by from 1 to 5 R units.
A still further embodiment of X relates to units having the formula:
wherein Y is phenanthrenyl substituted by from 1 to 5 R units.

Integrin Binding Imaging Agents

Another aspect of the disclosed imaging agents relates to compounds having the formula:

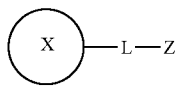

wherein X is a unit that is capable of binding to one or more integrins and L and Z are the same as defined herein. In one category of this aspect, the disclosed X units comprise an arginine-glycine-aspartic acid sequence capable of binding to a tumor cell integrin. In embodiment the X units are linear RGD units having the formula:

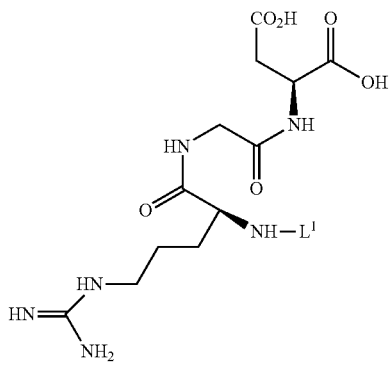

wherein the X unit is capable of binding to a fibronectin III domain on a protein found on the tumor cell surface. For this category of imaging agents $L^1$ has the formula:

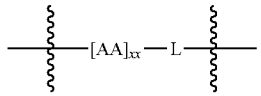

wherein AA represents xx number of naturally occurring or synthetic amino acids. The index xx is an integer from 1 to 7. In one embodiment xx is equal to 2. In a further embodiment xx is equal to 3. In another embodiment xx is equal to 4. In another further embodiment xx is equal to 5. In a still further embodiment xx is equal to 6. In a yet another embodiment xx is equal to 7.

Another category of X units of this aspect has the general formula:

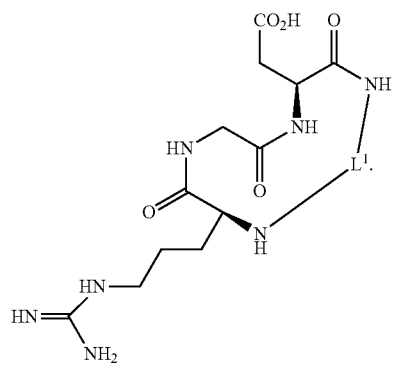

For this category of imaging agents $L^1$ has the formula:

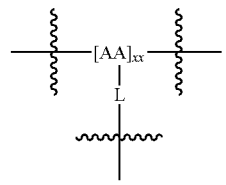

wherein AA represents xx number of naturally occurring or synthetic amino acids. The index xx is an integer from 1 to 7. In one embodiment xx is equal to 2. In a further embodiment xx is equal to 3. In another embodiment xx is equal to 4. In another further embodiment xx is equal to 5. In a still further embodiment xx is equal to 6. In a yet another embodiment xx is equal to 7.

In one embodiment, the amino acids which comprise $L^1$ are chosen from alanine, arginine, asparagine, aspartic acid, cysteine, glutamic acid, glutamine, glycine, histidine, isoleucine, leucine, lysine methionine, ornithine, phenylalanine, proline, serine, threonine, tryptophan, tyrosine, and valine.

The following are non-limiting examples of RGD binding imaging agents indicating the amino acids that comprise RGD and $L^1$:

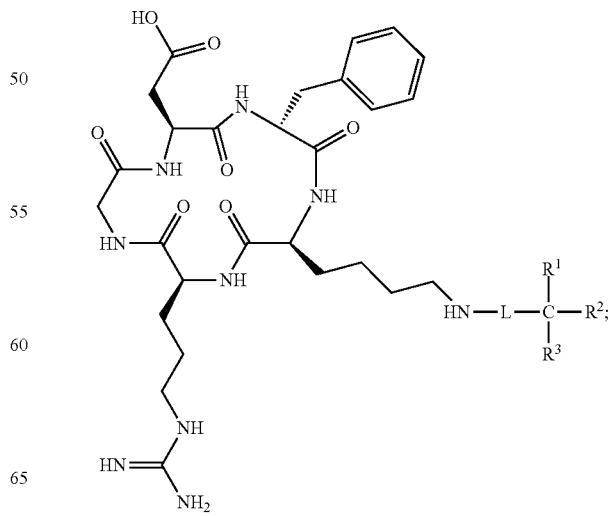

-continued
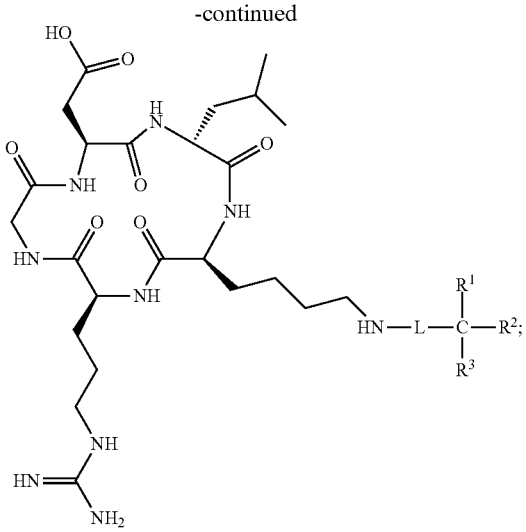
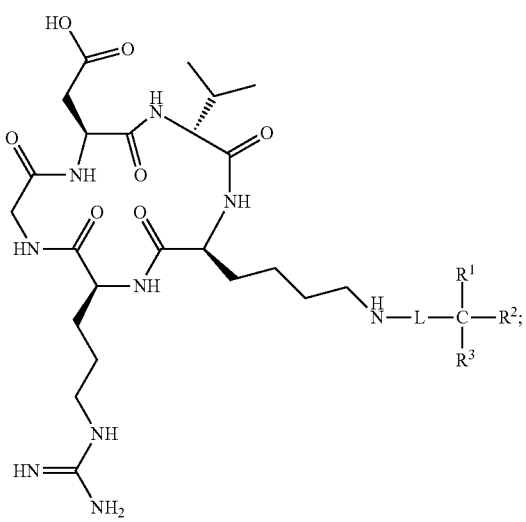
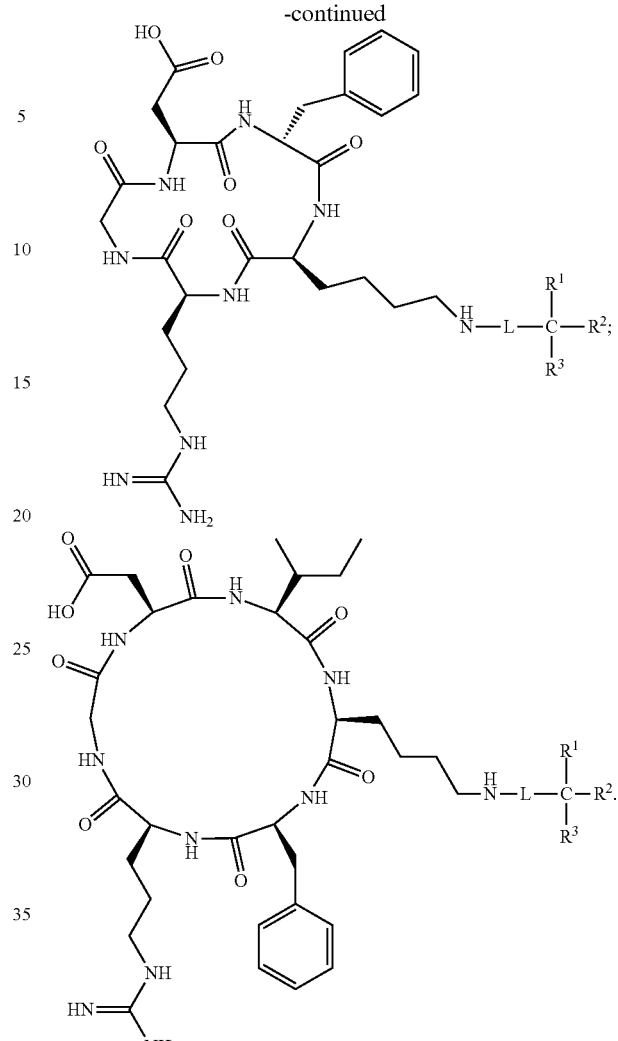
Folate Receptor Binding Imaging Agents
In another aspect, the disclosed X units are capable of attaching to a folate receptor. This category of X units has the general formula:
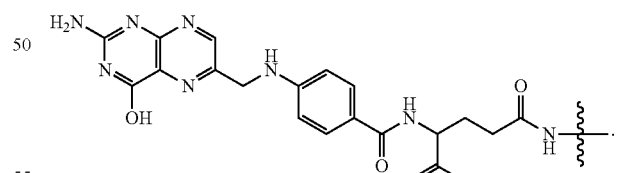
Z Units
Z units have the formula:
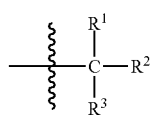

wherein when the Z unit is fragmented from the core molecule, Z is capable of forming a stable carbocation having the formula:

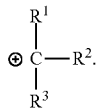

$R^1$ an $R^2$ are substituted or unsubstituted aryl groups chosen from phenyl ($C_6$), naphthyl ($C_{10}$), anthracenyl ($C_{14}$), phenanthrenyl ($C_{14}$), and tetracenyl ($C_{18}$). $R^3$ is a substituted or unsubstituted aryl groups chosen from phenyl ($C_6$), naphthyl ($C_{10}$), anthracenyl ($C_{14}$), phenanthrenyl ($C_{14}$), and tetracenyl ($C_{18}$) that further comprises an anchoring group.

The following are non-limiting examples of units which can substitute for hydrogen atoms on a $R^1$, $R^2$ and $R^3$ aryl rings:

i) substituted or unsubstituted $C_1$-$C_{12}$ linear, $C_3$-$C_{12}$ branched, or $C_3$-$C_{12}$ cyclic alkyl; for example, methyl ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethyl-hept-3-ynyl ($C_9$), and the like;

iv) substituted or unsubstituted $C_6$ or $C_{10}$ aryl; for example, phenyl, 2-chlorophenyl, 3-hydroxyphenyl, 4-nitrophenyl, 2-fluoro-4-methylphenyl, 3,5-dinitrophenyl, 8-hydroxynaphth-1-yl, 6-sulfonylnapth-2-yl, and the like;

v) substituted or unsubstituted $C_1$-$C_9$ heterocyclic; for example, as defined further herein;

vi) substituted or unsubstituted $C_1$-$C_{11}$ heteroaryl; for example, as defined further herein;

vii) halogen; for example, fluoro, chloro, bromo, and iodo;

viii) —$[C(R^{23a})(R^{23b})]_xOR^{10}$;
$R^{10}$ is chosen from:
a) —H;
b) substituted or unsubstituted $C_1$-$C_{12}$ linear, $C_3$-$C_{12}$ branched, or $C_3$-$C_{12}$ cyclic alkyl;
c) $C_6$ or $C_{10}$ substituted or unsubstituted aryl or alkylenearyl;
d) $C_1$-$C_9$ substituted or unsubstituted heterocyclic;
e) $C_1$-$C_{11}$ substituted or unsubstituted heteroaryl;

ix) —$[C(R^{23a})(R^{23b})]_xN(R^{11a})(R^{11b})$;
$R^{11a}$ and $R^{11b}$ are each independently chosen from:
a) —H;
b) —$OR^{12}$;
$R^{12}$ is hydrogen or $C_1$-$C_4$ linear alkyl;
c) substituted or unsubstituted $C_1$-$C_{12}$ linear, $C_3$-$C_{12}$ branched, or $C_3$-$C_{12}$ cyclic alkyl;
d) $C_6$ or $C_{10}$ substituted or unsubstituted aryl;
e) $C_1$-$C_9$ substituted or unsubstituted heterocyclic;
f) $C_1$-$C_{11}$ substituted or unsubstituted heteroaryl; or
g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;

x) —$[C(R^{23a})(R^{23b})]_xC(O)R^{13}$;
$R^{13}$ is:
a) substituted or unsubstituted $C_1$-$C_{12}$ linear, $C_3$-$C_{12}$ branched, or $C_3$-$C_{12}$ cyclic alkyl;
b) —$OR^{14}$;
$R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
c) —$N(R^{15a})(R^{15b})$;
$R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xi) —$[C(R^{23a})(R^{23b})]_xOC(O)R^{16}$;
$R^{16}$ is:
a) substituted or unsubstituted $C_1$-$C_{12}$ linear, $C_3$-$C_{12}$ branched, or $C_3$-$C_{12}$ cyclic alkyl;
b) —$N(R^{17a})(R^{7b})$;
$R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —$[C(R^{23a})(R^{23b})]_xNR^{18}C(O)R^{19}$;
$R^{18}$ is:
a) —H; or
b) substituted or unsubstituted $C_1$-$C_4$ linear, $C_3$-$C_4$ branched, or $C_3$-$C_4$ cyclic alkyl;
$R^{19}$ is:
a) substituted or unsubstituted $C_1$-$C_{12}$ linear, $C_3$-$C_{12}$ branched, or $C_3$-$C_{12}$ cyclic alkyl;
b) —$N(R^{20a})(R^{20b})$;
$R^{20a}$ and $R^{20b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

xiii) —[C(R$^{23a}$)(R$^{23b}$)]$_x$CN;
xiv) —[C(R$^{23a}$)(R$^{23b}$)]$_x$NO$_2$;
xv) —[C(R$^{23a}$)(R$^{23b}$)]$_x$R$^2$;
  R$^{21}$ is C$_1$-C$_{10}$ linear, C$_3$-C$_{10}$ branched, or C$_3$-C$_{10}$ cyclic alkyl substituted by from 1 to 21 halogen atoms chosen from —F, —Cl, —Br, or —I;
xvi) —[C(R$^{23a}$)(R$^{23b}$)]$_x$SO$_2$R$^{22}$;
  R$^{22}$ is hydrogen, hydroxyl, substituted or unsubstituted C$_1$-C$_4$ linear or C$_3$-C$_4$ branched alkyl; substituted or unsubstituted C$_6$, C$_{10}$, or C$_{1-4}$ aryl; C$_7$-C$_{15}$ alkylenearyl; C$_1$-C$_9$ substituted or unsubstituted heterocyclic; or C$_1$-C$_{11}$ substituted or unsubstituted heteroaryl;
R$^{23a}$ and R$^{23b}$ are each independently hydrogen or C$_1$-C$_4$ alkyl; and
the index x is an integer from 0 to 5.
  R$^3$ units comprise at least one anchoring unit having the formula:

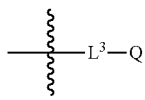

wherein Q is a unit having the formula:
  i) —(CH$_2$)$_r$C(O)O(CH$_2$)$_t$R$^9$;
  ii) —(CH$_2$)$_r$OC(O)(CH$_2$)$_t$R$^9$;
  iii) —(CH$_2$)$_r$C(O)NR(CH$_2$)$_t$R$^9$;
  iv) —(CH$_2$)$_r$NR$^8$C(O)(CH$_2$)$_t$R$^9$;
  v) —(CH$_2$)$_r$NR$^8$C(O)NH(CH$_2$)$_t$R$^9$; and
  vi) —(CH$_2$)$_r$NR$^8$C(NR$^8$)NR$^8$(CH$_2$)$_t$R$^9$;
wherein R$^8$ is hydrogen or C$_1$-C$_3$ linear alkyl; the index r is an integer from 0 to 4 and the index t is an integer form 0 to 4. R$^9$ is phenyl or naphthyl. The index c is from 1 to 100.
  L$^3$ is a linking unit. L$^3$ comprises one or more units capable of linking the disclosed Q units to the disclosed Z core units as disclosed herein. L$^3$ units can comprise an admixture of two or more units or a single unit. Non-limiting examples of units that can comprise L$^3$ units include units comprising unsaturated units, i.e., —CH═CH— and —C≡C—, saturated units, i.e., —CH$_2$—, polyethers, for example, —CH$_2$CH$_2$O—, —CH$_2$CH$_2$CH$_2$O—, —CH$_2$CH(CH$_3$)O—, —CH(CH$_3$)CH$_2$O—, and the like. Depending upon the properties of L$^3$ desired by the formulator, the L$^3$ can comprise these units in any order and in any amount.
  One aspect of Z relates to units having the formula:

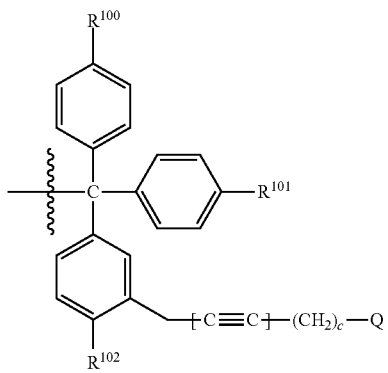

wherein R$^{100}$, R$^{101}$ and R$^{102}$ are each independently —OR$^{10}$; R$^{10}$ is C$_1$-C$_4$ alkyl, the index c is from 1 to 100, the —C≡C— unit can be inserted at any point in the linking group.

One embodiment of this aspect of Z relates to units having the formula:

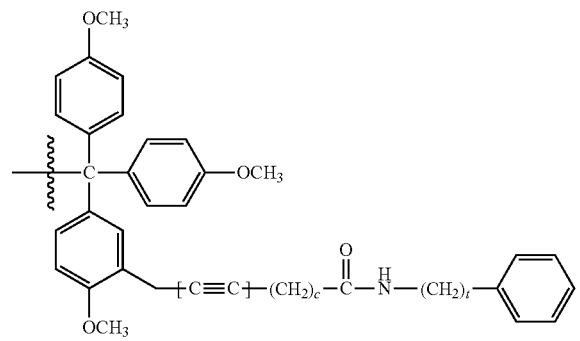

wherein the index c is from 1 to 100, the —C≡C— unit can be inserted at any point in the linking group.
  Non-limiting examples of this embodiment include:

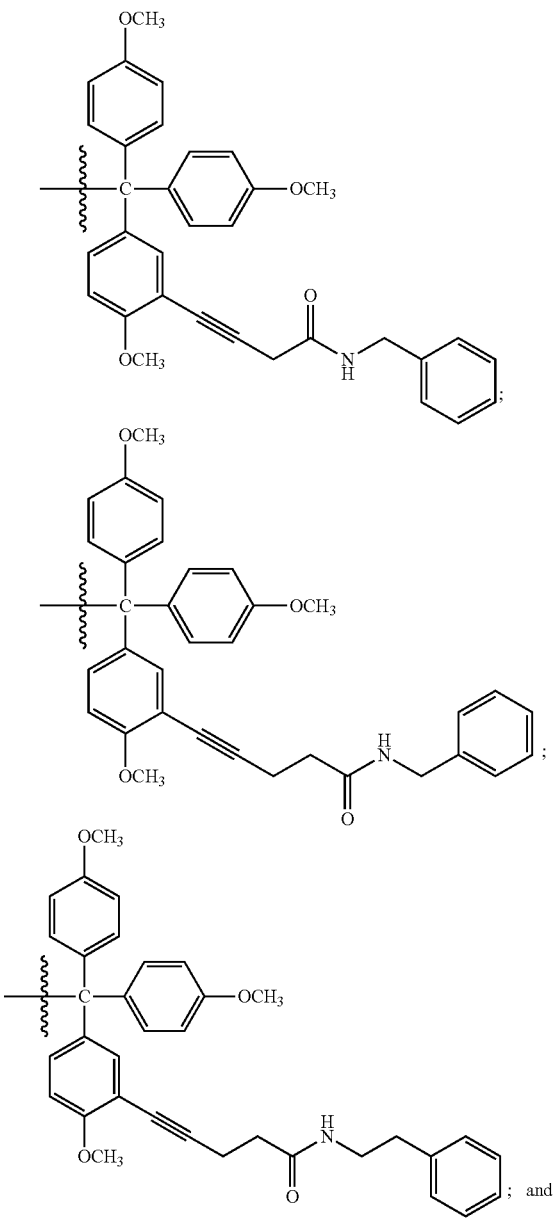

; and

-continued

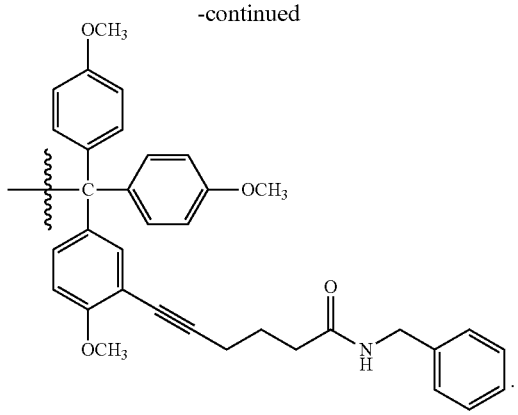

L Units

L units link the X antigen affinity portion of the imaging agents with the Z units. L units comprise a fragmentable bond that under the conditions of MALDI-MS or other mass spectrum conditions releases a stable carbocation. For one category of the imaging agents, the Z unit is released according to the following scheme:

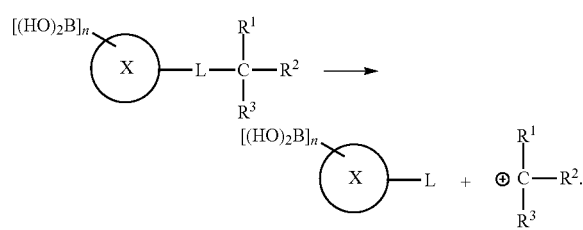

For another category of imaging agents the Z unit is released according to the following scheme:

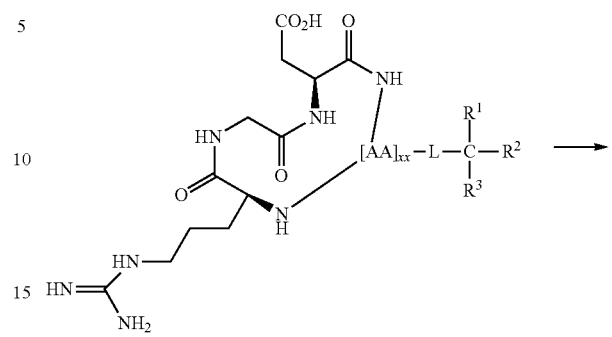

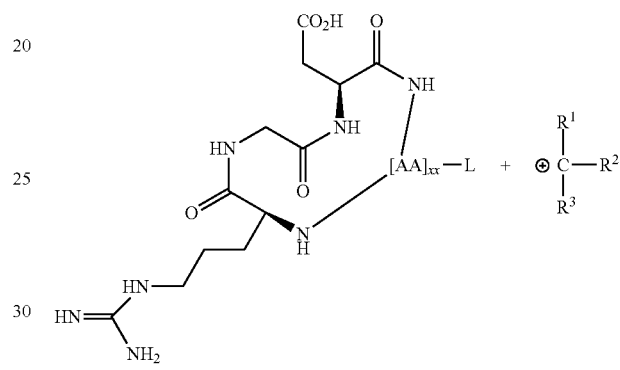

For a further category of imaging agents the Z unit is released according to the following scheme:

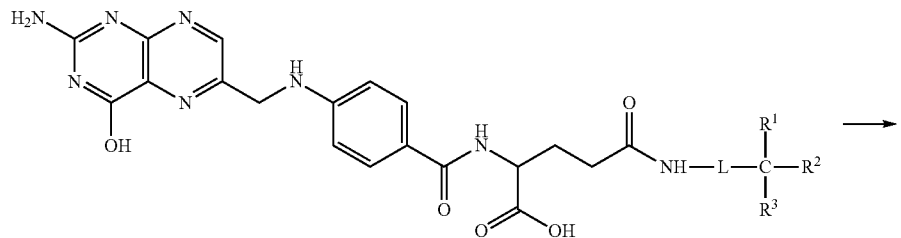

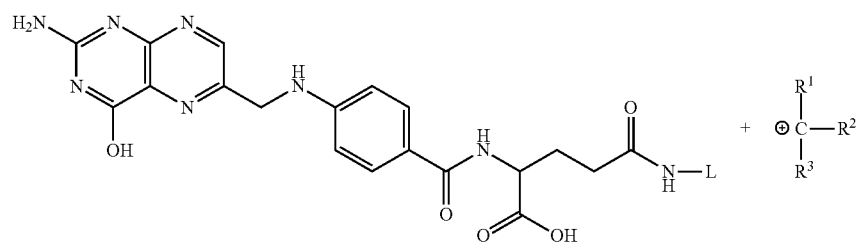

L units have the formula:

-(J)$_d$(CH$_2$)$_e$(K)$_f$(CH$_2$)$_g$(L)$_h$(CH$_2$)$_i$(M)$_j$-;

-(J)$_d$(OCH$_2$CH$_2$)$_e$(K)$_f$(OCH$_2$CH$_2$)$_g$(L)$_h$(OCH$_2$CH$_2$)$_i$(M)$_j$-;

-(J)$_d$(CH$_2$)$_e$(K)$_f$(OCH$_2$CH$_2$)$_g$(L)$_h$(CH$_2$)$_i$(M)$_j$-; or

-(J)$_d$(OCH$_2$CH$_2$)$_e$(K)$_f$(CH$_2$)$_g$(L)$_h$(OCH$_2$CH$_2$)$_i$(M)$_j$-;

wherein J, K, L and M are each independently chosen from one or more:
  i) —(CH$_2$)$_{yy}$O(CH$_2$)$_{zz}$—;
  ii) —(CH$_2$)$_{yy}$NH(CH$_2$)$_{zz}$—;
  iii) —(CH$_2$)$_{yy}$S(CH$_2$)$_{zz}$—;
  iv) —(CH$_2$)$_{yy}$C(O)(CH$_2$)$_{zz}$—
  v) —(CH$_2$)$_{yy}$OC(O)(CH$_2$)$_{zz}$—;
  vi) —(CH$_2$)$_{yy}$C(O)O(CH$_2$)$_{zz}$—;
  vii) —(CH$_2$)$_{yy}$NHC(O)(CH$_2$)$_{zz}$—;
  viii) —(CH$_2$)$_{yy}$C(O)NH(CH$_2$)$_{zz}$—;
  ix) —(CH$_2$)$_{yy}$NHC(O)NH(CH$_2$)$_{zz}$—;
  x) —(CH$_2$)$_{yy}$C(S)(CH$_2$)$_{zz}$—;
  xi) —(CH$_2$)$_{yy}$NHC(S)(CH$_2$)$_{zz}$—
  xii) —(CH$_2$)$_{yy}$C(S)NH(CH$_2$)$_{zz}$—;
  xiii) —(CH$_2$)$_{yy}$NHC(S)NH(CH$_2$)$_{zz}$—;
  xiv) $C_3$-$C_{10}$ carbocyclic rings;
  xv) aryl rings chosen from phenyl and napthyl;
  xvi) heterocyclic rings comprising from 1 to 4 heteroatoms chosen from nitrogen (N), oxygen (O) and sulfur (S); and
  xvii) heteroaryl rings comprising from 1 to 4 heteroatoms chosen from nitrogen (N), oxygen (O) and sulfur (S); and
  xviii) any combination thereof for each of J, K, L and M;

the indices d, f, h and j are 0 or 1. When J is absent the index d is equal to 0, when J is present the index d is equal to 1. When K is absent the index f is equal to 0, when K is present the index f is equal to 1. When L is absent the index h is equal to 0, when L is present the index h is equal to 1. When M is absent the index j is equal to 0, when M is present the index j is equal to 1. The indices e, g and i are independently integers from 0 to 10. The index yy is an integer from 0 to 5. The index zz is an integer from 0 to 5.

The disclosed linking units L can be assembled prior to attachment to the X and Z units or can be assemble as a part of the linking process itself. One aspect of the formation of liking units relates to the use of a reaction which forms a 1,2,3-triazolyl ring as one step in forming the linking unit, for example, according to the following scheme:

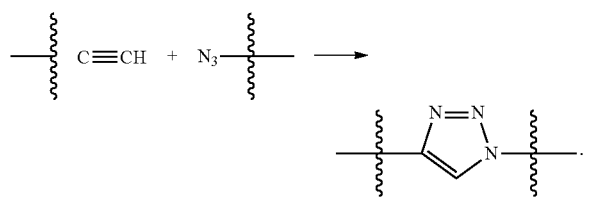

The following embodiment of linking units L comprise one or more 1,2,3-triazolyl rings:

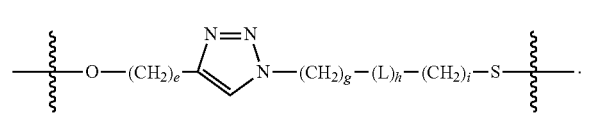

One iteration of this embodiment relates to units having the formula:

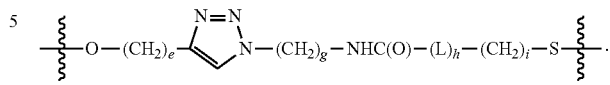

Non-limiting examples of this iteration include:

i)
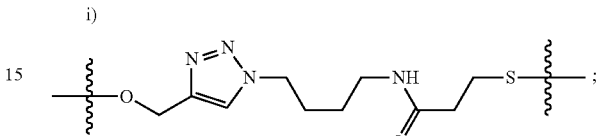

ii)
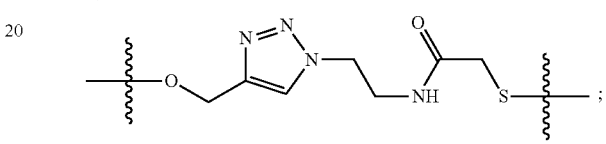

iii)
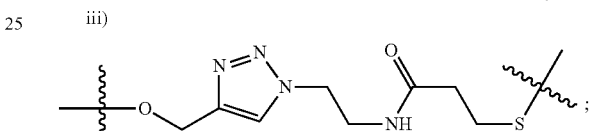

iv)
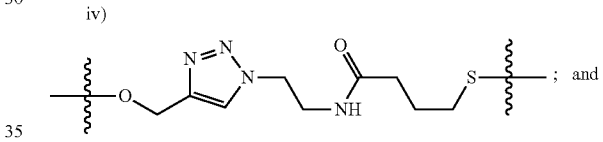; and v)
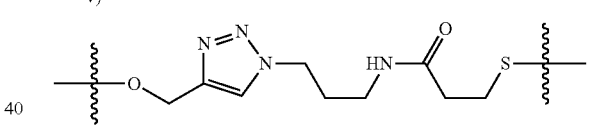.

Another iteration of this embodiment relates to units having the formula:

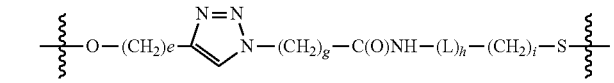

Non-limiting examples of this iteration include:

i)
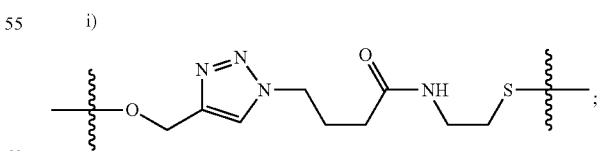

ii)
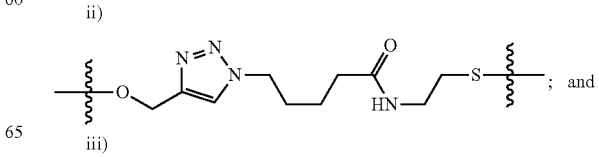; and iii)

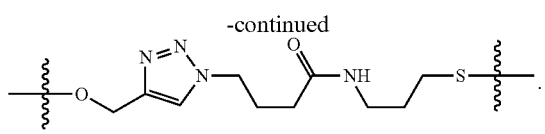

Another embodiment relates to linking units L comprise one or more 1,2,3-triazolyl rings fused to second ring:

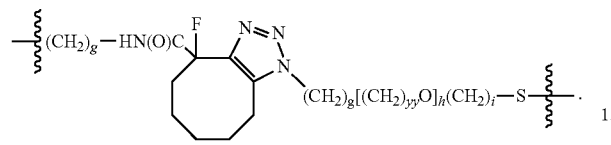

wherein K is a 4,5,6,7,8,9-hexahydro-1H-cycloocta[d][1,2,3]triazolyl ring.

One embodiment of L units relates to L units having the formula:

-(J)$_d$(OCH$_2$CH$_2$)$_e$(K)$_f$(OCH$_2$CH$_2$)$_g$(L)$_h$(OCH$_2$CH$_2$)$_i$(M)$_j$-;

non-limiting examples of which include:
i) —C(O)CH$_2$(OCH$_2$CH$_2$)$_3$NHC(O)CH$_2$(OCH$_2$CH$_2$)$_3$NHC(O)(CH$_2$)$_2$S—;
ii) —C(O)CH$_2$(OCH$_2$CH$_2$)$_3$NHC(O)CH$_2$(OCH$_2$CH$_2$)$_3$NHC(O)(CH$_2$)$_2$S —;
iii) —C(O)CH$_2$(OCH$_2$CH$_2$)$_4$NHC(O)CH$_2$(OCH$_2$CH$_2$)$_4$NHC(O)(CH$_2$)$_2$S —;
iv) —C(O)CH$_2$(OCH$_2$CH$_2$)$_2$C(O)NHCH$_2$(OCH$_2$CH$_2$)$_2$NHC(O)(CH$_2$)$_2$S—;
v) —C(O)CH$_2$(OCH$_2$CH$_2$)$_3$C(O)NHCH$_2$(OCH$_2$CH$_2$)$_3$NHC(O)(CH$_2$)$_2$S —; and
vi) —C(O)CH$_2$(OCH$_2$CH$_2$)$_4$C(O)NHCH$_2$(OCH$_2$CH$_2$)$_4$NHC(O)(CH$_2$)$_2$S—.

The disclosed imaging agents can be prepared in any manner convenient to the formulator, for example, a convergent synthesis, a linear synthesis or mixtures thereof. Disclosed herein below is a non-limiting example of a procedure for preparing the disclosed imaging agents.

Preparation of Imaging Agents According to the Disclosure
Preparation of a Carbocation Reporter Precursor Scheme I

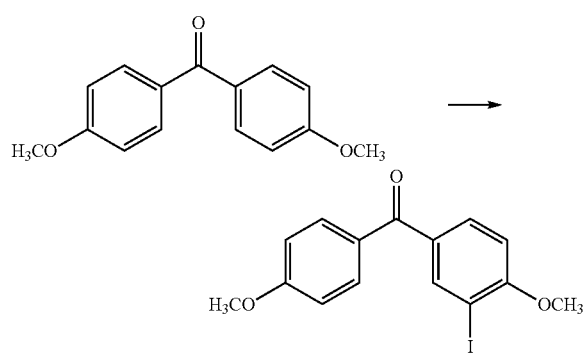

Reagents and conditions: (a) I$_2$, HNO$_3$, dioxane, H$_2$O; 60° C.

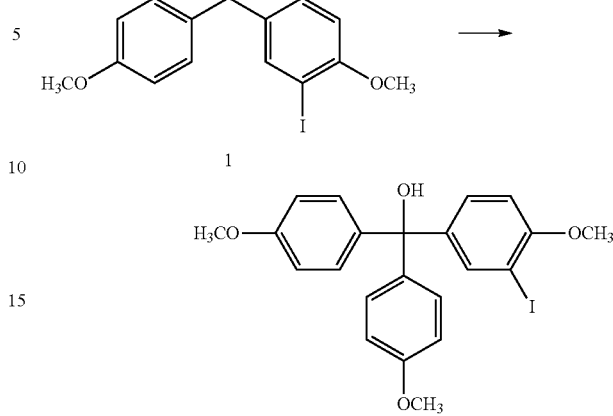

Reagents and conditions: (b) 4-methoxyphenylmagnesium bromide, THF; rt

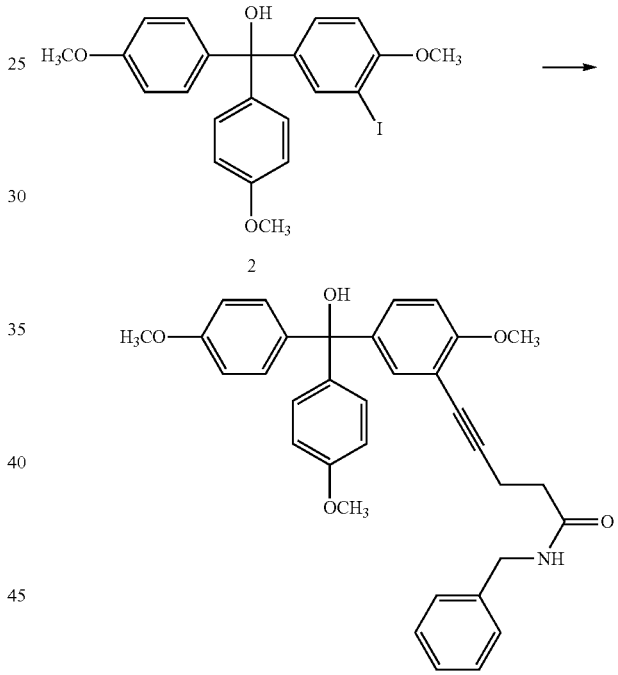

Reagents and conditions: (c) N-benzyl pentynoic amide, DMF, CuI, Et$_3$N, Pd(PPh$_3$)$_4$; rt

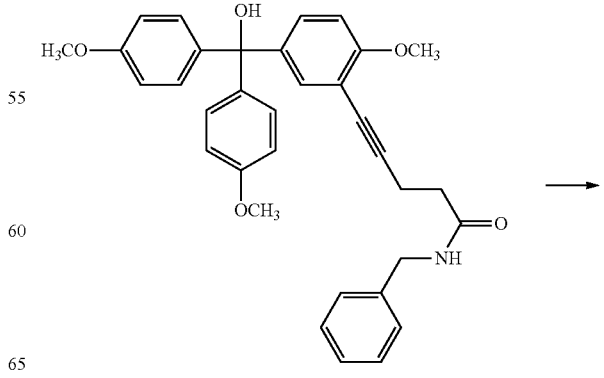

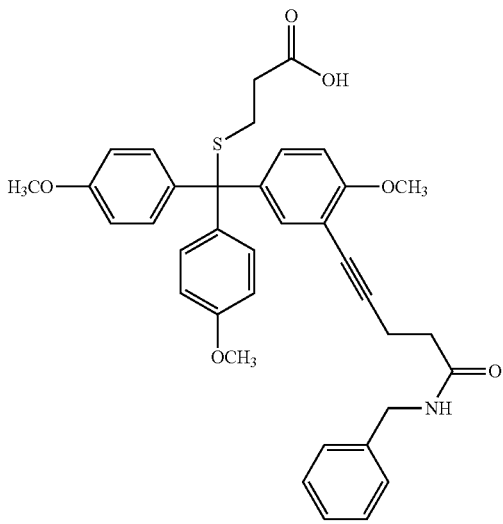

4

Reagents and conditions: (d) mercaptopropionic acid, TFA, CH₂Cl₂; rt

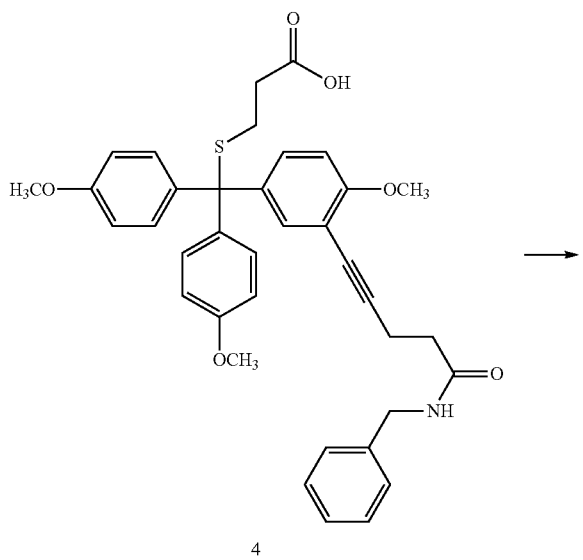

4

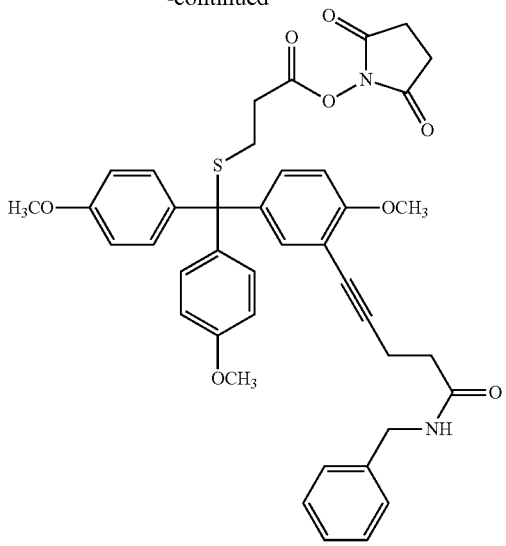

5

Reagents and conditions: (e) EDCI, N-hydroxysuccinimide, CH₂Cl₂; rt

Example 1

2,5-Dioxopyrrolidin-1-yl 3-[({3-[5-(benzylamino)-5-oxopent-1-yn-1-yl]-4-methoxyphenyl}bis{4-methoxyphenyl}methyl)thio]propanoate (5)

Preparation of (3-iodo-4-methoxyphenyl)(4-methoxyphenyl)methanone (1): To a solution of 4,4'-dimethoxybenzophenone (1.8 g, 7.5 mmol) in dioxane (10 mL), iodine (1.0 g, 3.9 mmol) was added in at 60° C. After the mixture was stirred for 15 min, water (2 mL) was added followed by the addition of 58% HNO₃ (4.1 mL) in a drop wise fashion within 1 hour. The reaction was keep stirring at 60° C. for about 6 hours until iodine color disappeared. Nitrogen was bubbled through the reaction mixture until no more brown gas emitted, and the mixture was diluted with water (100 mL) to afford pale yellow precipitates, which were collected and washed with 5% NaHCO₃ aqueous solution and water. Re-crystallization from EtOH (20 mL), followed by column chromatography purification with hexane/EtOAc (10:1) gave white needles (1.1 g, 40% yield). $^1$H NMR (DMSO-d₆): 8.11 (s, 1H), 7.73 (m, 3H), 7.12 (m, 3H), 3.95 (s, 3H), and 3.87 (s, 3H) ppm. MS-ESI: [M+H]⁺ (m/z, 369.0).

Preparation of (3-iodo-4-methoxyhenyl)bis(4-methoxyphenyl)methanol (2): To a solution of (3-iodo-4-methoxyphenyl)(4-methoxyphenyl)methanone (1) (1.0 g, 2.7 mmol) in dry THF (20 mL), 1M solution of 4-methoxyphenylmagnesium bromide in THF (5.5 ml, 5.5 mmol) was added in one portion at 0° C. After stirring at RT overnight, the reaction solution was diluted with 150 mL of saturated NaHCO₃ solution and extracted with EtOAc (50 mL×3). The EtOAc layer was washed with water and brine, dried over anhydrous Na₂SO₄, filtered and concentrated under reduced pressure. The residue was purified by flash chromatography with hexane/EtOAc (10:1) to give white crystals (1.2 g, 90% yield). $^1$H NMR (CDCl₃): 7.77 (s, 1H), 7.16 (m, 5H), 6.87 (m, 4H), 6.74 (d, J=5.6 Hz 1H), 3.89 (s, 3H), and 3.82 (s, 3H) ppm. MS-ESI: [M+H]⁺ (m/z, 477.3).

Preparation of N-benzyl-5-{5-[hydroxybis(4-methoxyphenyl)methyl]-2-methoxy-phenyl}pent-4-ynamide (3): To a solution of (3-iodo-4-methoxyhenyl)bis(4-methoxy-phenyl)methanol (2) (530 mg, 1.11 mmol) and N-benzyl pentynoic amide (219 mg, 1.17 mmol) in DMF (6 mL), Pd(PPh$_3$)$_4$ (116 mg, 0.1 mmol), CuI (38 mg, 0.2 mmol), and Et$_3$N (235 uL, 1.68 mmol) were added in sequence under N$_2$ protection. The reaction mixture was stirred at room temperature overnight, then diluted with water (100 mL) and extracted with EtOAc (60 mL×3). The EtOAc extract was washed with water (50 mL), 0.1 M solution of (NH$_4$)$_2$EDTA (50 mL), and brine (50 mL), dried over anhydrous Na$_2$SO$_4$, filtered and concentrated under reduced pressure. The residue was purified on a silica gel column with hexane/EtOAc 1:1 as the solvent to give a white solid (400 mg, 67% yield). $^1$H NMR (CD$_3$OD): 7.24 (dd, J=3.6, 0.8 Hz, 2H), 7.14 (m, 5H), 7.08 (m, 4H), 6.97 (dd, J=6.8, 2.0 Hz, 1H), 6.81 (m, 4H), 4.34 (s, 2H), 3.79 (s, 3H), 3.76 (s, 6H), 2.72 (t, J=6.8 Hz, 2H), and 2.48 (t, J=6.8 Hz, 2H) ppm. MS-ESI: [M+H]$^+$ (m/z, 536.4).

Preparation of 3-[({3-[5-(benzylamino)-5-oxopent-1-yn-1-yl]-4-methoxyphenyl}-bis{4-methoxyphenyl}methyl)thio]propanoic acid (4): To a solution of N-benzyl-5-{5-[hydroxybis(4-methoxyphenyl)methyl]-2-methoxyphenyl}pent-4-ynamide (3) (340 mg, 0.64 mmol) in 6 mL of CH$_2$Cl$_2$ under N$_2$ were added 3-mercaptopropionic acid (56 μL, 0.64 mmol) and TFA (67 μL, 0.83 mmol). The mixture was stirred at RT for 2 h. At that point, TLC indicated that the starting material was consumed. The volatiles in the reaction solution were removed under vacuum. The residue was purified by silica gel chromatography with CH$_2$Cl$_2$/MeOH (10:1) to give a colorless needle-like product (248 mg, 62% yield). $^1$H NMR (CDCl$_3$): 7.64 (d, J=2.2 Hz, 1H), 7.27-7.11 (m, 10H), 6.78 (d, J=8.8 Hz, 4H), 6.71 (d, J=8.8 Hz, 1H), 6.50 (brs, 1H), 4.45 (d, J=5.6 Hz, 2H), 3.77 (s, 6H), 3.72 (s, 3H), 2.77 (t, J=6.8 Hz, 2H); 2.52 (t, J=6.6 Hz, 2H); 2.40 (t, J=6.8 Hz, 2H), 2.29 (t, J=6.8 Hz, 2H) ppm. MS-ESI: [M+H]$^+$ (m/z, 624.0).

Preparation of 2,5-dioxopyrrolidin-1-yl 3-[({3-[5-(benzylamino)-5-oxopent-1-yn-1-yl]-4-methoxyphenyl}bis{4-methoxyphenyl}methyl)thio]propanoate (5): 3-[({3-[5-(benzylamino)-5-oxopent-1-yn-1-yl]-4-methoxyphenyl}-bis{4-methoxyphenyl}methyl)-thio]propanoic acid (4) (248 mg, 0.4 mmol) and N-hydroxysuccinimide (46 mg, 0.4 mmol) were dissolved in 8 mL of CH$_2$Cl$_2$. Then 1-ethyl-3-(3-dimethylaminopropyl)carbodiimide (EDCI) (77 mg, 0.4 mmol) was added at RT with stirring. After stirring at RT for 3 h, the reaction solution was diluted with CH$_2$Cl$_2$ (60 mL), washed with water (5 mL) and brine (5 mL), dried over anhydrous Na$_2$SO$_4$, filtered and concentrated under reduced pressure. The residue was purified by silica gel chromatography with CH$_2$Cl$_2$/MeOH (20:1) to give a white solid (204 mg, 72% yield). $^1$H NMR (CDCl$_3$): 7.43 (d, J=2.5 Hz, 1H), 7.26 (m, 5H); 7.22 (m, 5H); 6.82 (m, 4H); 6.46 (brs, 1H); 3.80 (s, 6H); 3.74 (s, 3H); 2.78 (m, 6H); 2.53 (m, 4H); 2.47 (m, 2H) ppm. MS-ESI: [M+H]$^+$ (m/z, 721.2).

Preparation of an Antigen Affinity Unit

Scheme II

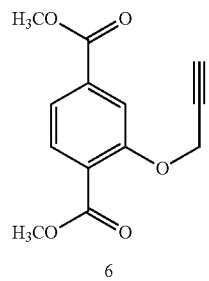

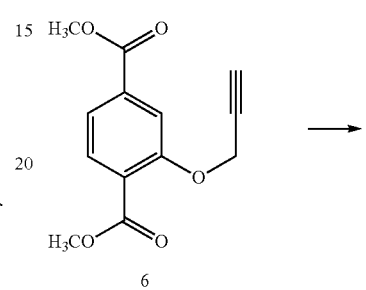

Reagents and conditions: (a) propargyl bromide, K$_2$CO$_3$, CH$_3$CN, reflux 24 hr.

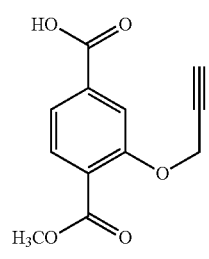

Reagents and conditions: (b) NaOH, CH$_3$OH, reflux 3 hr.

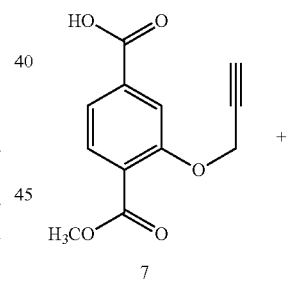

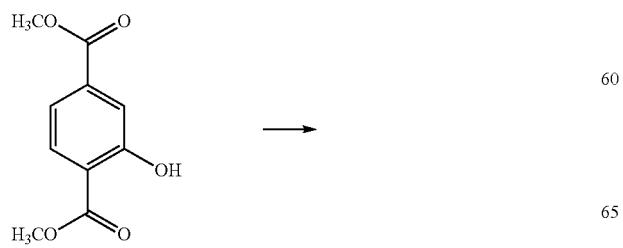

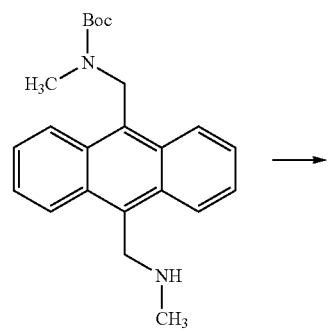

-continued
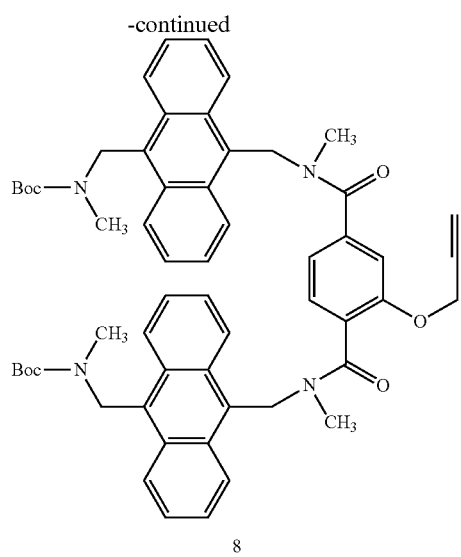
8
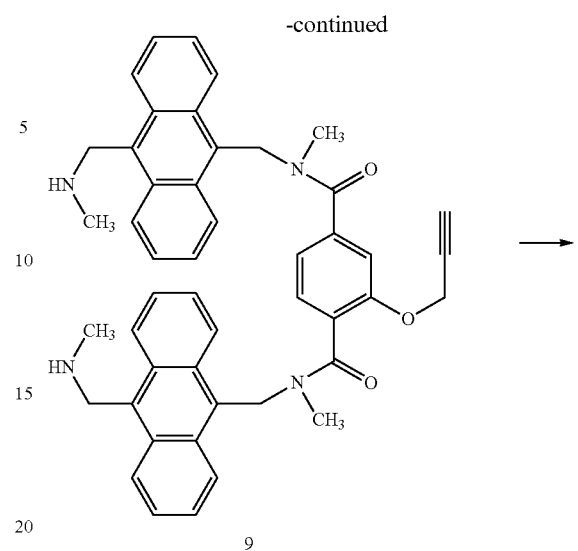
9
Reagents and conditions: (c) CH₂Cl₂, EDCI, HOBt, DMAP, rt 18 hr.
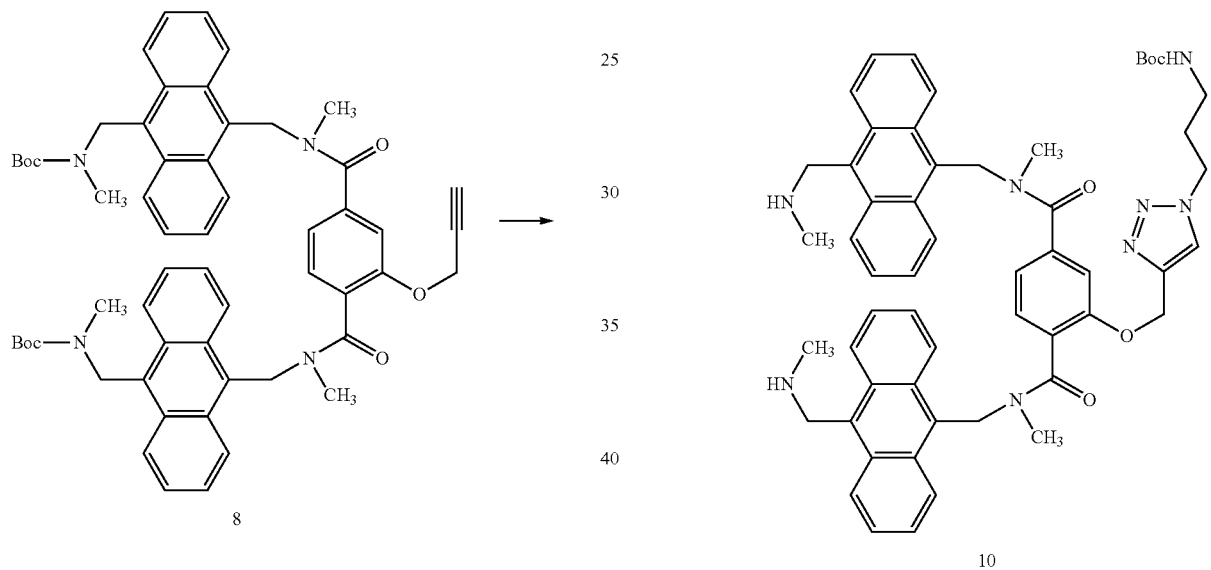
8
9
Reagents and conditions: (d) TFA, CH₂Cl₂, 3 hr.
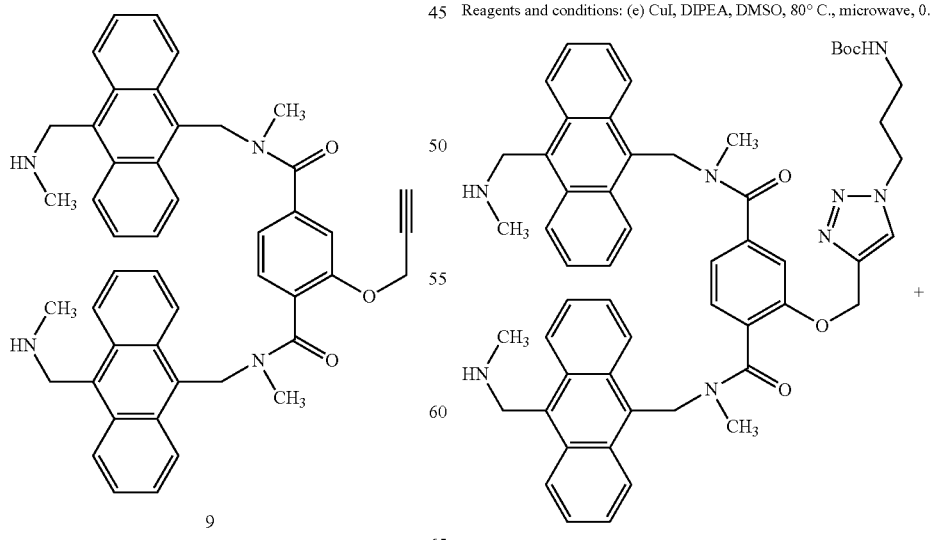
10
Reagents and conditions: (e) CuI, DIPEA, DMSO, 80° C., microwave, 0.5 hr.
10

-continued

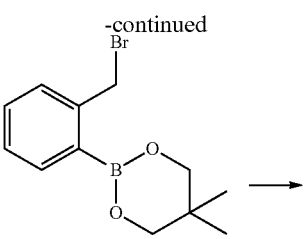

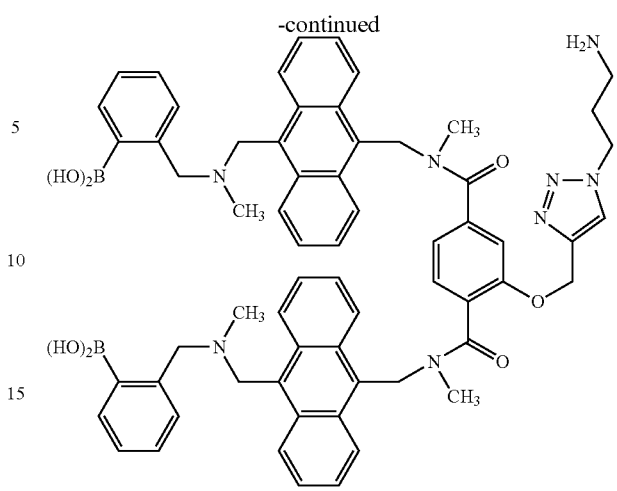

12

Reagents and Conditions: (g) TFA, CH₂Cl₂, rt 4 hr.

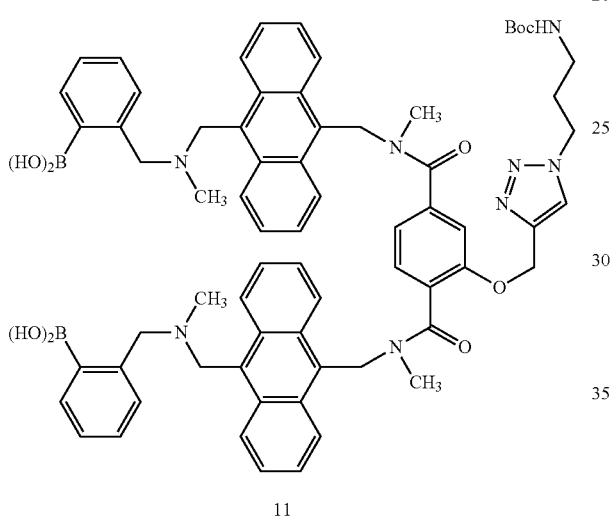

11

Reagents and conditions: (f) K₂CO₃, NaI, CH₃CN.

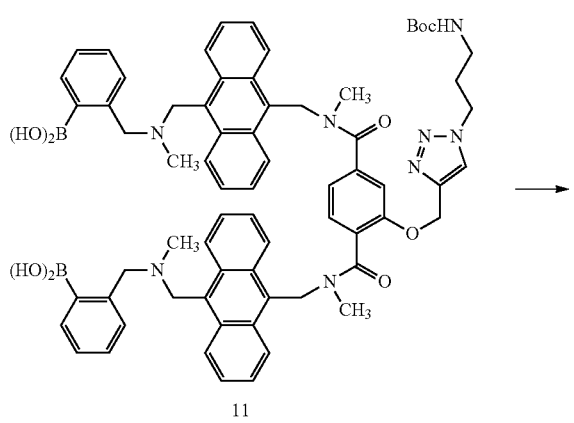

11

Example 2

({[({[({2-[(1-{3-Aminopropyl}-1H-1,2,3-triazol-4-yl)methoxy]-terephthaloyl}bis(methylazanediyl))bis(methylene)]bis(anthracene-10,9-diyl)}bis-(methylene))bis(methylazanediyl)]bis(methylene)}bis(2,1-phenylene))-diboronic acid (12)

Preparation of dimethyl 2-prop-2-yn-1-yloxy)terephthalate (6): To a solution of dimethyl 2-hydroxyterephthalate (24 g, 114 mmol) in 250 mL of CH₃CN was added K₂CO₃ (18.9 g, 137 mmol) and propargyl bromide (16.38 mL, 137 mmol). The reaction mixture was refluxed for 24 hours under nitrogen. After cooling down to room temperature, the reaction mixture was then poured into a mixture of EtOAc (100 mL) and 10% HCl aqueous solution (10 mL). The organic phase was separated and washed with saturated NaHCO₃, brine and dried over anhydrous Na₂SO₄. Removal of the solvent provided a wax-like light white solid (28.25 g, quantitative yield): $^1$H NMR (CDCl₃) δ7.84-7.82 (m, 1H), 7.71-7.69 (m, 1H), 7.782-7.779 (m, 1H), 4.85 (d, J=2.0 Hz, 2H), 3.95 (s, 3H), 3.92 (s, 3H), 2.56 (t, J=2.0 Hz, 1H). $^{13}$C NMR (CDCl₃) δ166.0, 165.9, 156.6, 134.3, 131.6, 125.2, 122.3, 115.1, 77.6, 76.5, 56.9, 52.5, 52.4. MS (+ESI) m/z 249.1 [M+H]⁺.

Preparation of 1-(prop-2-yn-1-yloxy)terephthalic acid (7): To a solution of dimethyl 2-prop-2-yn-1-yloxy)terephthalate (6) (3.0 g, 143 mmol) in 15 mL of CH₃OH was added 25 mL of sodium hydroxide solution (2M), and the reaction mixture was refluxed for 3 hours. After removal of the solvent by vacuum, the residue was acidified to pH 2 with 10% HCl solution. The resulting solid was collected, washed with water, dried on vacuum to afford the desired product as a white solid (2.11 g, 84%): $^1$H NMR (DMSO-d₆) δ 13.22 (brs, 2H), 7.71-7.73 (m, 2H), 7.61-7.63 (m, 1H), 4.96 (d, J=2 Hz, 3H), 3.65 (s, 1H); $^{13}$C NMR (DMSO-d₆) δ167.3, 167.0, 155.8, 134.7, 130.9, 126.9, 122.2, 114.7, 79.4, 79.2, 56.6. MS (−ESI) m/z 219.1 [M−H]⁻.

Preparation of di-tert-butyl {[({[2-(prop-2-yn-1-yloxy)terephthaloyl]bis(methyl-azanediyl)}bis(methylene))bis(anthracene-10,9-diyl)]bis(methylene)}bis(methylcarbamate) [alternatively N¹, N⁴-Bis((9-(N-Boc-methylamino)methyl)anthracen-10-yl)methyl)-N¹, N⁴-dimethyl-2-(prop-2-ynyloxy)terephthalamide](8): To a solution of tert-butyl methyl ({10-[(methylamino)methyl]anthracen-9-yl}methyl)carbamate (1.62 g, 4.4 mmol) and 1-(prop-2-yn-1-yloxy)terephthalic acid (7) (488 mg, 2.2 mmol) in 320 mL of dried $CH_2Cl_2$ was added 1-Ethyl-3-(3-dimethylaminopropyl)carbodiimide (EDCI) (820 mg, 9.0 mmol), 1-hydroxybenzotriazole (HOBt) (1.2 g, 8.9 mmol) and dimethylaminopyridine (DMAP) (108 mg, 0.9 mmol). After stirring overnight at room temperature under nitrogen atmosphere, the reaction mixture was washed with water and dried over $MgSO_4$. After removal of the solvent, the residue was purified by silica gel chromatography ($CH_2Cl_2/CH_3OH$ 100/1) to afford the desired product as a light yellow powder (1.76 g, 88%): $^1H$ NMR ($CDCl_3$) δ8.50 (s, 8H), 7.58 (s, 8H), 7.28 (s, 1H), 7.12 (s, 1H), 7.02 (s, 1H), 5.86 (s, 4H), 5.55 (s, 4H), 4.55 (s, 2H), 2.54 (s, 3H), 2.51 (s, 6H), 2.32 (s, 3H), 1.57 (s, 18H); $^{13}C$ NMR ($CDCl_3$) δ170.3, 168.0, 153.2, 138.1, 130.9, 130.8, 130.1, 128.4, 128.1, 128.04, 126.2, 126.0, 125.9, 125.0, 124.5, 124.2, 120.2, 111.4, 79.8, 77.5, 76.1, 55.8, 53.3, 41.4, 38.5, 35.5, 33.9, 28.4. HRMS (+ESI): Calc. for $[C_{57}H_{61}N_4O_7]^+$ $[M+H]^+$ m/z 913.4540. Found 913.4566. MS (+ESI) m/z: 913.4 $[M+H]^+$.

Preparation of $N^1,N^4$-Dimethyl-$N^1,N^4$-bis({9-[(methylamino)methyl]anthracen-10-yl}methyl)-2-(prop-2-ynyloxy) terephthalamide (9): A mixture of compound di-tert-butyl {[({[2-(prop-2-yn-1-yloxy)terephthaloyl]bis(methylazanediyl)}bis(methylene))-bis(anthracene-10,9-diyl)]bis (methylene)}bis(methylcarbamate) (8) (1.0 g, 1.1 mmol) and trifluoroacetic acid (TFA) (3 mL) in 12 mL of $CH_2Cl_2$ was stirred at room temperature in the dark for 3 hours. After removal of solvent, a mixed solvent of EtOAc/hexane 1:1 (20 mL) was added to the residue. A precipitate was generated and the solid was collected, washed with saturated $NaHCO_3$ solution and water, dried under vacuum to provide the desired product as a light yellow solid (615 mg, 82%): $^1H$ NMR ($CDCl_3$) δ 8.43-8.39 (m, 8H), 7.57-7.52 (m, 8H), 7.29-7.26 (m, 1H), 7.09 (s, 1H), 6.99-6.97 (m, 1H), 5.83-5.78 (m, 4H), 4.69 (s, 4H), 4.53 (s, 2H), 2.69 (s, 6H), 2.51 (s, 3H), 2.39 (s, 3H), 2.33 (s, 1H), 1.94 (s, 2H). $^{13}C$ NMR ($CDCl_3$) δ 170.9, 168.6, 153.7, 138.6, 133.5, 131.6, 131.5, 130.5, 128.6, 128.0, 126.7, 126.5, 126.3, 125.5, 125.4, 125.4, 125.0, 124.7, 120.7, 111.9, 78.1, 76.8, 56.4, 48.5, 42.4, 41.9, 37.6, 36.1, 34.5. HRMS (+ESI): Calc. for $[C_{47}H_{45}N_4O_3]^+$ $[M+H]^+$ m/z 713.3492. Found 713.3512. MS (−ESI) m/z 711.4 $[M−H]^−$.

Preparation of tert-butyl {3-[4({2,5-bis[methyl({10-[(methylamino)methyl]-anthracene-9-yl}methyl)carbamoyl]phenoxy}methyl)-1H-1,2,3-triazol-1-yl]propyl}-carbamate (10): To a mixture of $N^1,N^4$-Dimethyl-$N^1,N^4$-bis({9-[(methylamino)methyl]-anthracene-10-yl}methyl)-2-(prop-2-ynyloxy)terephthalamide (9) (105 mg, 0.14 mmol) and tert-butyl (3-azidopropyl)carbamate (84 mg, 0.42 mmol) in 0.5 mL of dimethylsulfoxide (DMSO) was added diisopropylethylamine (DIPEA) (0.12 mL, 0.7 mmol) and CuI (11 mg, 0.056 mmol). The reaction mixture was microwave-irradiated at 80° C. for 30 minutes under nitrogen atmosphere. To the reaction mixture, water was slowly added in (5 mL). Then the mixture was extracted with $CH_2Cl_2$. The combined $CH_2Cl_2$ phase was washed with brine and dried over $MgSO_4$. The solvent was removed under vacuum and the residue was purified by silica gel chromatography ($CH_2Cl_2/CH_3OH$ 10/3) to provide a light yellow solid (130 mg, 97%). $^1H$ NMR ($CDCl_3$) δ8.44-8.43 (m, 8H), 7.58-7.53 (m, 9H), 7.08-6.96 (m, 3H), 5.87-5.69 (m, 4H), 5.10 (s, 2H), 4.76 (s, 4H), 4.20 (s, 2H), 2.94 (s, 2H), 2.84 (s, 6H), 2.40 (s, 6H), 1.78 (s, 2H), 1.44 (s, 9H); MS (ESI) m/z 913.4 $[M+H]^+$ Preparation of ({[({[({2-[(1-{3-[(tert-butoxycarbonyl) amino]propyl}-1H-1,2,3-triazol-4-yl)methoxy] terephthaloyl}bis(methylazanediyl))bis(methylene)]bis(anthracene-10,9-diyl)}bis(methylene))bis(methylazanediyl)] bis(methylene)}bis(2,1-phenylene))-diboronic acid (11): To a solution of tert-butyl {3-[4({2,5-bis[methyl({10-[(methylamino)-methyl]anthracene-9-yl}methyl)carbamoyl] phenoxy}methyl)-1H-1,2,3-triazol-1-yl]propyl}-carbamate (10) (200 mg, 0.11 mmol) in 12 mL of $CH_3CN$ were added 2-[2-(bromomethyl)-phenyl]-5,5-dimethyl-1,3,2-dioxaborinane (124 mg, 0.44 mmol), $K_2CO_3$ (152 mg, 1.1 mmol), and NaI (4 mg, 0.022 mmol). The reaction mixture was stirred at room temperature for 16 hours under nitrogen atmosphere in the dark. After filtering out the solid, the organic solvent was removed, and the residue was re-dissolved in $CH_2Cl_2$, washed with 5% $NaHCO_3$ solution and brine, and dried over $MgSO_4$. Solvent evaporation gave a crude product, which was re-crystallized with $CH_2Cl_2/Et_2O$ to provide a light yellow solid (205 mg, 79% yield). $^1H$ NMR (DMSO-$d_6$) δ 6.80-9.15 (m, 28H), 5.60-5.85 (m, 4H), 5.15 (s, 2H), 4.53 (s, 4H), 4.25 (s, 2H), 3.95 (s, 4H), 3.31 (s, 6H), 2.46 (s, 6H), 2.31 (s, 2H), 1.34 (s, 9H). MS (ESI): m/z 1163.3 $[M−H_2O+H]^+$. HRMS (ESI): Calc. for $[C_{69}H_{73}B_2N_8O_8]^+$ $[M−H_2O+H]^+$ m/z 1163.5737. Found 1163.5760.

Preparation of ({[({[({2-[(1-{3-aminopropyl}-1H-1,2,3-triazol-4-yl)methoxy]-terephthaloyl}bis(methylazanediyl)) bis(methylene)]bis(anthracene-10,9-diyl)}bis-(methylene)) bis(methylazanediyl)]bis(methylene)}bis(2,1-phenylene))-diboronic acid (12): A mixture of ({[({[({2-[(1-{3-[(tert-butoxycarbonyl)amino]propyl}-1H-1,2,3-triazol-4-yl) methoxy]terephthaloyl}bis(methylazanediyl))bis (methylene)]bis(anthracene-10,9-diyl)}bis(methylene))bis (methylazanediyl)]bis(methylene)}bis(2,1-phenylene))-diboronic acid (11) (240 mg, 0.2 mmol) and trifluoroacetic acid (1.0 mL) in 10 mL of $CH_2Cl_2$ was stirred for 4 hours at room temperature under nitrogen atmosphere in the dark. After removal of solvent, the residual oil was dissolved in 3 mL of EtOAc. This was followed by the slow addition of 50 mL of $Et_2O$. The precipitate was collected and washed with saturated $K_2CO_3$ solution and water. Further purification by flash chromatography provided a white solid (133 mg, 73%): $^1H$ NMR (DMSO-$d_6$) δ6.80-9.40 (m, 30H), 4.40-6.00 (m, 12H), 3.40 (s, 6H), 3.17-3.10 (m, 2H), 2.82-2.74 (m, 2H), 2.39 (s, 6H). $^{13}C$ NMR (DMSO-d) δ: 158.9, 158.6, 136.2, 130.9, 130.6, 127.6, 127.0, 126.8, 125.5, 125.0, 119.0, 116.0, 67.8, 51.3, 47.1, 36.8, 28.3, 21.9, 21.7. MS (ESI) m/z 1063.4 $[M−H_2O+H]^+$, 1081.5 $[M+H]^+$. HRMS (+ESI): Calc. for $[C_{64}H_{67}B_2N_8O_7]^+$ $[M+H]^+$ m/z 1081.5319. Found 1081.5363; Calc. for $[C_{64}H_{65}B_2N_8O_6]^+$ $[M−H_2O+H]^+$ m/z 1063.5213. Found 1063.5253.

Scheme III below outlines the final steps in forming the imaging agent 13.

Scheme III
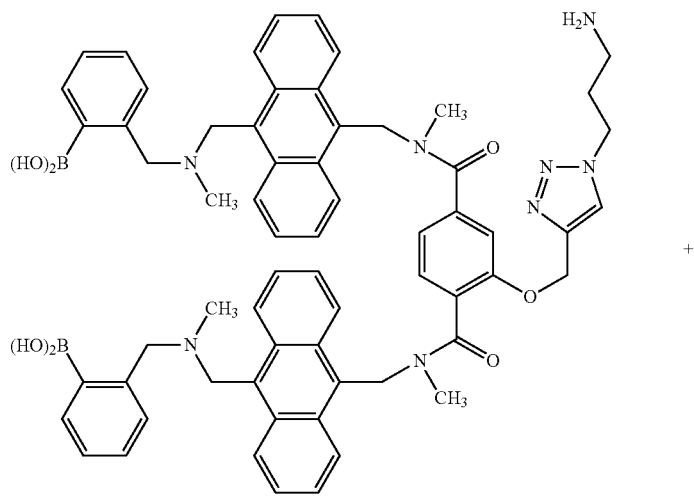
12
+
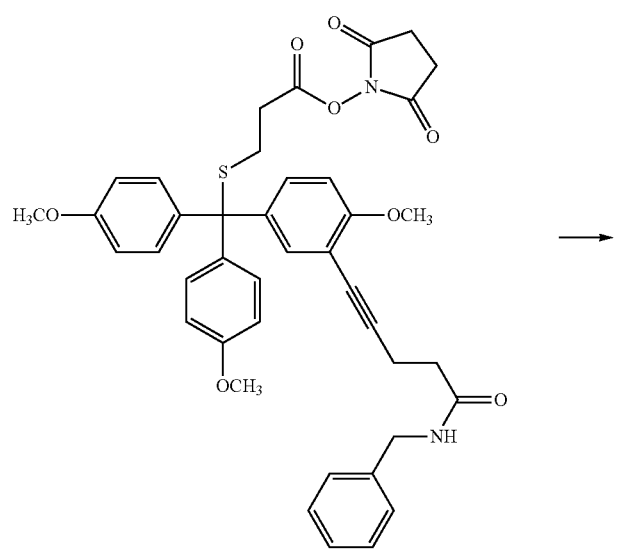
5

-continued

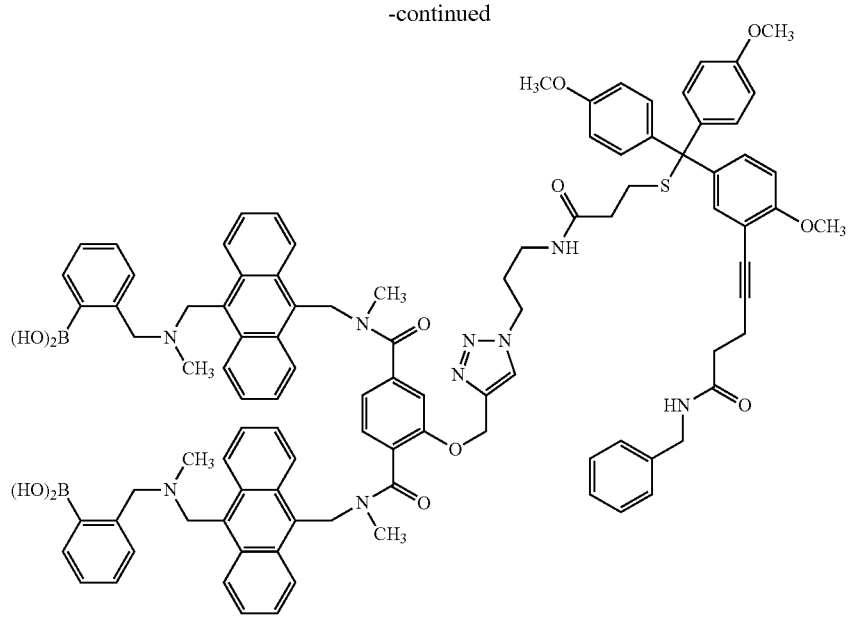

13

Reagents and conditions: (a) Et₃N, DMF, CH₂Cl₂, 18 hr.

Example 3

[({[({[({2-[(1-{3-[({3-[5-(Benzylamino)-5-oxopent-1-yn-1-yl]-4-methoxyphenyl}bis(4-methoxyphenyl)methyl)thio]propanamido}prop-3-yl)-1H-1,2,3-triazol-4-yl]methoxy}terephthaloyl)bis(methylazanediyl)]bis(methylene)}bis(anthracene-10,9-diyl))bis(methylene)]bis(methylazanediyl)}bis(methylene))bis(2,1-phenylene)]-diboronic acid (13)

Preparation of [({[({[({2-[(1-{3-[({3-[5-(benzylamino)-5-oxopent-yn-yl]-4-methoxyphenyl)bis(4-methoxyphenyl)thio]propanamido}prop-3-yl)-yl)-1H-1,2,3-triazol-4-yl]methoxy}terephthaloyl)bis(methylazanediyl)]bis(methylene)}bis(anthracene-10,9-diyl))bis(methylene)]bis(methylazanediyl)}bis(methylene))bis(2,1-phenylene)]-diboronic acid (13): In a 10-mL flask, ({[({[({2-[(1-{3-aminopropyl}-1H-1,2,3-triazol-4-yl)methoxy]-terephthaloyl}bis(methylazanediyl))bis(methylene)]bis(anthracene-10,9-diyl}bis-(methylene))bis(methylazanediyl)]bis(methylene)}bis(2,1-phenylene))-diboronic acid (12) (60 mg, 0.05 mmol) and 2,5-dioxopyrrolidin-1-yl 3-[({3-[5-(benzylamino)-5-oxopent-1-yn-1-yl]-4-methoxyphenyl}bis{4-methoxyphenyl}methyl)thio]propanoate (5) were dissolved in a mixture of dimethylformamide (DMF) (0.5 mL) and CH₂Cl₂ (1 mL). Then triethylamine (Et₃N) was added at room temperature in the dark. The mixture was stirred at room temperature overnight and then solvent was evaporated. To the resulting viscous residue was slowly added 10 mL of Et₂O to afford a suspension. The solid was filtered and washed with EtOAc to give crude product, which was purified by silica gel chromatography with CH₂Cl₂/MeOH (15:1) to give a white solid (30 mg, 36%). $^1$H NMR (DMSO-d$_6$) 9.0 (m, 3H), 8.64-8.41 (m, 9H), 7.94-6.83 (m, 32H), 5.76-5.10 (m, 5H), 4.53-4.32 (m, 2H), 4.42 (s, 3H), 3.76 (s, 3H), 3.69 (s, 6H), 3.40 (s, 12H), 3.39-3.01 (m, 18H), 2.55-2.0 (m, 8H), 1.23 (m, 2H). MS-ESI: [M−H—H₂O]⁻ (m/z, 1666.6) and [M+H—H₂O]⁺ (m/z, 1669.2).

The arginine-glycine-aspartic acid (RGD) cell adhesion sequence was discovered in fibronectin in 1984 (M. D. Pierschbacher and E. Ruoslahti, *Nature,* 1984, 309, 30-33). Proteins that contain the RGD attachment site, together with the integrins that serve as receptors for them constitute a major recognition system for cell adhesion (E. Ruoslahti, *Annu. Rev. Cell. Dev. Biol.,* 1996, 12, 697-715). The RGD sequence is the cell attachment site of a large number of adhesive extracellular matrix, blood, and cell surface proteins, and nearly half of the over 20 known integrins recognize this sequence in their adhesion protein ligands. There is a long felt need to utilize this recognition system, for example, in drug delivery and tumor targeting therapy (Z. Liu, F. Wang and X. Chen, *Theranostics,* 2011, 1, 201-210). Among all the RGD containing peptide, cRGDfK is one of the most commonly used one for recognizing a cancer-related integrin (R. Stupp and C. Ruegg, *J. Clin. Oncol.,* 2007, 25, 1637-1638). Disclosed herein in Scheme IV is the preparation of a non-limiting example of a cRGDfK-MStag conjugate according to the present disclosure.

Scheme IV
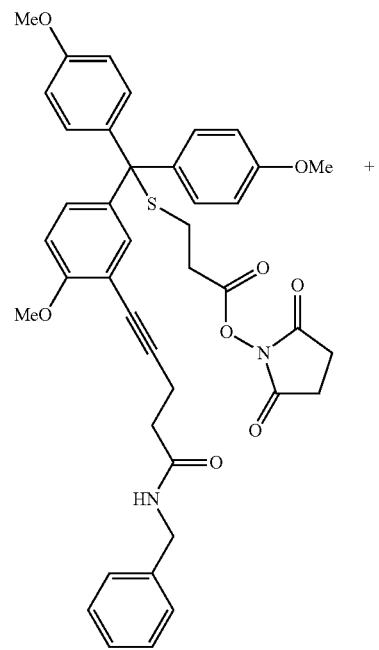
5 +
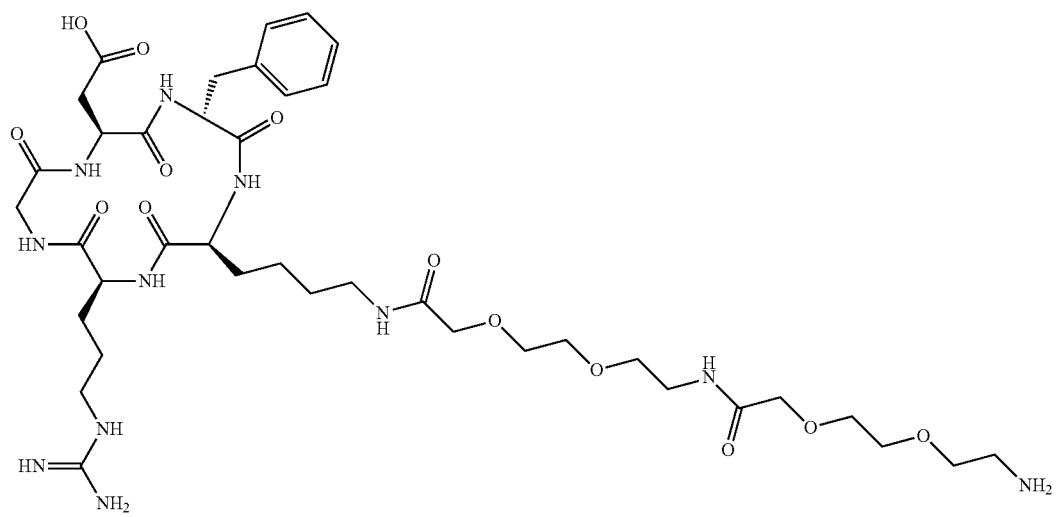

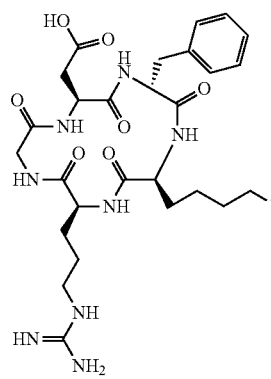

15

Example 4

2-((2S,5S,8S,11S)-5-Benzyl-8-(1-(3-(5-(benzylamino)-5-oxopent-1-yn-1-yl)-4-methoxyphenyl)-1,1-bis(4-mentoxyphenyl)-5,14,23-trioxo-9,12,18,21-tetraoxa-2-thia-6,15,24-triazaoctancosan-28-yl)-11-(3-guanidinopropyl)-3,6,9,12,15-pentaoxo-1,4,7,10,13-pentaazacyclopentadecan-2-yl)acetic acid (15)

To a solution of 2-((2S,5S,8S,11S)-8-(1-amino-8,17-dioxo-3,6,12,15-tetraoxa-9,18-diazadocosan-22-yl)-5-benzyl-11-(3-guanidinopropyl)-3,6,9,12,15-pentaoxo-1,4,7,10,13-pentaazacyclopentadecan-2-yl)acetic acid [c(RGDfK(PEG-PEG))], 14, (4 mg, 4.5 μmol) in phosphate buffer (pH 7.4) 800 μL was added 2,5-dioxopyrrolidin-1-yl 3-[({3-[5-(benzylamino)-5-oxopent-1-yn-1-yl]-4-methoxyphenyl}bis{4-methoxyphenyl}methyl)-thio]propanoate, 5, (3.6 mg, 5 μmol) in CH$_3$CN 600 μL. The resulting mixture was allowed to stir at room temperature for 12 hours, and then purified by HPLC using a Shimadzu LC-10AT VP system with a Zobax C18 reversed-phase column (21.2 mm×25 cm). The sample was eluted (6 mL/min) with a linear gradient from buffer A (0.05% TFA in H$_2$O) to buffer B (0.05% THA in acetonitrile) 5-55% B in 50 min. $^1$H NMR (CD$_3$OD): δ 7.55-7.75 (m, 2H), 7.21-7.33 (m, 10H), 6.85-7.08 (m, 6H), 6.82-6.85 (m, 4H), 4.53-4.65 (m, 2H), 4.23-4.46 (m, 5H), 3.98-4.08 (m, 5H), 3.81 (s, 3H), 3.78 (s, 3H), 3.53-3.75 (m, 9H), 3.38-3.46 (m, 3H), 2.89-3.21 (m, 9H), 2.69-2.78 (m, 5H), 2.50-2.53 (m, 2H), 2.37-2.41 (m, 2H), 2.19-2.23 (m, 2H), 1.81-1.90 (m, 2H), 1.45-1.71 (m, 4H), 1.25-1.38 (m, 4H). HRMS (ESI) calcd for C$_{76}$H$_{99}$N$_{12}$O$_{18}$S$^+$ [M+H]$^+$ 1499.6916. found, 1499.6937. 2-(4-(((2-amino-4-hydroxypteridin-6-yl)methyl)amino)benzamido)pentanedioic acid Folate Receptor Ligands Folate receptor alpha is another well studied biomarker that is over expressed by a wide range of human tumors such as ovarian, endometrial, breast, lung, renal, and colon (J. F. Ross, P. K. Chaudhuri and M. Ratnam, *Cancer*, 1994, 73, 2432-2443 and S. D. Weitman, R. H. Lark, L. R. Coney, D. W. Fort, V. Frasca, V. R. Zurawski and B. A. Kamen, *Cancer Res.*, 1992, 52, 3396-3401). Folic acid mono activated NHS ester 17 was prepared following literature procedure (S. Dhar, Z. Liu, J. r. Thomale, H. Dai and S. J. Lippard, *J. Am. Chem. Soc.*, 2008, 130, 11467-11476) starting with folic acid, 2-(4-(((2-amino-4-hydroxypteridin-6-yl)methyl)amino)benzamido)pentanedioic acid, 16, which is commercially available. As shown below, this ester undergoes amidation with 11-azido-3,6,9-trioxaundecan-1-amine 18 (available from Sigma-Aldrich) to afford a terminal azide modified folic acid 19 which can be coupled with strained ring alkyne 23 via "click" chemistry. Formation of these two intermediates is depicted in Scheme V and described in Example 5 below.

Scheme V

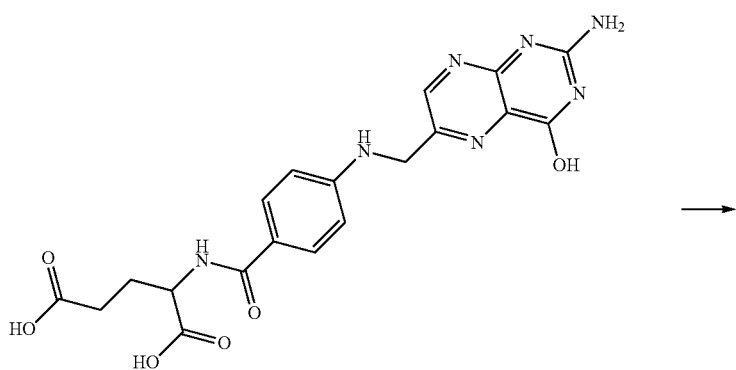

16

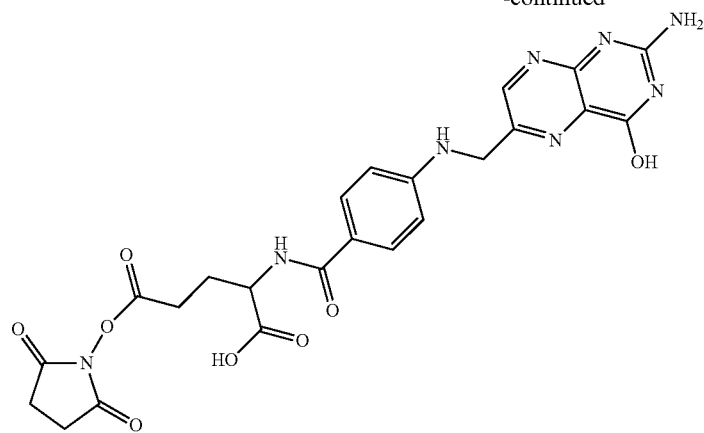
17
Reagents and conditions: (a) DCC, NHS, TEA, DMSO; 12 hr.
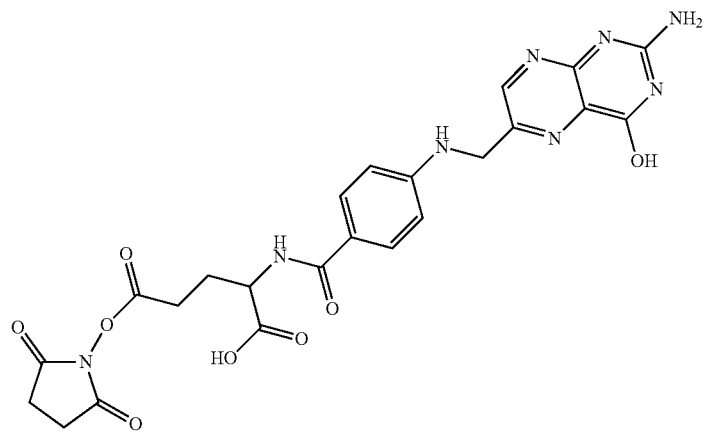
17
+
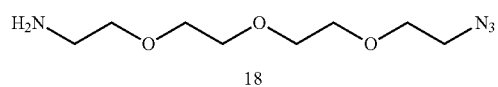
18
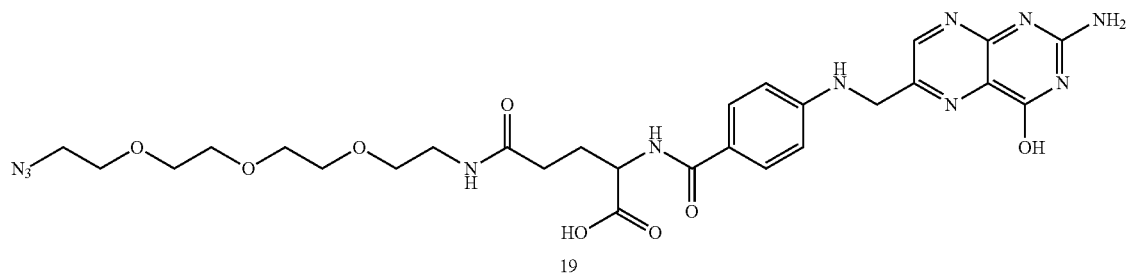
19
Reagents and condtions: (b) TEA, DMSO; 12 hr.

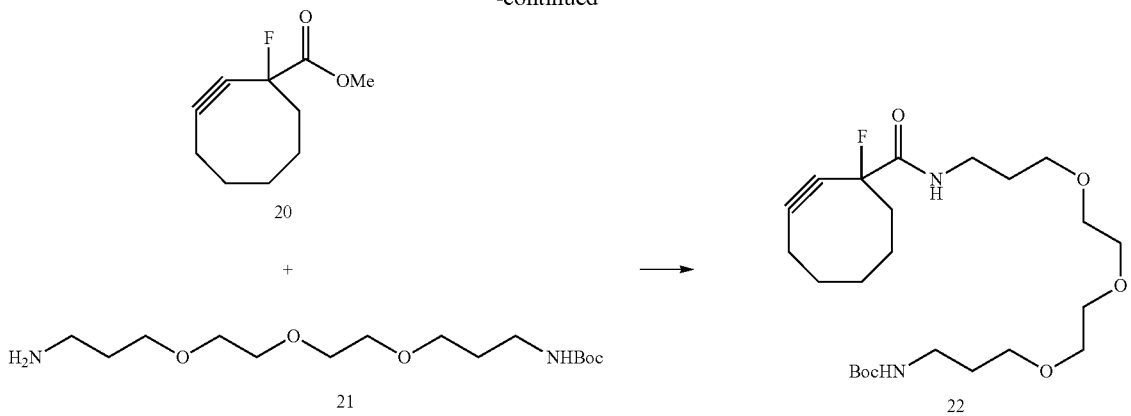

Reagents and condtions: (c)

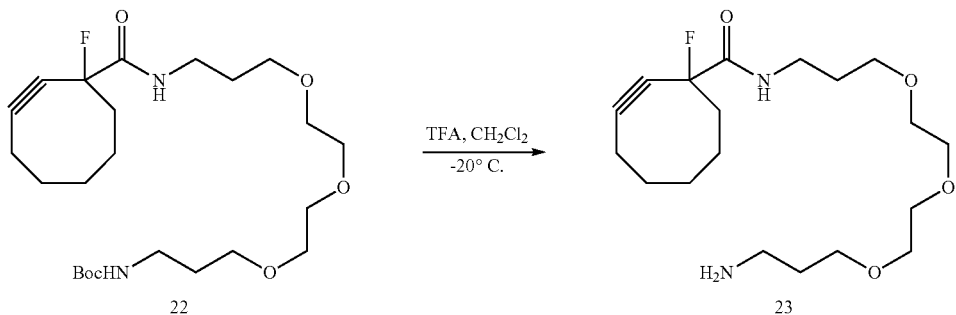

Reagents and condtions: (d)

Example 5

N-(3-(2-(2-(3-aminopropoxy)ethoxy)ethoxy)propyl)-1-fluorocyclooct-2-ynecarboxamide (23)

Preparation of 16-(4-(((2-amino-4-hydroxypteridin-6-yl)methyl)amino)benzamido)-1-azido-13-oxo-3,6,9-trioxa-12-azaheptadecan-17-oic acid (19): To a solution of 2-(4-(((2-amino-4-hydroxypteridin-6-yl)methyl)amino)benzamido)-5-((2,5-dioxopyrrolidin-1-yl)oxy)-5-oxopentanoic acid, 17, (100 mg, 0.19 mmol) in DMSO was added 11-azido-3,6,9-trioxaundecan-1-amine, 18, (30 mg, 0.25 mmol) followed by Et$_3$N (80 µL, 0.6 mmol). The reaction mixture was stirred at room temperature for 12 hours, and then purified by HPLC using a Shimadzu LC-10AT VP system with a Zobax C18 reversed-phase column (21.2 mm×25 cm). The sample was eluted (5 mL/min) with 75% buffer A (50 mM NH$_4$HCO$_3$ in H$_2$O) and 25% buffer B (acetonitrile). $^1$H NMR (DMSO-d6): δ 8.63 (s, 1H), 7.90-8.07 (m, 1H), 7.81-7.89 (m, 1H), 7.64 (d, J=8.0 Hz, 2H), 7.07 (brs, 2H), 6.92 (m, 1H), 6.64 (d, J=8.0 Hz, 2H), 4.48 (d, J=5.2 Hz, 1H), 4.23-4.27 (m, 1H), 3.38-3.59 (m, 12H), 3.16-3.24 (m, 4H), 2.16-2.31 (m, 2H), 1.94-2.18 (m, 1H), 1.86-1.92 (m, 1H). $^{13}$C NMR (DMSO-d6) δ 174.7, 174.6, 172.3, 166.5, 154.5, 151.2, 149.0, 148.9, 129.5, 129.3, 128.4, 122.0, 121.8, 111.7, 70.3, 70.2, 70.1, 70.0, 69.7, 69.5, 53.0, 50.5, 46.4, 32.5, 31.1, 27.5. HRMS (ESI) calcd for C$_{27}$H$_{36}$N$_{11}$O$_8^+$ [M+H]$^+$ 642.2743. found, 642.2735.

Preparation of tert-butyl (1-(1-fluorocyclooct-2-yn-1-yl)-1-oxo-6,9,12-trioxa-2-azapentadecan-15-yl)carbamate (22): To a neat mixture of methyl 1-fluorocyclooct-2-ynecarboxylate, 20, (prepared by the method of M. K. Schultz, S. G. Parameswarappa and F. C. Pigge, Org. Lett., 2010, 12, 2398-2401) (660 mg, 3.6 mmol) and tert-butyl (3-(2-(2-(3-aminopropoxy)ethoxy)-ethoxy)propyl)carbamate, 21, (1.65 g, 5.2 mmol) in a 10 mL vial was added Et$_3$N (0.5 mL). The resulting mixture was stirred at room temperature for 24 hours, and then purified by flash chramotography hexane:EtOAc (4:1 to 2:3) to give Boc protected cyclooctyne amide 22 as a pale yellow oil (1.0 g, 60%). $^1$H NMR (DMSO-d6) δ 7.03 (brs, 1H), 4.99 (brs, 1H), 3.53-3.66 (m, 10H), 3.40-3.43 (m, 2H), 3.22-3.24 (m, 2H), 2.25-2.44 (m, 3H), 1.85-2.08 (m, 3H), 1.49-1.83 (m, 6H), 1.26 (s, 9H). HRMS (ESI) calcd for C$_{24}$H$_{42}$FN$_2$O$_6^+$ [M+H]$^+$ 473.3021. found, 473.3029.

Preparation of N-(3-(2-(2-(3-aminopropoxy)ethoxy)ethoxy)propyl)-1-fluorocyclo-oct-2-ynecarboxamide (23): To a solution of tert-butyl (1-(1-fluorocyclooct-2-yn-1-yl)-1-oxo-6,9,12-trioxa-2-azapentadecan-15-yl)carbamate, 22, (200 mg, 0.43 mmol) in CH$_2$Cl$_2$ (5 mL) was added TFA (5 mL) dropwise at −20° C. The resulting mixture was stirred for 2 hours then diluted with DCM (20 mL) and dried under vacuum another portion of DCM (20 mL) was added and dried under vacuum again to remove all TFA. The residue was purified by silica gel column chromatography by DCM:MeOH (50:1 to 10:1) to give the desired product as a pale yellow oil (150 mg, 96%). $^1$H NMR (CDCl$_3$) δ 1.34-1.41 (m, 1H), 1.55-1.63 (m, 1H), 1.71-1.93 (m, 7H), 1.96-2.05 (m, 1H), 2.19-2.36 (m, 4H), 3.09 (m, 2H), 3.31 (q, 2H, J=6.0 Hz), 3.47-3.53 (m, 4H), 3.56-3.62 (m, 8H); $^{13}$C NMR (CDCl$_3$) δ 20.6, 25.7, 26.6, 28.8, 29.0, 33.9, 37.8, 39.3, 46.5 (d, $J^2{}_{C-F}$=36.0 Hz), 69.6, 69.7, 69.9, 69.9, 70.0, 70.3, 87.3 (d, $J^2{}_{C-F}$=31.0 Hz), 94.4 (d, $J_{C-F}$=185.0 Hz), 109.5 (d, $J^3{}_{C-F}$=11.0 Hz), 168.8 (d, $J^2{}_{C-F}$=24.0 Hz). HRMS (ESI) calcd for C$_{19}$H$_{34}$FN$_2$O$_4^+$ [M+H]$^+$ 373.2497. found, 373.2501.

Scheme VI below and Example 6 provide a non-limiting example of assembly of the final folic receptor conjugate.
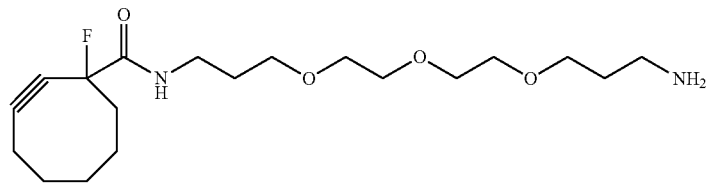
23
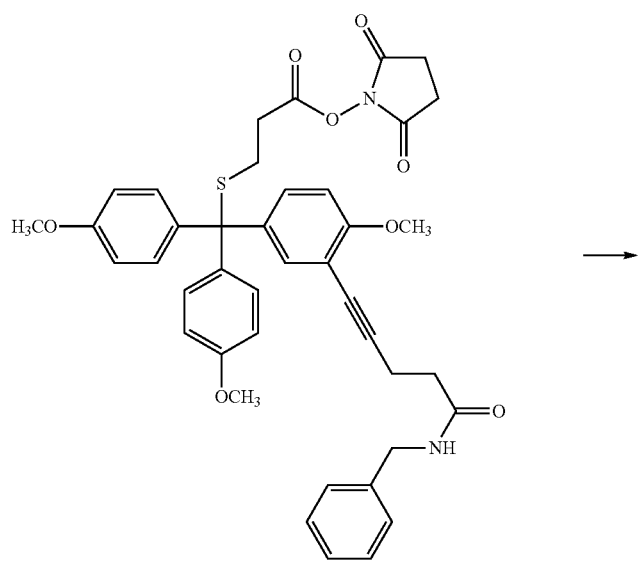
5
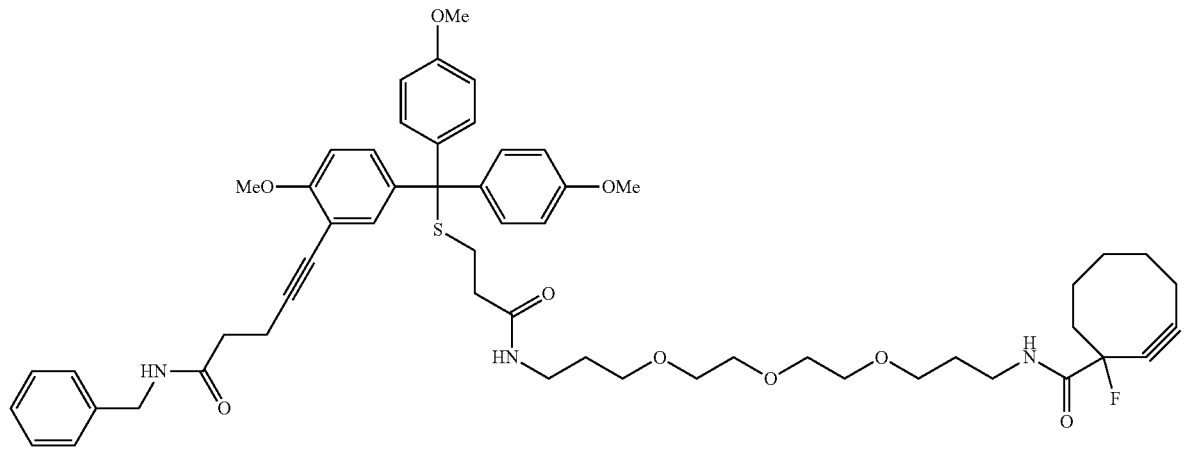
24
Reagents and Conditions: (a) TEA, CH₂CL₂; 12 hr. rt.

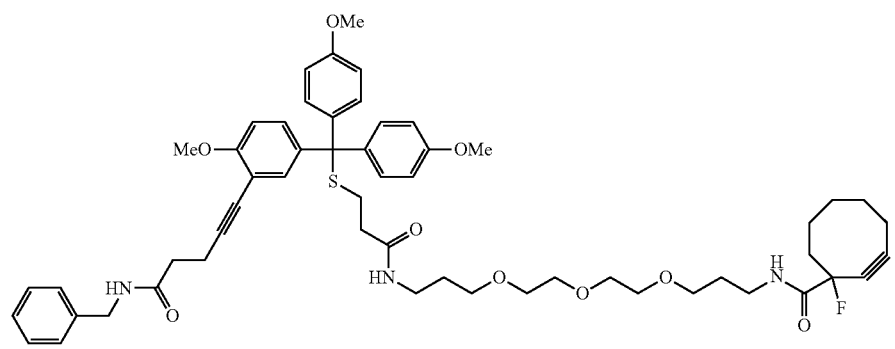
24
+
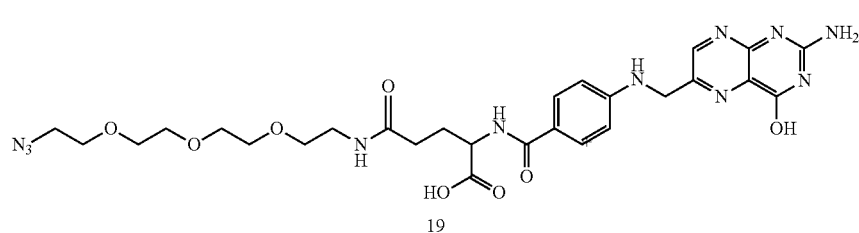
19
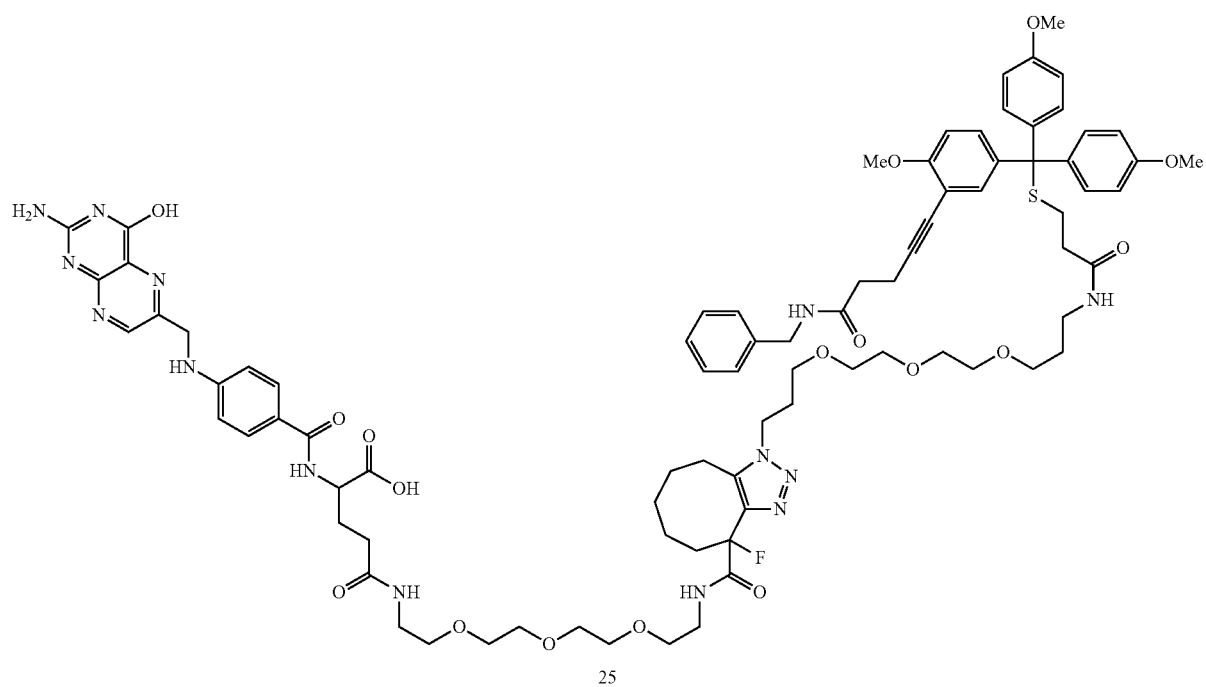
25
Reagents and conditions: (b) CH₂Cl₂, DMSO; 12 hr. rt.

Example 6

18-(4-(((2-Amino-4-hydroxypteridin-6-yl)methyl)amino)benzamido)-1-(1-(1-(3-(5-(benzylamino)-5-oxopent-1-yn-1-yl)-4-methoxyphenyl)-1,1-bis(4-methoxyphenyl)-5-oxo-10,13,16-trioxa-2-thia-6-azanonadecan-19-yl)-4-fluoro-4,5,6,7,8,9-hexahydro-1H-cycloocta[d][1,2,3]triazol-4-yl)-1,15-dioxo-5,8,1-trioxa-2,14-diazanonadecan-19-oic acid (25)

Preparation of N-(1-(3-(5-(benzylamino)-5-oxopent-1-yn-1-yl)-4-methoxyphenyl)-1,1-bis(4-methoxyphenyl)-5-oxo-10,13,16-trioxa-2-thia-6-azanonadecan-19-yl)-1-fluorocyclooct-2-ynecarboxamide (24): To a solution of 2,5-dioxopyrrolidin-1-yl 3-(((3-(5-(benzylamino)-5-oxopent-1-yn-1-yl)-4-methoxyphenyl)bis(4-methoxyphenyl)methyl)thio)-propanoate, 5, (50 mg, 70 µmol) in $CH_2Cl_2$ (0.5 mL) was added N-(3-(2-(2-(3-amino-propoxy)ethoxy)ethoxy)propyl)-1-fluorocyclooct-2-ynecarboxamide, 23, (38 mg, 0.1 mmol) dissolved in $CH_2Cl_2$ (0.5 mL) followed by $Et_3N$ (25 µL, 0.18 mmol). The resulting mixture was stirred at room temperature for 12 hours, and then diluted with $CH_2Cl_2$ (10 mL) washed with brine, dried over $Na_2SO_4$, concentrated in vacuum. The residue was purified by flash chromatography $CH_2Cl_2$/MeOH 10:1 to give pale yellow foam 55 mg, yield 81%. $^1$H NMR ($CDCl_3$) δ 7.49 (brs, 1H), 7.24-7.29 (m, 6H), 7.16-7.20 (m, 4H), 7.02 (brs, 1H), 6.82 (d, J=8.8 Hz, 1H), 6.71-6.76 (m, 2H), 6.22 (brs, 1H), 4.45 (d, J=6.4 Hz, 1H), 3.79 (s, 6H), 3.74 (s, 3H), 3.53-3.61 (m, 12H), 3.37 (dd, J=5.6, 6.0 Hz, 2H), 3.31 (dd, J=5.6, 6.0 Hz, 2H), 2.80 (t, J=6.8 Hz, 2H), 2.56 (t, J=6.8 Hz, 2H), 2.42 (t, J=6.8 Hz, 2H), 2.29-2.32 (m, 2H), 2.12 (t, J=7.2 Hz, 2H), 1.85-2.05 (m, 4H), 1.63-1.82 (m, 6H), 1.28-1.49 (m, 2H); $^{13}$C NMR ($CDCl_3$) δ 171.6, 170.9, 158.4, 158.1, 138.4, 137.4, 132.2, 132.1, 132.0, 131.9, 130.5, 129.1, 128.6, 128.5, 128.4, 127.6, 127.5, 127.2, 113.6, 113.2, 111.8, 109.8, 109.2, 109.1, 95.4, 93.5, 92.8, 87.3, 78.3, 70.5, 70.4, 70.3, 70.1, 69.9, 64.9, 55.8, 55.2, 46.5, 46.3, 43.5, 38.1, 37.9, 35.9, 35.4, 33.9, 29.7, 28.9, 28.8, 28.7, 25.7, 20.6, 20.5. HRMS (ESI) calcd for $C_{56}H_{69}FN_3O_9S^+$ [M+H]$^+$ 978.4733. found, 978.4745.

Preparation of 18-(4-(((2-Amino-4-hydroxypteridin-6-yl)methyl)amino)benzamido)-1-(1-(1-(3-(5-(benzylamino)-5-oxopent-1-yn-1-yl)-4-methoxyphenyl)-1,1-bis(4-methoxyphenyl)-5-oxo-10,13,16-trioxa-2-thia-6-azanonadecan-19-yl)-4-fluoro-4,5,6,7,8,9-hexa-hydro-1H-cycloocta[d][1,2,3]triazol-4-yl)-1,15-dioxo-5,8,11-trioxa-2,14-diazanonadecan-19-oic acid (25): To a solution of 16-(4-(((2-amino-4-hydroxypteridin-6-yl)methyl)amino)-benzamido)-1-azido-13-oxo-3,6,9-trioxa-12-azaheptadecan-17-oic acid, 19, (17 mg, 0.17 mmol) in DMSO (0.3 mL) was added 16-(4-(((2-amino-4-hydroxypteridin-6-yl)methyl)-amino)benzamido)-1-azido-13-oxo-3,6,9-trioxa-12-azaheptadecan-17-oic acid, 19, (11 mg, 0.17 mmol) in $CH_2Cl_2$. The reaction mixture was stirred at room temperature for 12 hours, and then purified by HPLC using a Shimadzu LC-100AT VP system with a Zobax C18 reversed-phase column (21.2 mm×25 cm). The sample was eluted (5 mL/min) with 50% buffer A (100 mM $NH_4HCO_3$ in $H_2O$) and 50% buffer B (acetonitrile). $^1$H NMR (DMSO-d6): 8.63 (s, 1H), 8.40 (brs, 1H), 8.24 (brs, 1H), 7.92 (brs, 1H), 7.78-7.85 (m, 2H), 7.54-7.67 (m, 2H), 7.15-7.21 (m, 10H), 6.97 (d, J=8.4 Hz, 1H), 6.86 (d, J=8.4 Hz, 2H), 6.64 (d, J=8.4 Hz, 2H), 4.46 (brs, 2H), 4.24-4.33 (m, 2H), 4.05-4.09 (m, 2H), 3.77 (s, 3H), 3.72 (s, 6H), 3.42-3.47 (m, 20H), 3.16-3.28 (m, 4H), 3.01-3.06 (m, 3H), 2.89 (brs, 1H), 2.63 (t, J=6.8 Hz, 2H), 2.40 (t, J=6.8 Hz, 2H), 2.08-2.29 (m, 6H), 1.82-2.03 (m, 2H), 1.56-1.88 (m, 6H), 1.35-1.51 (m, 2H); HRMS (ESI) calcd for $C_{83}H_{104}FN_{14}O_{17}S^+$ [M+H]$^+$ 1619.7403. found, 1619.7423.

Methods

Disclosed herein are methods for detecting particular surface antigens, especially antigens associated with cancer cells. Cancer cell surface carbohydrate antigens are biomarkers that indicate the presence of cancer cells. For example, silalyl Lewis X antigen comprises a polysaccharide having the formula:

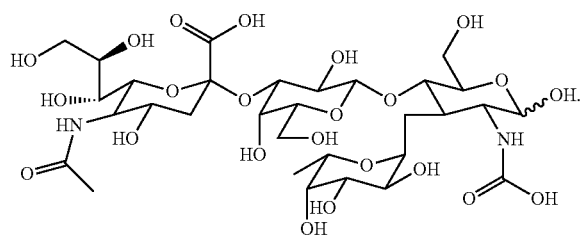 [SMILES: CC(=O)NC1C(O)CC(OC2C(O)C(CO)OC(OC3C(CO)OC(O)C(NC(=O)O)C3CC3OC(C)C(O)C(O)C3O)C2O)(C(=O)O)OC1[C@H](O)[C@H](O)CO]

This polysaccharide is found on the surface of many cancer cells. Without wishing to be bound by theory, one category of the disclosed imaging agents have an affinity for this polysaccharide and are capable of binding by way of the boronic acid units to one or more hydroxyl or carbonyl units. The disclosed imaging agents are contacted with tissue after which the tissue is analyzed by MALDI-MS, MALDI-TOF, or other tissue compatible mass spectroscopy.

In a further embodiment, disclosed is a method for determining the presence of a cancer cell by contacting a cell with a disclosed imaging agent capable of binding to an RGD receptor of a cancer cell and subjecting the cell to MALDI-MS, MALDI-TOF, or other tissue compatible mass spectroscopy.

In a yet further embodiment, disclosed is a method for determining the presence of a cancer cell by contacting a cell with a disclosed imaging agent capable of binding to a folate receptor of a cancer cell and subjecting the cell to MALDI-MS, MALDI-TOF, or other tissue compatible mass spectroscopy.

Disclosed is a method for identifying a surface antigen associated with a cancer cell, comprising contacting a sample comprising cells with a disclosed imaging agent and processing the sample such that any of the imaging agents which adhere to the cells are fragmented and the stabilized cation formed is detected.

Disclosed is the following method for identifying cancer cells via their surface antigens, comprising:
 a) contacting a tissue sample with a disclosed imaging agent;
 b) subjecting the tissue sample to electromagnetic radiation in the context of mass spectral analysis; and
 c) detecting the presence of a stable carbocation formed from the fragmentation of the imaging agent.

Further disclosed is a method for detecting the presence of cancer cells, comprising:
 a) contacting tissue with one or more of the disclosed imaging agents;
 b) subjecting the tissue to the conditions of MALDI mass spectral analysis; and
 c) determining if a stable carbocation fragmented from the imaging agent is present.

The formulator can choose to prepare imaging agents having varying degrees of affinity for one or more surface antigens. For example, the formulator can prepare an imaging agent that has "selective affinity" for antigens that comprise similar structure, for example, an imaging agent capable of binding to carbohydrate comprising-antigens such as sialyl Lewis A:

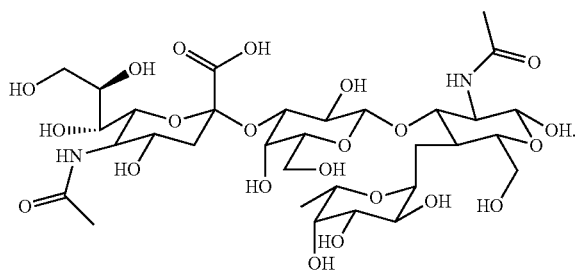 [SMILES: CC(=O)NC1C(O)OC(CO)C(CC2OC(C)C(O)C(O)C2O)C1OC1OC(CO)C(O)C(OC2(C(=O)O)CC(O)C(NC(C)=O)C([C@H](O)[C@H](O)CO)O2)C1O]

If desirable, the formulator can, however, prepare an imaging agent that has specific affinity, for example, will bind only to a specific carbohydrate comprising antigen, for example, only to sialyl Lewis X or to sialyl Lewis A. Therefore, disclosed herein is a method for determining the presence of cell having a specific polysaccharide or carbohydrate containing antigen. Non-limiting examples of surface antigens include Globo H, Thomsen-Friedenreich (TF) antigen, Fucosyl $GM_1$ (fucosylated monosialoganglioside $GM_1$), Lewis y Hapten.

Procedures

Figure 3:
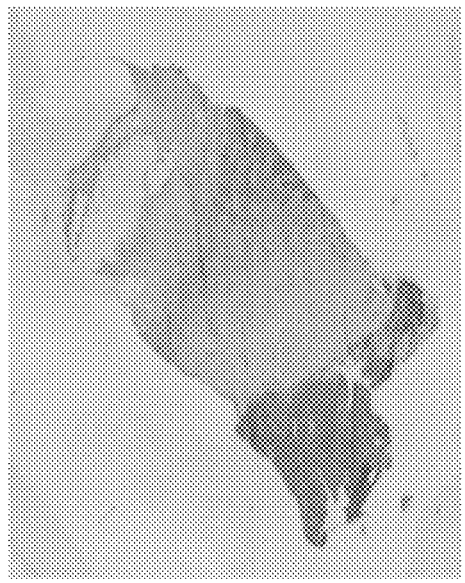
FIG. 3 depicts the immuno-stained image of the same kidney sample. The region of renal cell carcinoma (RCC) is indicated and is in contrast to the immune-stain for normal kidney cells.

A tissue slice containing renal cell carcinoma was immunostained (mouse monoclonal antibody, GenWay Biotech San Diego, Calif.) that expressed regions coincident with the tumor area (dark stained bottom tip area of FIG. 3; confirmed by pathological analysis).

An adjacent tissue slice (7 μm) was placed on a conductive slide and incubated with the imaging agent of Example 3 in 100% methanol (2 ng/μl) in a humid chamber overnight at 4° C. Slides were washed for 5 minutes in PBS followed by brief water wash to remove any unbound material. The slides are placed in a desiccator for 20 minutes and analyzed directly by MALDI-TOF (no matrix is added) in the reflectron mode using a laser raster width of 200 μm.

Figure 2:
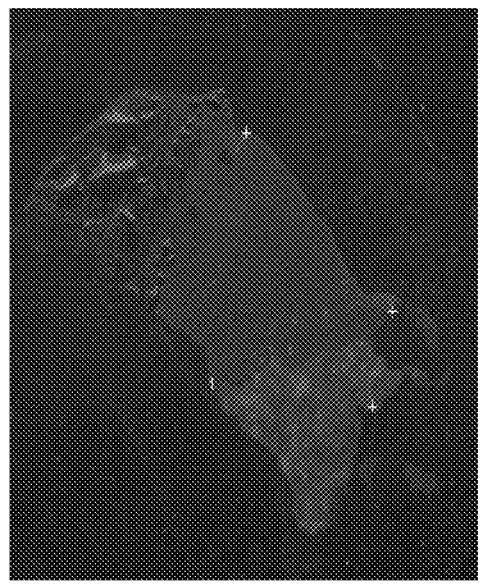
FIG. 2 depicts the MALDI-IMS image for the stable carbocation generated from the boronolectin-MS tag conjugate disclosed in Example 3 when applied to fresh-frozen renal tissues containing both tumor and normal regions. The area of renal cell carcinoma (RCC) is indicated as a contrast to the normal kidney cells. The region of biomarker generated stabilized cation is indicated in red.

FIG. 2 depicts the MALDI-IMS image of this tissue sample wherein the areas of renal carcinoma containing tissue are indicated in red due to the presence of the stabilized carbocation formed from the fragmentation of the imaging agent which bound only to the cells expressing sialyl Lewis X antigen. The stabilized carbocation is used in this example located and confirm immunological and pathology analysis of this sample that the MALDI indicated region corresponded to the area associated with cancerous tissue.

Figure 4:
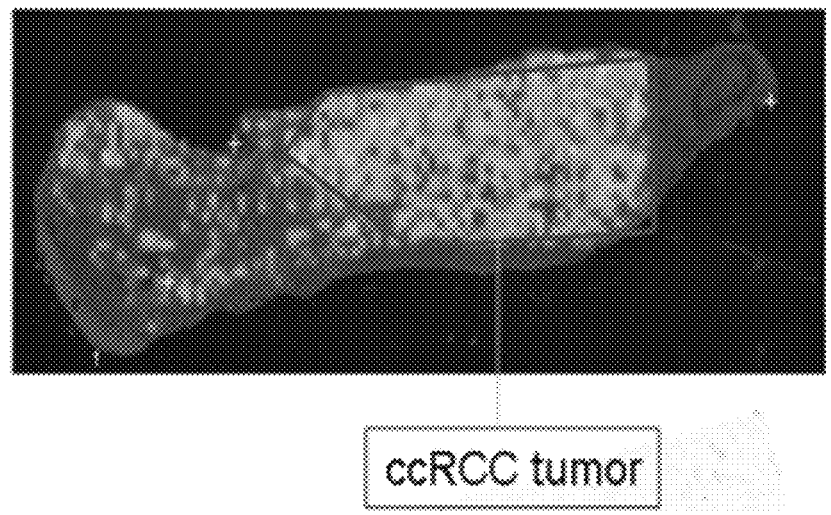
FIG. 4 depicts the immune-staining seen using the boronolectin disclosed in Example 3 of a UMFIX/Sakura alcohol fixed real tumor tissue.
Figure 5:
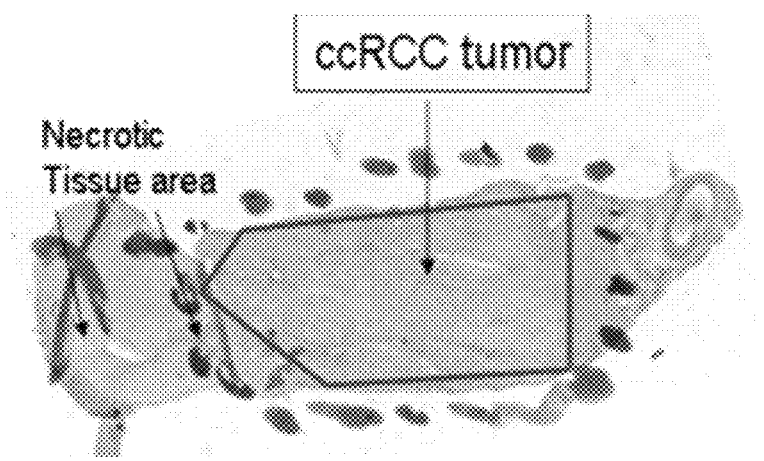
FIG. 5 depicts the UMFIX/Sakura alcohol fixed real tumor tissue that is imaged in FIG. 4.

FIG. 4 depicts the MALDI-IMS of a renal cell carcinoma tissue sample exposed to the imaging agent of Example 3. FIG. 5 depicts the same tissue sample stained with Sakura/UMFx alcohol. The tumor cells in FIG. 4 are depicted as green dots where the imaging agent is affixed to the cell surface. This demonstrates that the disclosed imaging agents can be used for probing tumor tissue microarrays prepared from alcohol or formalin fixed tissues.

As seen in FIG. 2 and FIG. 3 only the region of tumor with sialyl Lewis X antigen expression was there binding of the imaging agent, as shown in red pixel intensities (FIG. 2).

These red pixels correlate to the MALDI peaks in the spectra shown in FIG. 1 and the color intensity is related to peak abundance as shown in the expression scale. Peaks were obtained in the absence of any chemical matrix. As depicted in FIG. 4 and FIG. 5, this imaging agent is also capable of binding to alcohol fixed renal tissues. As such, this provides a method for probing tumor tissue microarrays prepared from alcohol or formalin fixed tissues.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure

What is claimed is:

1. An imaging agent having the formula:

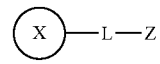

wherein X is chosen from:

i)

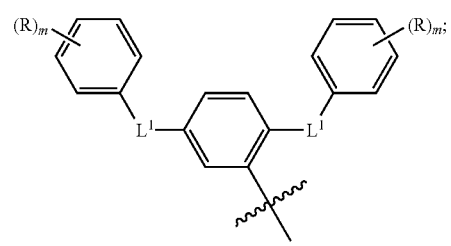

ii)

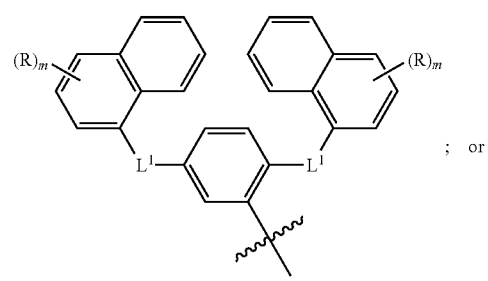

; or iii)

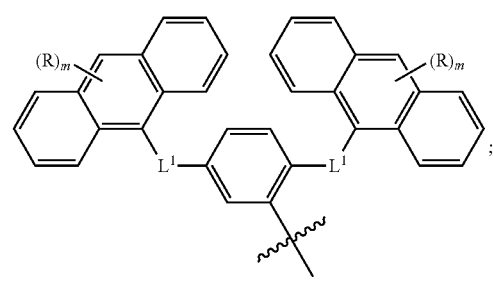

;

each $L^1$ is independently chosen from:
i) —$(CH_2)_yC(O)O(CH_2)_z$—;
ii) —$(CH_2)_yOC(O)(CH_2)_z$—;
iii) —$(CH_2)_yC(O)NR^6(CH_2)_z$—;
iv) —$(CH_2)_yNR^6C(O)(CH_2)_z$—;
v) —$(CH_2)_yNR^6C(O)NH(CH_2)_z$—; or
vi) —$(CH_2)_yNR^6C(NR^6)NR^6(CH_2)_z$—;

$R^6$ is hydrogen or $C_1$-$C_3$ linear alkyl; the index y is an integer from 0 to 4, the index z is an integer form 0 to 4;

R has the formula:

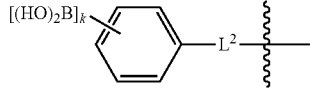

the index k is an integer from 1 to 5;
$L^2$ has the formula:
i) $(CH_2)_p NR^7 (CH_2)_q$; or
ii) $(CH_2)_p O(CH_2)_q$;
$R^7$ is hydrogen or $C_1$-$C_3$ linear alkyl; the index p is an integer from 0 to 5; the index q is an integer from 0 to 5;

Z has the formula:

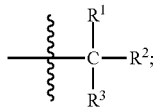

$R^1$ an $R^2$ are substituted or unsubstituted aryl groups chosen from phenyl, naphthyl, anthracenyl, phenanthrenyl, or tetracenyl;
$R^3$ is a substituted or unsubstituted aryl group chosen from phenyl, naphthyl, anthracenyl, phenanthrenyl, or tetracenyl, and wherein $R^3$ further comprises an anchoring group having the formula:

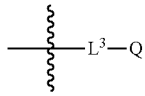

wherein Q is a unit having the formula:
i) $-(CH_2)_r C(O)O(CH_2)_t R^9$;
ii) $-(CH_2)_r OC(O)(CH_2)_t R^9$;
iii) $-(CH_2)_r C(O)NR^8(CH_2)_t R^9$;
iv) $-(CH_2)_r NR^8 C(O)(CH_2)_t R^9$;
v) $-(CH_2)_r NR^8 C(O)NH(CH_2)_t R^9$; and
vi) $-(CH_2)_r NR^8 C(NR^8)NR^8(CH_2)_t R^9$;
$R^8$ is hydrogen or $C_1$-$C_3$ linear alkyl; the index r is an integer from 0 to 4 and the index t is an integer form 0 to 4; $R^9$ is phenyl or naphthyl;
$L^3$ comprises one or more units chosen from $-CH_2-$, $-CH=CH-$, $-C\equiv C-$, $-CH_2CH_2O-$, $-CH_2CH_2CH_2O-$, $-CH_2CH(CH_3)O-$, and $-CH(CH_3)CH_2O-$;
L is a linking unit that comprises a fragmentable bond such that under the conditions of MALDI-MS or other mass spectrum conditions releases a stable cation having the formula:

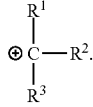

2. The imaging agent according to claim 1, wherein L is chosen from:

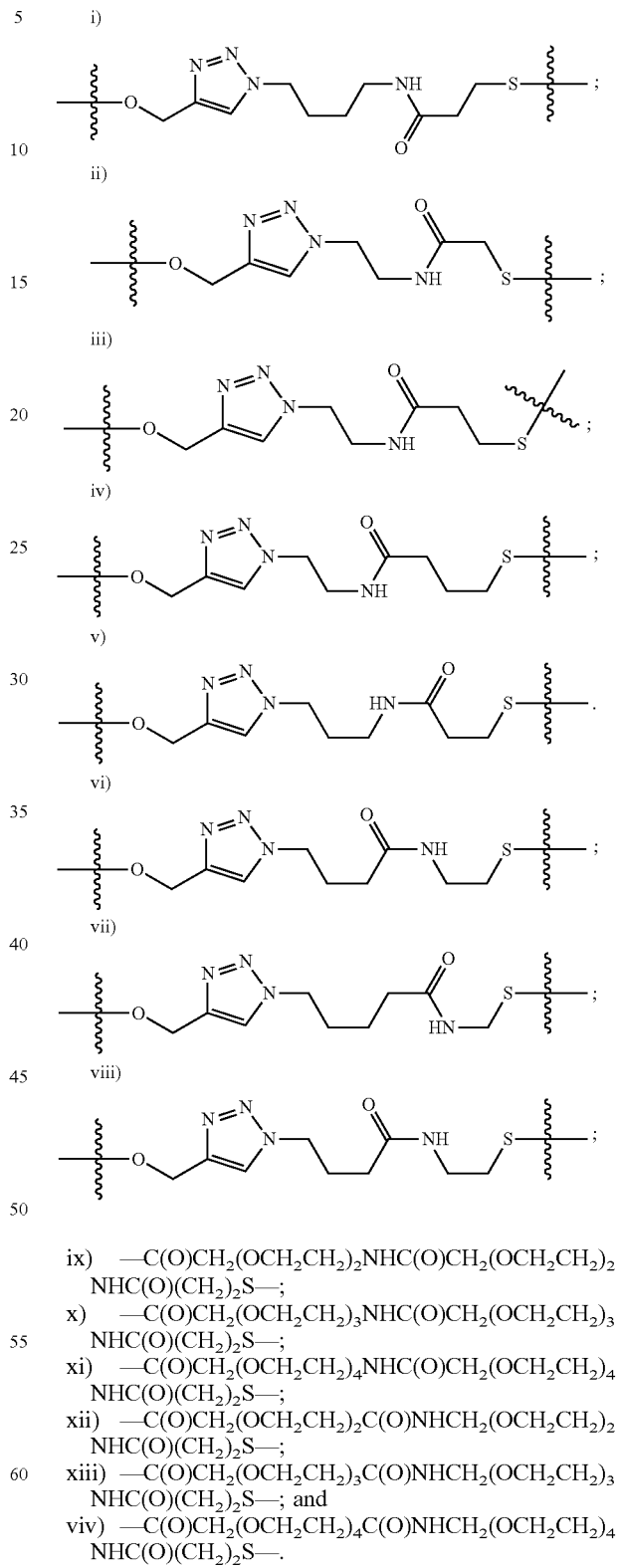

ix) $-C(O)CH_2(OCH_2CH_2)_2NHC(O)CH_2(OCH_2CH_2)_2NHC(O)(CH_2)_2S-$;
x) $-C(O)CH_2(OCH_2CH_2)_3NHC(O)CH_2(OCH_2CH_2)_3NHC(O)(CH_2)_2S-$;
xi) $-C(O)CH_2(OCH_2CH_2)_4NHC(O)CH_2(OCH_2CH_2)_4NHC(O)(CH_2)_2S-$;
xii) $-C(O)CH_2(OCH_2CH_2)_2C(O)NHCH_2(OCH_2CH_2)_2NHC(O)(CH_2)_2S-$;
xiii) $-C(O)CH_2(OCH_2CH_2)_3C(O)NHCH_2(OCH_2CH_2)_3NHC(O)(CH_2)_2S-$; and
viv) $-C(O)CH_2(OCH_2CH_2)_4C(O)NHCH_2(OCH_2CH_2)_4NHC(O)(CH_2)_2S-$.

3. An imaging agent according to claim 1, wherein L units have the formula:

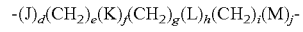

wherein J, K, L and M are each independently chosen from:
i) —(CH$_2$)$_{yy}$O(CH$_2$)$_{zz}$—;
ii) —(CH$_2$)$_{yy}$NH(CH$_2$)$_{zz}$—;
iii) —(CH$_2$)$_{yy}$S(CH$_2$)$_{zz}$—;
iv) —(CH$_2$)$_{yy}$C(O)(CH$_2$)$_{zz}$—
v) —(CH$_2$)$_{yy}$OC(O)(CH$_2$)$_{zz}$—;
vi) —(CH$_2$)$_{yy}$C(O)O(CH$_2$)$_{zz}$—;
vii) —(CH$_2$)$_{yy}$NHC(O)(CH$_2$)$_{zz}$—;
viii) —(CH$_2$)$_{yy}$C(O)NH(CH$_2$)$_{zz}$—;
ix) —(CH$_2$)$_{yy}$NHC(O)NH(CH$_2$)$_{zz}$—;
x) —(CH$_2$)$_{yy}$C(S)(CH$_2$)$_{zz}$—;
xi) —(CH$_2$)$_{yy}$NHC(S)(CH$_2$)$_{zz}$—
xii) —(CH$_2$)$_{yy}$C(S)NH(CH$_2$)$_{zz}$—;
xiii) —(CH$_2$)$_{yy}$NHC(S)NH(CH$_2$)$_{zz}$—;
xiv) C$_3$-C$_{10}$ carbocyclic rings;
xv) aryl rings chosen from phenyl and napthyl;
xvi) heterocyclic rings comprising from 1 to 4 heteroatoms chosen from nitrogen (N), oxygen (O) and sulfur (S); and
xvii) heteroaryl rings comprising from 1 to 4 heteroatoms chosen from nitrogen (N), oxygen (O) and sulfur (S); and
xviii) any combination thereof for each of J, K, L and M;
the indices d, f, h and j are 0 or 1; the indices e, g and i are independently integers from 0 to 1.

4. An imaging agent according to claim 1, wherein Z has the formula:

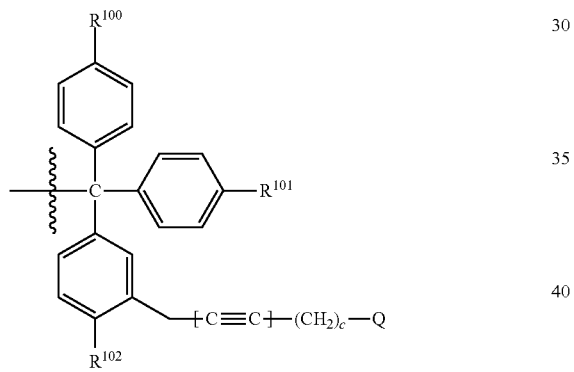

wherein R$^{100}$, R$^{101}$ and R$^{102}$ are each independently —OR$^{10}$; R$^{10}$ is C$_1$-C$_4$ alkyl, the index c is from 1 to 100.

5. An imaging agent according to claim 4, wherein Z has the formula:

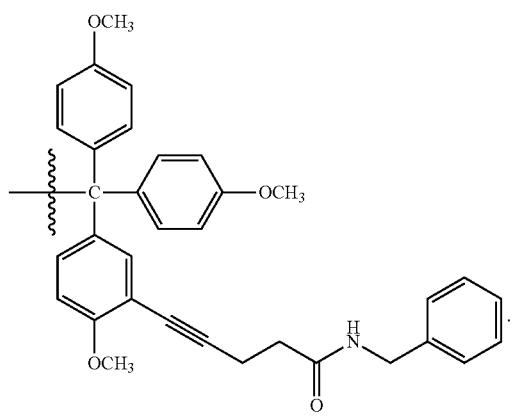 [SMILES: *C(c1ccc(OC)cc1)(c1ccc(OC)cc1)c1ccc(OC)c(C#CCCC(=O)NCc2ccccc2)c1]

6. An imaging agent according to claim 1, wherein X has the formula chosen from:

i)

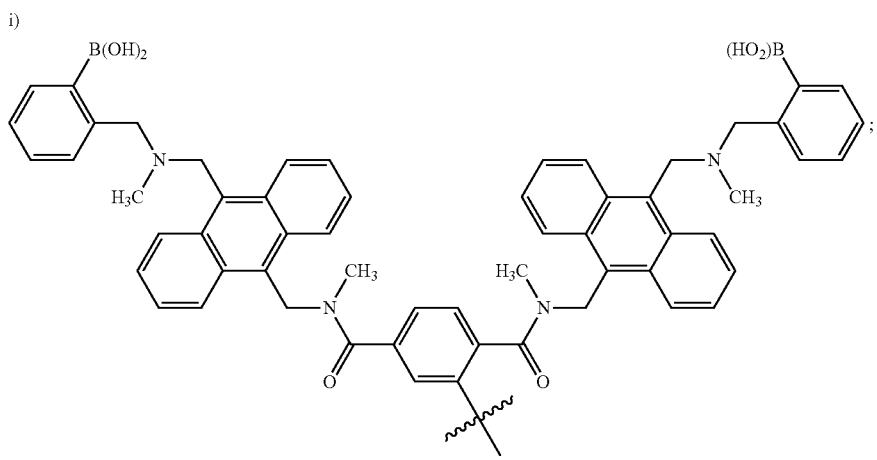

ii)
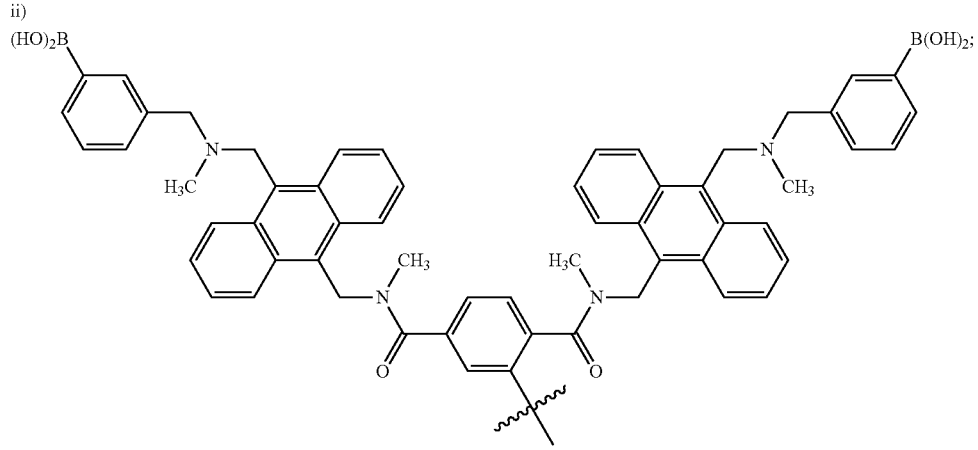
iii)
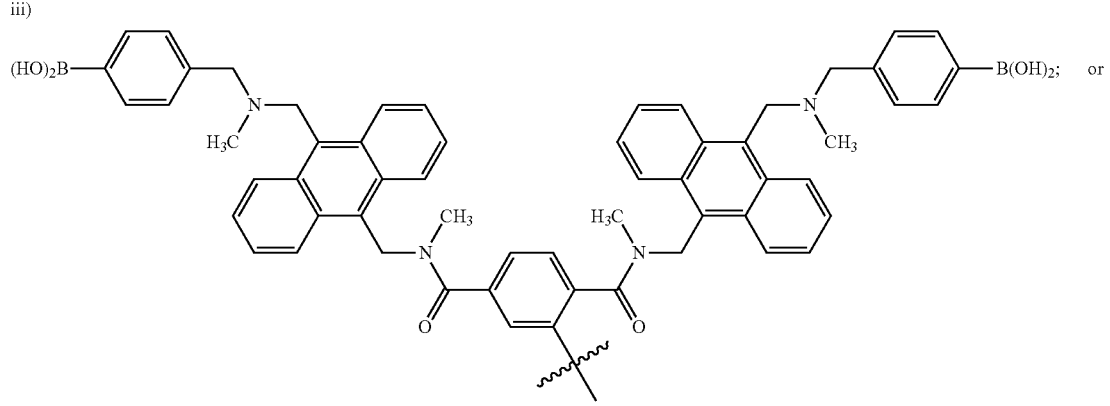 or
iv)
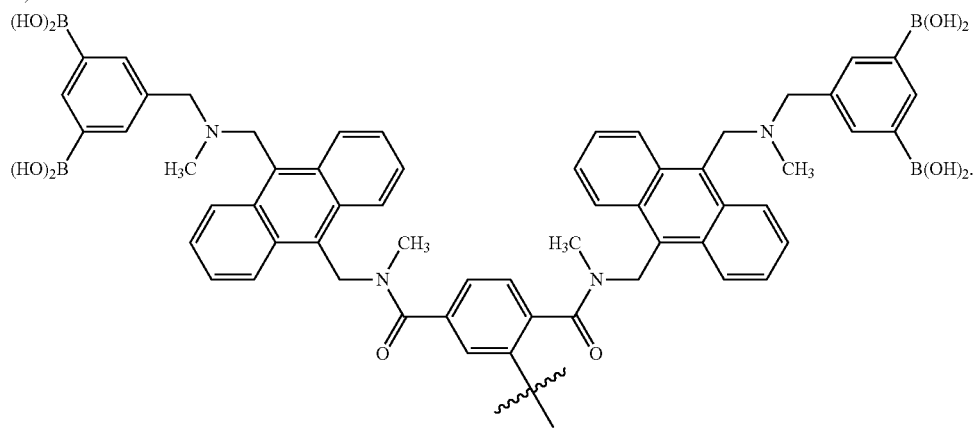

7. An imaging agent having the formula:

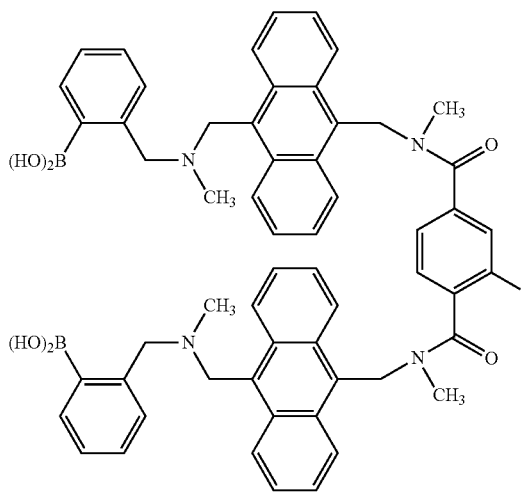

Z has the formula:

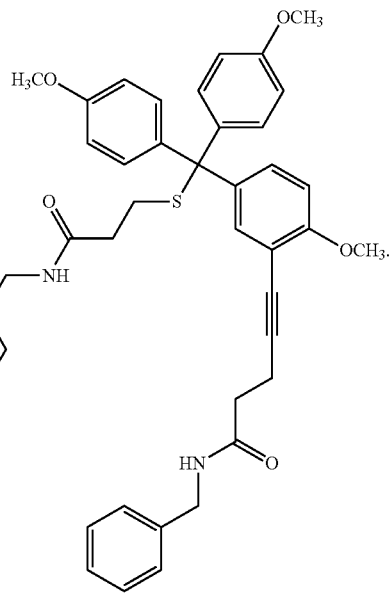

8. An imaging agent having the formula:

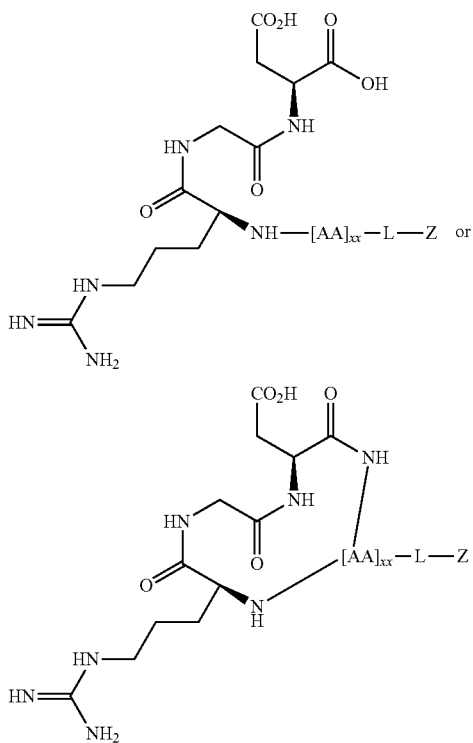

wherein AA is a naturally occurring or synthetic amino acid, xx is and integer from 1 to 7;

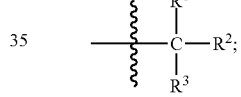

$R^1$ an $R^2$ are substituted or unsubstituted aryl groups chosen from phenyl, naphthyl, anthracenyl, phenanthrenyl, or tetracenyl;

$R^3$ is a substituted or unsubstituted aryl group chosen from phenyl, naphthyl, anthracenyl, phenanthrenyl, or tetracenyl, and wherein $R^3$ further comprises an anchoring group having the formula:

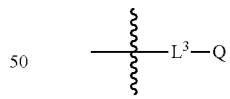

wherein Q is a unit having the formula:
i) —$(CH_2)_rC(O)O(CH_2)_tR^9$;
ii) —$(CH_2)_rOC(O)(CH_2)_tR^9$;
iii) —$(CH_2)_rC(O)NR^8(CH_2)_tR^9$;
iv) —$(CH_2)_rNR^8C(O)(CH_2)_tR^9$;
v) —$(CH_2)_rNR^8C(O)NH(CH_2)_tR^9$; and
vi) —$(CH_2)_rNR^8C(NR^8)NR^8(CH_2)_tR^9$;

$R^8$ is hydrogen or $C_1$-$C_3$ linear alkyl; the index r is an integer from 0 to 4 and the index t is an integer form 0 to 4; $R^9$ is phenyl or naphthyl;

$L^3$ comprises one or more units chosen from —$CH_2$, —$CH=CH$—, —$C\equiv C$—, —$CH_2CH_2O$—, —$CH_2CH_2CH_2O$—, —$CH_2CH(CH_3)O$—, and —$CH(CH_3)CH_2O$—;

L is a linking unit that comprises a fragmentable bond such that under the conditions of MALDI-MS or other mass spectrum conditions releases a stable cation having the formula:

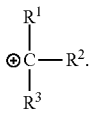

9. The imaging agent according to claim 8, wherein L is chosen from:

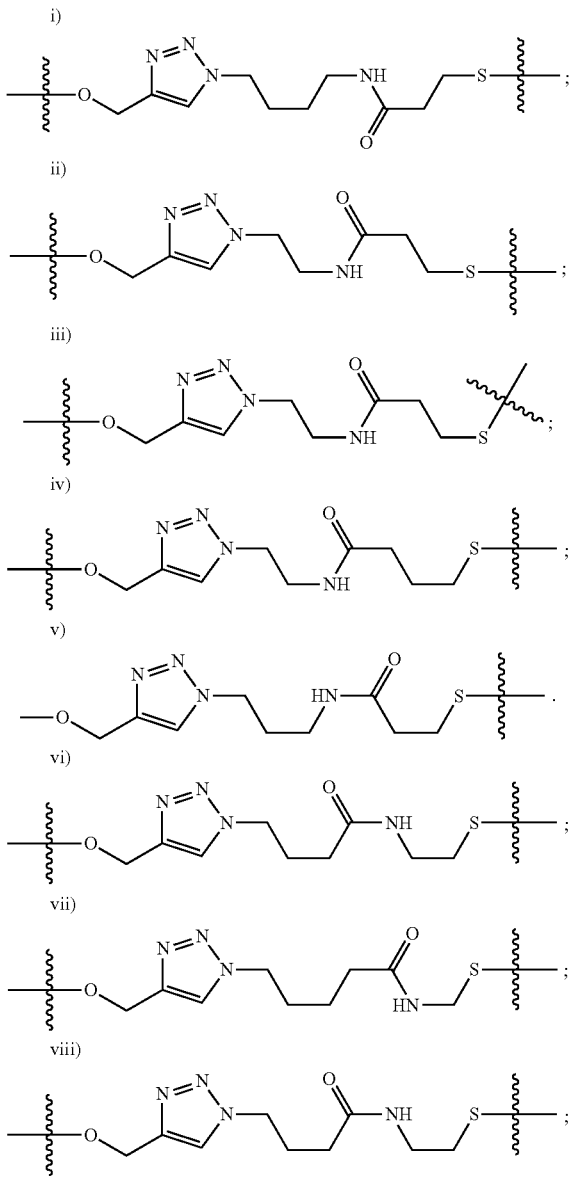

ix) —C(O)CH$_2$(OCH$_2$CH$_2$)$_2$NHC(O)CH$_2$(OCH$_2$CH$_2$)$_2$NHC(O)(CH$_2$)$_2$S—;

X) —C(O)CH$_2$(OCH$_2$CH$_2$)$_3$NHC(O)CH$_2$(OCH$_2$CH$_2$)$_3$NHC(O)(CH$_2$)$_2$S—;

Xi) —C(O)CH$_2$(OCH$_2$CH$_2$)$_4$NHC(O)CH$_2$(OCH$_2$CH$_2$)$_4$NHC(O)(CH$_2$)$_2$S—;

xii) —C(O)CH$_2$(OCH$_2$CH$_2$)$_2$C(O)NHCH$_2$(OCH$_2$CH$_2$)$_2$NHC(O)(CH$_2$)$_2$S—;

xiii) —C(O)CH$_2$(OCH$_2$CH$_2$)$_3$C(O)NHCH$_2$(OCH$_2$CH$_2$)$_3$NHC(O)(CH$_2$)$_2$S—; and viv) —C(O)CH$_2$(OCH$_2$CH$_2$)$_4$C(O)NHCH$_2$(OCH$_2$CH$_2$)$_4$NHC(O)(CH$_2$)$_2$S—.

10. An imaging agent according to claim 8, wherein L units have the formula:

wherein J, K, L and M are each independently chosen from:

i) —(CH$_2$)$_{yy}$O(CH$_2$)$_{zz}$—;
ii) —(CH$_2$)$_{yy}$NH(CH$_2$)$_{zz}$—;
iii) —(CH$_2$)$_{yy}$S(CH$_2$)$_{zz}$—;
iv) —(CH$_2$)$_{yy}$C(O)(CH$_2$)$_{zz}$—
v) —(CH$_2$)$_{yy}$OC(O)(CH$_2$)$_{zz}$—;
vi) —(CH$_2$)$_{yy}$C(O)O(CH$_2$)$_{zz}$—;
vii) —(CH$_2$)$_{yy}$NHC(O)(CH$_2$)$_{zz}$—;
viii) —(CH$_2$)$_{yy}$C(O)NH(CH$_2$)$_{zz}$—;
ix) —(CH$_2$)$_{yy}$NHC(O)NH(CH$_2$)$_{zz}$—;
x) —(CH$_2$)$_{yy}$C(S)(CH$_2$)$_{zz}$—;
xi) —(CH$_2$)$_{yy}$NHC(S)(CH$_2$)$_{zz}$—
xii) —(CH$_2$)$_{yy}$C(S)NH(CH$_2$)$_{zz}$—;
xiii) —(CH$_2$)$_{yy}$NHC(S)NH(CH$_2$)$_{zz}$—;
xiv) $C_3$-$C_{10}$ carbocyclic rings;
xv) aryl rings chosen from phenyl and napthyl;
xvi) heterocyclic rings comprising from 1 to 4 heteroatoms chosen from nitrogen (N), oxygen (O) and sulfur (S); and
xvii) heteroaryl rings comprising from 1 to 4 heteroatoms chosen from nitrogen (N), oxygen (O) and sulfur (S); and
xviii) any combination thereof for each of J, K, L and M;

the indices d, f, h and j are 0 or 1; the indices e, g and i are independently integers from 0 to 1.

11. An imaging agent according to claim 1, wherein Z has the formula:

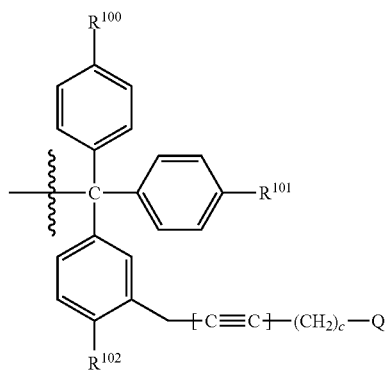

wherein $R^{100}$, $R^{101}$ and $R^{102}$ are each independently —$OR^{10}$; $R^{10}$ is $C_1$-$C_4$ alkyl, the index c is from 1 to 100.

12. An imaging agent according to claim 4, wherein Z has the formula:
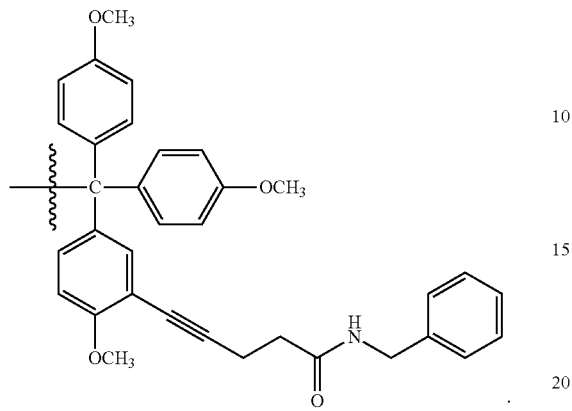
13. An imaging agent according to claim 1, wherein X has the formula chosen from:
i)
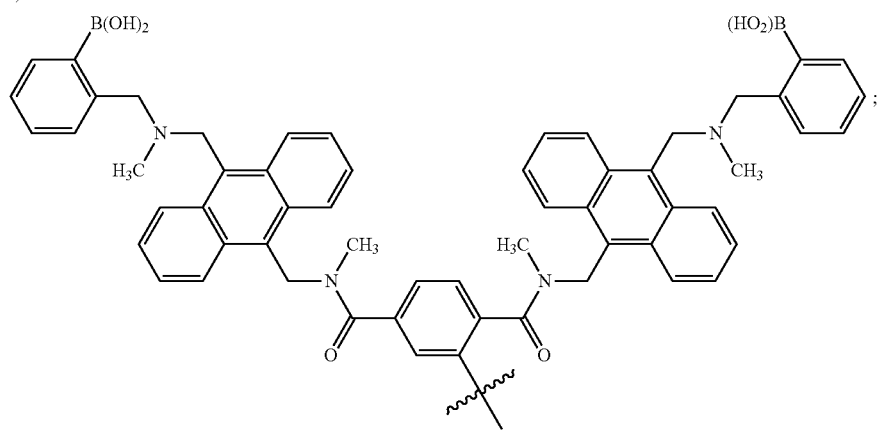
ii)
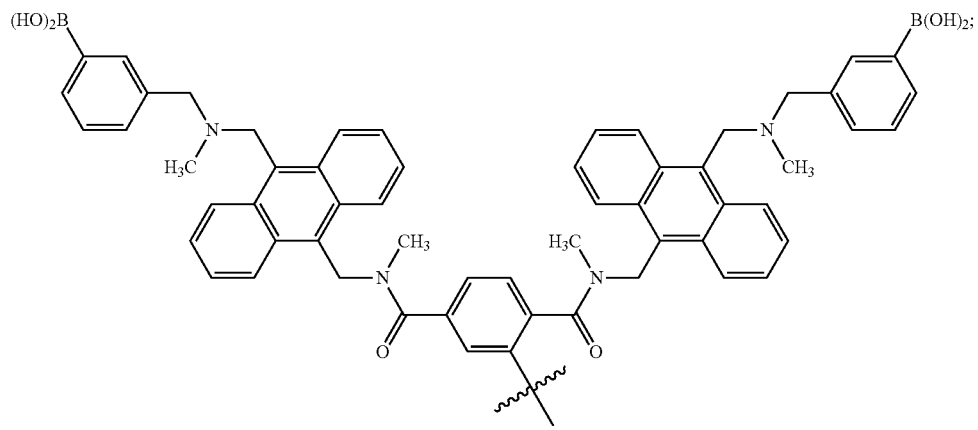

iii)
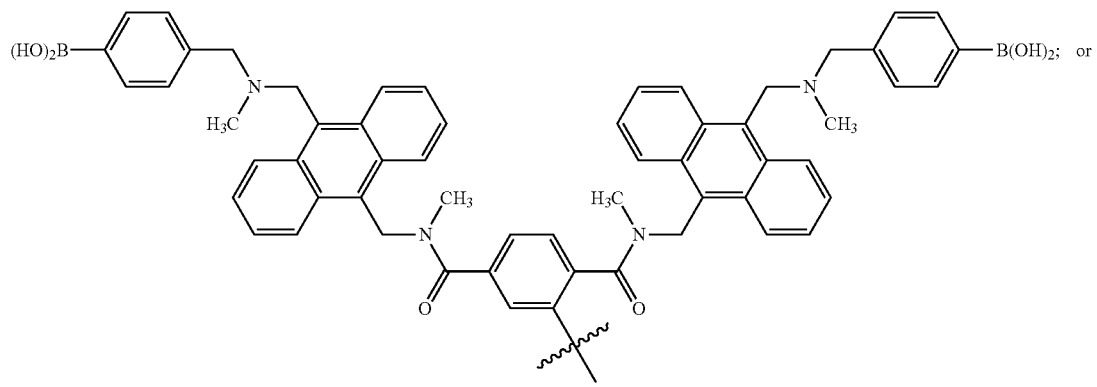
iv)
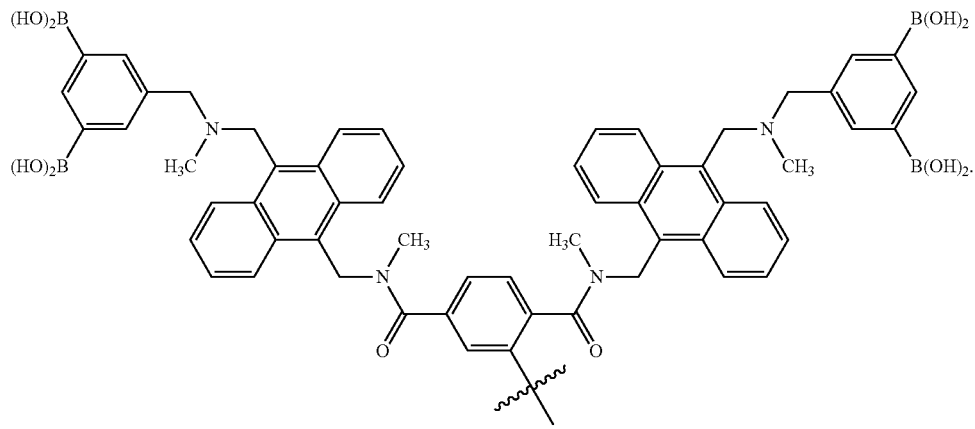
14. An imaging agent according to claim 8, having the formula:
i)
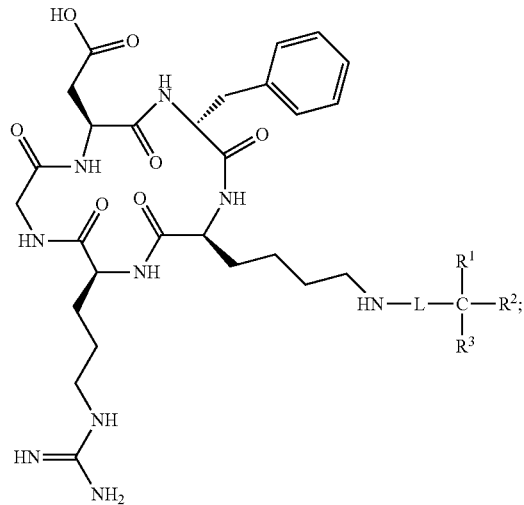
ii)
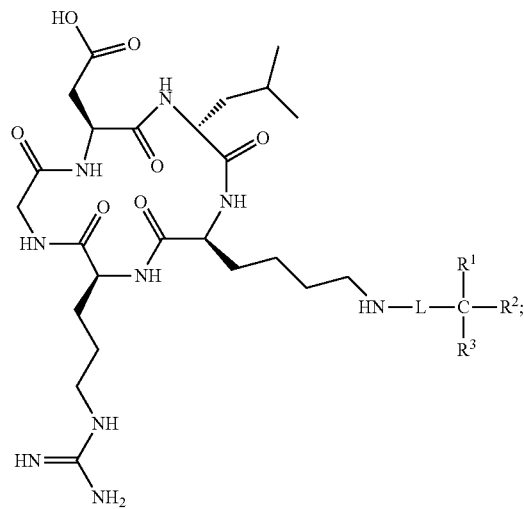

iii)
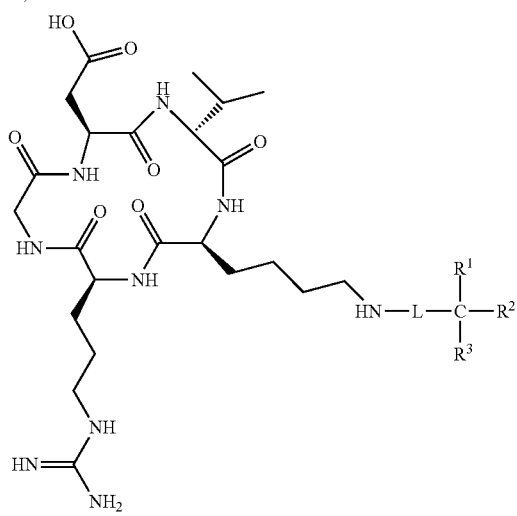
v)
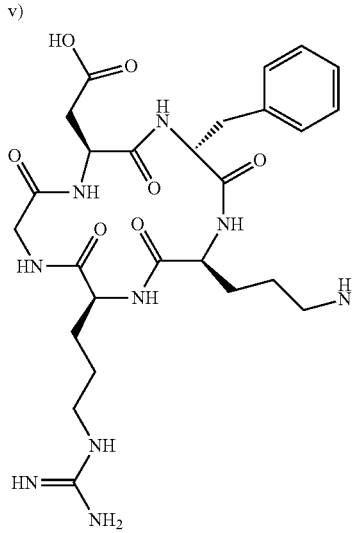
or
iv)
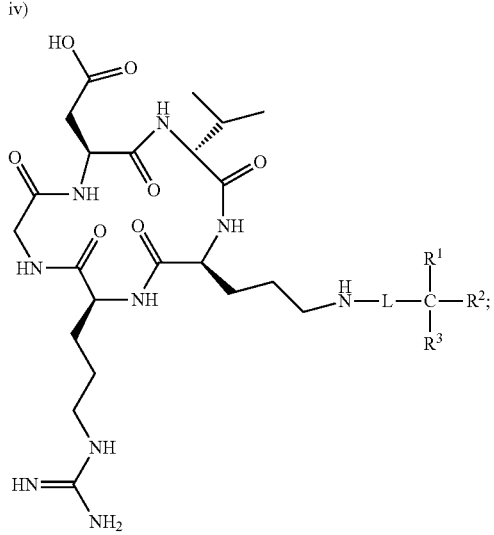
vi)
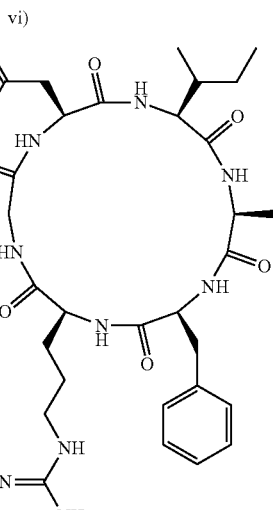
15. The imaging agent 2-((2S,5S,8S,11S)-5-Benzyl-8-(1-(3-(5-(benzylamino)-5-oxopent-1-yn-1-yl)-4-methoxyphenyl)-1,1-bis(4-mentoxyphenyl)-5,14,23-trioxo-9,12,18,21-tetraoxa-2-thia-6,15,24-triazaoctancosan-28-yl)-11-(3-guanidinopropyl)-3,6,9,12,15-pentaoxo-1,4,7,10,13-pentaazacyclopentadecan-2-yl)acetic acid having the formula:

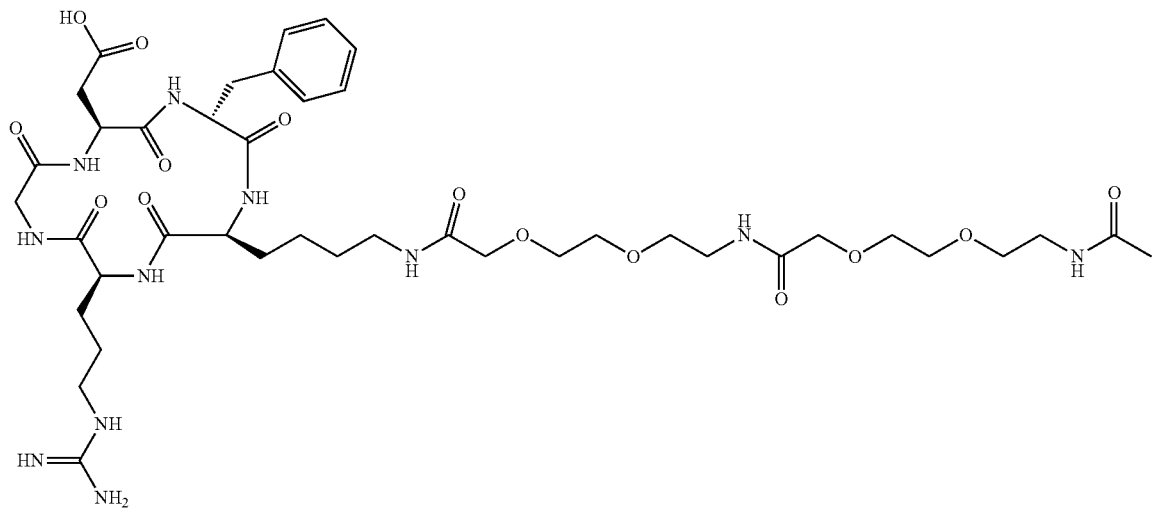

16. An imaging agent having the formula:

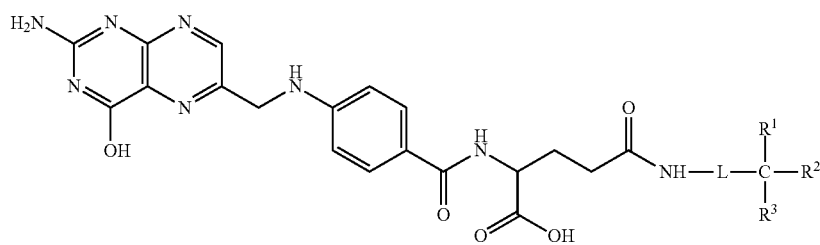

$R^1$ an $R^2$ are substituted or unsubstituted aryl groups chosen from phenyl, naphthyl, anthracenyl, phenanthrenyl, or tetracenyl;

$R^3$ is a substituted or unsubstituted aryl group chosen from phenyl, naphthyl, anthracenyl, phenanthrenyl, or tetracenyl, and wherein $R^3$ further comprises an anchoring group having the formula:

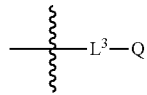

wherein Q is a unit having the formula:
i) $-(CH_2)_rC(O)O(CH_2)_tR^9$;
ii) $-(CH_2)_rOC(O)(CH_2)_tR^9$;
iii) $-(CH_2)_rC(O)NR^8(CH_2)_tR^9$;
iv) $-(CH_2)_rNR^8C(O)(CH_2)_tR^9$;
v) $-(CH_2)_rNR^8C(O)NH(CH_2)_tR^9$; and
vi) $-(CH_2)_rNR^8C(NR^8)NR^8(CH_2)_tR^9$;

$R^8$ is hydrogen or $C_1$-$C_3$ linear alkyl; the index r is an integer from 0 to 4 and the index t is an integer form 0 to 4; $R^9$ is phenyl or naphthyl;

$L^3$ comprises one or more units chosen from $-CH_2-$, $-CH=CH-$, $-C\equiv C-$, $-CH_2CH_2O-$, $-CH_2CH_2CH_2O-$, $-CH_2CH(CH_3)O-$, and $-CH(CH_3)CH_2O-$;

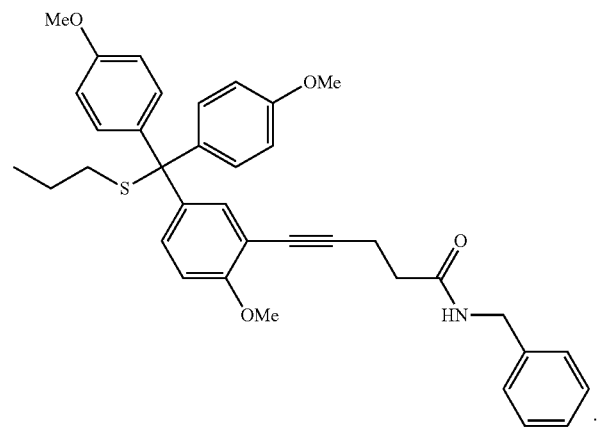

L is a linking unit that comprises a fragmentable bond such that under the conditions of MALDI-MS or other mass spectrum conditions releases a stable cation having the formula:

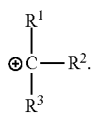

17. An imaging agent according to claim 16, wherein the unit

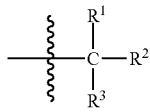

has the formula:

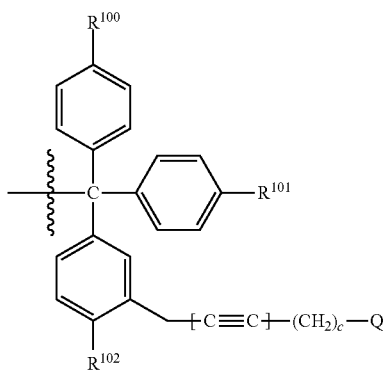

wherein $R^{100}$, $R^{101}$ and $R^{102}$ are each independently —$OR^{10}$; $R^{10}$ is $C_1$-$C_4$ alkyl, the index c is from 1 to 100.

18. An imaging agent according to claim 17, wherein the unit

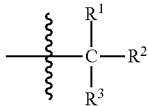

has the formula:

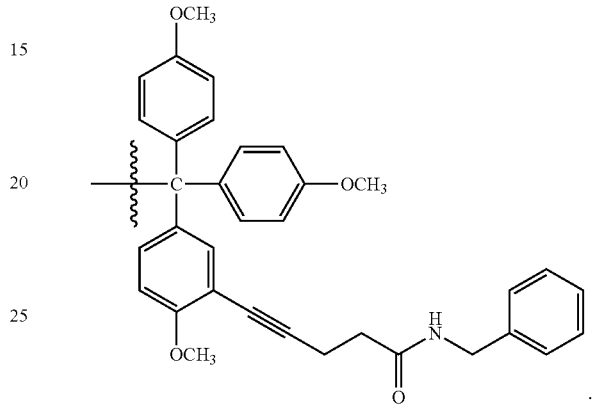

19. The imaging agent 18-(4-(((2-Amino-4-hydroxypte-ridin-6-yl)methyl)amino)benz-amido)-1-(1-(1-(3-(5-(ben-zylamino)-5-oxopent-1-yn-1-yl)-4-methoxyphenyl)-1,1-bis (4-methoxyphenyl)-5-oxo-10,13,16-trioxa-2-thia-6-azanonadecan-19-yl)-4-fluoro-4,5,6,7,8,9-hexahydro-1H-cycloocta[d][1,2,3]triazol-4-yl)-1,15-dioxo-5,8,11-trioxa-2, 14-diazanonadecan-19-oic acid having the formula:

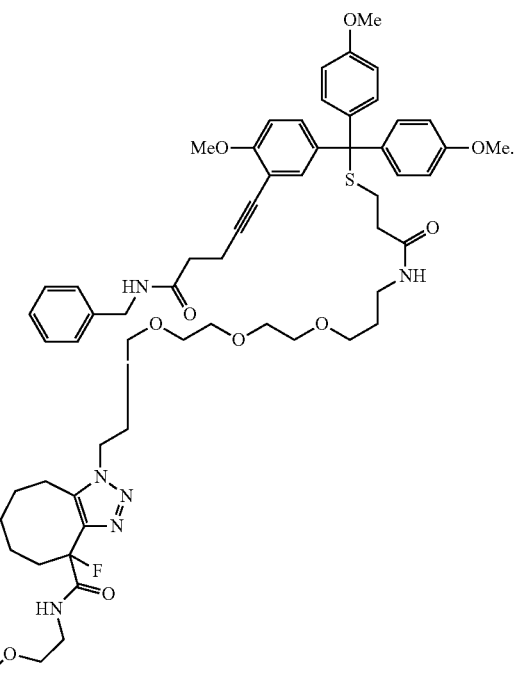

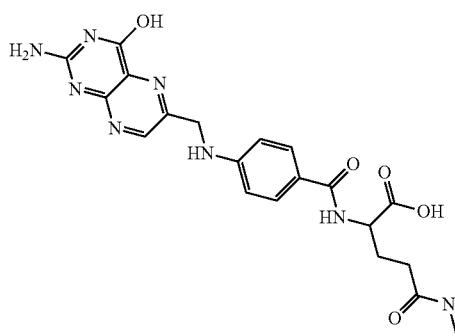

* * * * *

UNITED STATES PATENT AND TRADEMARK OFFICE
CERTIFICATE OF CORRECTION

PATENT NO. : 9,476,883 B2
APPLICATION NO. : 14/233400
DATED : October 25, 2016
INVENTOR(S) : Dai et al.

It is certified that error appears in the above-identified patent and that said Letters Patent is hereby corrected as shown below:

Column 1
Immediately following the title insert:

--FEDERALLY SPONSORED RESEARCH
This discovery was made with Government support under grants CA123329, CA88343 and GM084933 awarded by the National Institute of Health. The Government has certain rights in the invention.--

Signed and Sealed this
Seventeenth Day of January, 2017

Michelle K. Lee
*Director of the United States Patent and Trademark Office*